(12) United States Patent
Chien et al.

(10) Patent No.: US 7,491,808 B2
(45) Date of Patent: Feb. 17, 2009

(54) HCV NON-STRUCTURAL PROTEIN MUTANTS AND USES THEREOF

(75) Inventors: David Chien, Emeryville, CA (US);
Doris Coit, Emeryville, CA (US);
Celine Hu, Emeryville, CA (US);
Sansan Lin, Emeryville, CA (US);
Angelica Medina-Selby, Emeryville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 440 days.

(21) Appl. No.: 11/213,326

(22) Filed: Aug. 26, 2005

(65) Prior Publication Data

US 2006/0051745 A1 Mar. 9, 2006

Related U.S. Application Data

(60) Continuation-in-part of application No. 10/899,715, filed on Jul. 26, 2004, now Pat. No. 7,241,879, which is a continuation of application No. 10/637,323, filed on Aug. 8, 2003, now Pat. No. 6,797,809, which is a division of application No. 09/881,654, filed on Jun. 14, 2001, now Pat. No. 6,632,601, application No. 11/213,326, which is a continuation-in-part of application No. 10/643,853, filed on Aug. 19, 2003, now Pat. No. 7,319,144, which is a division of application No. 09/881,239, filed on Jun. 14, 2001, now Pat. No. 6,630,298.

(60) Provisional application No. 60/618,390, filed on Oct. 12, 2004, provisional application No. 60/604,858, filed on Aug. 27, 2004, provisional application No. 60/212,082, filed on Jun. 15, 2000, provisional application No. 60/280,811, filed on Apr. 2, 2001, provisional application No. 60/280,867, filed on Apr. 2, 2001, provisional application No. 60/212,082, filed on Jun. 15, 2000, provisional application No. 60/621,790, filed on Oct. 25, 2004, provisional application No. 60/621,502, filed on Oct. 22, 2004.

(51) Int. Cl.
*C07H 21/04* (2006.01)

(52) U.S. Cl. ............................. 536/23.4; 435/5; 530/350

(58) Field of Classification Search ....................... None
See application file for complete search history.

(56) References Cited

U.S. PATENT DOCUMENTS

| | | | |
|---|---|---|---|
| 5,371,017 | A | 12/1994 | Houghton et al. |
| 5,372,928 | A | 12/1994 | Miyamura et al. |
| 5,843,752 | A | 12/1998 | Dasmahapatra et al. |
| 6,153,579 | A | 11/2000 | Kim et al. |
| 6,211,338 | B1 | 4/2001 | Malcolm et al. |
| 6,333,186 | B1 | 12/2001 | Wittekind et al. |
| 6,524,589 | B1 | 2/2003 | Reichert et al. |
| 6,800,456 | B2 | 10/2004 | Wittekind et al. |
| 2002/0146685 | A1 * | 10/2002 | Chien et al. ..................... 435/5 |

FOREIGN PATENT DOCUMENTS

| | | |
|---|---|---|
| EP | 0 693 687 A1 | 1/1996 |
| WO | WO 97/44469 A2 | 11/1997 |
| WO | WO 00/01718 A2 | 1/2000 |
| WO | WO 01/30812 A2 | 5/2001 |
| WO | WO 01/38360 A2 | 5/2001 |
| WO | WO 2004/005473 A2 * | 1/2004 |

OTHER PUBLICATIONS

Bartenschlager et al. Nonstructural protein 3 of the hepatitis C virus encodes a serine-type proteinase required for cleavage at the NS3/4 and NS4/5 junctions. Journal of Virology, Jul. 1993, vol. 67, No. 7, 3835-3844.*
Bartenschlager et al., "Nonstructural protein 3 of the hepatitis C virus encodes a serine-type proteinase required for cleavage at the NS3/4 and NS4/5 junctions," J. Virology 67:3835-3844, 1993.
Botarelli et al., "T-lymphocyte response to hepatitis C virus in different clinical courses of infection," Gastroenterology 104:580-587, 1993.
Chen et al., "Human and murine antibody recognition is focused on the ATPase/Helicase, but not the protease domain of the hepatitis C virus nonstructural 3 protein," Hepatology 28:219-224, 1998.
Choo et al., "Genetic organization and diversity of the hepatitis C virus," Proc. Natl. Acad. Sci. USA 88:22451-5, 1991.
Cooper et al., "Analysis of a successful immune response against hepatitis C virus," Immunity 10:439-449, 1999.
De Francesco et al., "The hepatitis C virus NS3 proteinase: structure and function of a zinc-containing serine proteinase," Antiviral Therapy 3(Supp. 3):99-109, 1998.
Diepolder et al., "Possible mechanism involving T-lymphocyte response to non-structural protein 3 in viral clearance in acute hepatitis C virus infection," Lancet 346:1006-1007, 1995.
Diepolder et al., "Immunodominant CD4 T-cell epitope within nonstructural protein 3 in acute hepatitis C virus infection," J. Virology 71:6011-6019, 1997.
Eckart et al., "The Hepatitis C Virus Encodes a Serine Protease Involved in Processing of the Putative Nonstructural Proteins from the Viral Polyprotein Precursor," Biochemical and Biophysical Research Communications, vol. 192(2):399-406, 1993.
Ferrari et al., "T-cell response to structural and nonstructural hepatitis C virus antigens in persistent and self-limited hepatitis C virus infections," Hepatology 19:286-295, 1994.
Grakoui et al., "Characterization of the Hepatitis C Virus-Encoded Serine Proteinase: Determination of Proteinase-Dependent Polyprotein Cleavage Sites," Jor. Virol. 67(5):2832-43, 1993.

(Continued)

*Primary Examiner*—Emily M. Le
(74) *Attorney, Agent, or Firm*—Mark Seka; Robert Robins; Robert Gorman

(57) ABSTRACT

Modified HCV non-structural proteins are described. The proteins include modified NS3 domains such that proteolytic activity of the NS3 molecule is inhibited. The modified proteins retain conformational epitopes. HCV immunoassays including the modified NS3 molecules are also described.

14 Claims, 25 Drawing Sheets

OTHER PUBLICATIONS

Hoffman et al., "Mapping of immunodominant CD4 T lymphocyte epitiopes of hepatitis C virus antigens and their relevance durign the course of chronic infection," Hepatology 21:632-638, 1995.

Iwata et al., "Interferon gamma production by peripheral blood lymphocytes to hepatitis C virus core protein in chronic hepatitis C infection," Hepatology 22:1057-1064, 1995.

Koch et al., "Role of Charged Residues in the Catalytic Mechanism of Hepatitis C Virus NS3 Protease: Electrostatic Precollision Guidance and Transition-State Stabilization," Biochem. 40:631-640, 2001.

Lin et al., "Immunoreactive HCV NS3/4a Protein Without NS3 Serine Protease Activity," Transfusion 44(Supp):86A, 2004.

Minutello et al., "Compartmentalization of T lymphocytes to the site of disease: intrahepatic CD4 T cells specific for the protein NS4 of hepatitis C virus in patients with chronic hepatitis C," J. Exp. Med. 178:17-25, 1993.

Missale et al., "Different clinical behaviors of acute hepatitis C virus infection are associated with different vigor of the anti-viral cell-mediated immune response," J. Clin. Invest. 98:706-714, 1996.

Schechter et al., "On the size of the active site in proteases," Biochem. Biophys. Res. Comm. 27(2):157-62, 1967.

Tsai et al., "Detection of type 2-like T-helper cells in hepatitis C virus infection: implications for hepatitis C virus chronicity," Hepatology 25:449-458, 1997.

Tsai et al., "Cellular immune responses in patients with dual infection of hepatitis B and C viruses: dominant role of hepatitis C virus," Hepatology 21:908-912, 1995.

Dimasi et al., "Engineering, Characterization and Phage Display of Hepatitis C Virus NS3 Protease and NS4a Cofactor Peptide as a Single-Chain Protein," Protein Engineering 11(12):1257-1265 (1998).

Howe et al., "A Novel Recombinant Single-Cain Hepatitis C Virus NS3-NS4a Protein With Improved Helicase Activity," Protein Science 8:1332-1341 (1999).

Lin et al., "A Central Region in the Hepatitis C Virus NS4a Protein Allows Formation of an Active NS3-NS4a Serine Proteinase Complex in Vivo and in Vitro," Journal of Virology 69(7):4373-4380 (1995).

Lin et al., "The Hepatitis C Virus NS3 Serine Proteinase and NS4a Cofactor: Establishment of a Cell-Free Trans-Processing Assay," Proc. Natl. Acad. Sci. 92:7622-7626 (1995).

Pasquo et al., "Rational Design and Functional Expression of a Constitutively Active Single-Chain NS4a-NS3 Proteinase," Research Paper, Folding & Design 3(6):433-441 (1998).

Taremi et al., "Construction, Expression, and Characterization of a Novel Fully Activated Recombinant Single-Chain Hepatitis C Virus Protease," Protein Science 7:2143-2149 (1998).

* cited by examiner

```
                              1                                    10
                              M    A    P    I    T    A    Y    A    Q    Q
                              ATG  GCG  CCC  ATC  ACG  GCG  TAC  GCC  CAG  CAG

20
      T    R    G    L    L    G    C    I    I    T    S    L    T    G    R
      ACA  AGG  GGC  CTC  CTA  GGG  TGC  ATA  ATC  ACC  AGC  CTA  ACT  GGC  CGG 30                                              40
      D    K    N    Q    V    E    G    E    V    Q    I    V    S    T    A
      GAC  AAA  AAC  CAA  GTG  GAG  GGT  GAG  GTC  CAG  ATT  GTG  TCA  ACT  GCT

50
      A    Q    T    F    L    A    T    C    I    N    G    V    C    W    T
      GCC  CAA  ACC  TTC  CTG  GCA  ACG  TGC  ATC  AAT  GGG  GTG  TGC  TGG  ACT 60                                         70
      V    Y    H    G    A    G    T    R    T    I    A    S    P    K    G
      GTC  TAC  CAC  GGG  GCC  GGA  ACG  AGG  ACC  ATC  GCG  TCA  CCC  AAG  GGT

80
      P    V    I    Q    M    Y    T    N    V    D    Q    D    L    V    G
      CCT  GTC  ATC  CAG  ATG  TAT  ACC  AAT  GTA  GAC  CAA  GAC  CTT  GTG  GGC 90                                         100
      W    P    A    P    Q    G    S    R    S    L    T    P    C    T    C
      TGG  CCC  GCT  CCG  CAA  GGT  AGC  CGA  TCA  TTG  ACA  CCC  TGC  ACT  TGC

110
      G    S    S    D    L    Y    L    V    T    R    H    A    D    V    I
      GGC  TCC  TCG  GAC  CTT  TAC  CTG  GTC  ACG  AGG  CAC  GCC  GAT  GTC  ATT 120                                             130
      P    V    R    R    R    G    D    S    R    G    S    L    L    S    P
      CCC  GTG  CGC  CGG  CGG  GGT  GAT  AGC  AGG  GGC  AGC  CTG  CTG  TCG  CCC

140
      R    P    I    S    Y    L    K    G    S    S    G    G    P    L    L
      CGG  CCC  ATT  TCC  TAC  TTG  AAA  GGC  TCC  TCG  GGG  GGT  CCG  CTG  TTG 150                                        160
      C    P    A    G    H    A    V    G    I    F    R    A    A    V    C
      TGC  CCC  GCG  GGG  CAC  GCC  GTG  GGC  ATA  TTT  AGG  GCC  GCG  GTG  TGC

170
      T    R    G    V    A    K    A    V    D    F    I    P    V    E    N
      ACC  CGT  GGA  GTG  GCT  AAG  GCG  GTG  GAC  TTT  ATC  CCT  GTG  GAG  AAC

180
      L    E    T    T    M    R    S
      CTA  GAG  ACA  ACC  ATG  AGG  TCC
```

FIG. 3

```
                    1                                          10
                    M   A   P   I   T   A   Y   A   Q   Q   T   R   G   L   L
                   ATG GCG CCC ATC ACG GCG TAC GCC CAG CAG ACA AGG GGC CTC CTA
                        20                                     30
        G   C   I   I   T   S   L   T   G   R   D   K   N   Q   V   E   G   E   V   Q
       GGG TGC ATA ATC ACC AGC CTA ACT GGC CGG GAC AAA AAC CAA GTG GAG GGT GAG GTC CAG
                        40                                     50
        I   V   S   T   A   A   Q   T   F   L   A   T   C   I   N   G   V   C   W   T
       ATT GTG TCA ACT GCT GCC CAA ACC TTC CTG GCA ACG TGC ATC AAT GGG GTG TGC TGG ACT
                        60                                     70
        V   Y   H   G   A   G   T   R   T   I   A   S   P   K   G   P   V   I   Q   M
       GTC TAC CAC GGG GCC GGA ACG AGG ACC ATC GCG TCA CCC AAG GGT CCT GTC ATC CAG ATG
                        80                                     90
        Y   T   N   V   D   Q   D   L   V   G   W   P   A   P   Q   G   S   R   S   L
       TAT ACC AAT GTA GAC CAA GAC CTT GTG GGC TGG CCC GCT CCG CAA GGT AGC CGA TCA TTG
                       100                                    110
        T   P   C   T   C   G   S   S   D   L   Y   L   V   T   R   H   A   D   V   I
       ACA CCC TGC ACT TGC GGC TCC TCG GAC CTT TAC CTG GTC ACG AGG CAC GCC GAT GTC ATT
                       120                                    130
        P   V   R   R   R   G   D   S   R   G   S   L   L   S   P   R   P   I   S   Y
       CCC GTG CGC CGG CGG GGT GAT AGC AGG GGC AGC CTG CTG TCG CCC CGG CCC ATT TCC TAC
                       140                                    150
        L   K   G   S   A   G   G   P   L   L   C   P   A   G   H   A   V   G   I   F
       TTG AAA GGC TCC GCA GGG GGT CCG CTG TTG TGC CCC GCG GGG CAC GCC GTG GGC ATA TTT
                       160                                    170
        R   A   A   V   C   T   R   G   V   A   K   A   V   D   F   I   P   V   E   N
       AGG GCC GCG GTG TGC ACC CGT GGA GTG GCT AAG GCG GTG GAC TTT ATC CCT GTG GAG AAC
                       180                                    190
        L   E   T   T   M   R   S   P   V   F   T   D   N   S   S   P   P   V   V   P
       CTA GAG ACA ACC ATG AGG TCC CCG GTG TTC ACG GAT AAC TCC TCT CCA CCA GTA GTG CCC
                       200                                    210
        Q   S   F   Q   V   A   H   L   H   A   P   T   G   S   G   K   S   T   K   V
       CAG AGC TTC CAG GTG GCT CAC CTC CAT GCT CCC ACA GGC AGC GGC AAA AGC ACC AAG GTC
                       220                                    230
        P   A   A   Y   A   A   Q   G   Y   K   V   L   V   L   N   P   S   V   A   A
       CCG GCT GCA TAT GCA GCT CAG GGC TAT AAG GTG CTA GTA CTC AAC CCC TCT GTT GCT GCA
                       240                                    250
        T   L   G   F   G   A   Y   M   S   K   A   H   G   I   D   P   N   I   R   T
       ACA CTG GGC TTT GGT GCT TAC ATG TCC AAG GCT CAT GGG ATC GAT CCT AAC ATC AGG ACC
                       260                                    270
        G   V   R   T   I   T   T   G   S   P   I   T   Y   S   T   Y   G   K   F   L
       GGG GTG AGA ACA ATT ACC ACT GGC AGC CCC ATC ACG TAC TCC ACC TAC GGC AAG TTC CTT
```

FIG. 5A

```
            280                                              290
A   D   G   G   C   S   G   G   A   Y   D   I   I   I   C   D   E   C   H   S
GCC GAC GGC GGG TGC TCG GGG GGC GCT TAT GAC ATA ATA ATT TGT GAC GAG TGC CAC TCC 300                                              310
T   D   A   T   S   I   L   G   I   G   T   V   L   D   Q   A   E   T   A   G
ACG GAT GCC ACA TCC ATC TTG GGC ATT GGC ACT GTC CTT GAC CAA GCA GAG ACT GCG GGG 320                                              330
A   R   L   V   V   L   A   T   A   T   P   P   G   S   V   T   V   P   H   P
GCG AGA CTG GTT GTG CTC GCC ACC GCC ACC CCT CCG GGC TCC GTC ACT GTG CCC CAT CCC 340                                              350
N   I   E   E   V   A   L   S   T   T   G   E   I   P   F   Y   G   K   A   I
AAC ATC GAG GAG GTT GCT CTG TCC ACC ACC GGA GAG ATC CCT TTT TAC GGC AAG GCT ATC 360                                              370
P   L   E   V   I   K   G   G   R   H   L   I   F   C   H   S   K   K   K   C
CCC CTC GAA GTA ATC AAG GGG GGG AGA CAT CTC ATC TTC TGT CAT TCA AAG AAG AAG TGC 380                                              390
D   E   L   A   A   K   L   V   A   L   G   I   N   A   V   A   Y   Y   R   G
GAC GAA CTC GCC GCA AAG CTG GTC GCA TTG GGC ATC AAT GCC GTG GCC TAC TAC CGC GGT 400                                              410
L   D   V   S   V   I   P   P   I   G   D   V   V   V   V   A   T   D   A   L
CTT GAC GTG TCC GTC ATC CCG CCC ATC GGC GAT GTT GTC GTC GTG GCA ACC GAT GCC CTC 420                                              430
M   T   G   Y   T   G   D   F   D   S   V   I   D   C   N   T   C   V   T   Q
ATG ACC GGC TAT ACC GGC GAC TTC GAC TCG GTG ATA GAC TGC AAT ACG TGT GTC ACC CAG 440                                              450
T   V   D   F   S   L   D   P   T   F   T   I   E   T   I   T   L   P   Q   D
ACA GTC GAT TTC AGC CTT GAC CCT ACC TTC ACC ATT GAG ACA ATC ACG CTC CCC CAA GAT 460                                              470
A   V   S   R   T   Q   R   R   G   R   T   G   R   G   K   P   G   I   Y   R
GCT GTC TCC CGC ACT CAA CGT CGG GGC AGG ACT GGC AGG GGG AAG CCA GGC ATC TAC AGA 480                                              490
F   V   A   P   G   E   R   P   S   G   M   F   D   S   S   V   L   C   E   C
TTT GTG GCA CCG GGG GAG CGC CCC TCC GGC ATG TTC GAC TCG TCC GTC CTC TGT GAG TGC 500                                              510
Y   D   A   G   C   A   W   Y   E   L   T   P   A   E   T   T   V   R   L   R
TAT GAC GCA GGC TGT GCT TGG TAT GAG CTC ACG CCC GCC GAG ACT ACA GTT AGG CTA CGA 520                                              530
A   Y   M   N   T   P   G   L   P   V   C   Q   D   H   L   E   F   W   E   G
GCG TAC ATG AAC ACC CCG GGG CTT CCC GTG TGC CAG GAC CAT CTT GAA TTT TGG GAG GGC 540                                              550
V   F   T   G   L   T   H   I   D   A   H   F   L   S   Q   T   K   Q   S   G
GTC TTT ACA GGC CTC ACT CAT ATA GAT GCC CAC TTT CTA TCC CAG ACA AAG CAG AGT GGG 560                                              570
E   N   L   P   Y   L   V   A   Y   Q   A   T   V   C   A   R   A   Q   A   P
GAG AAC CTT CCT TAC CTG GTA GCG TAC CAA GCC ACC GTG TGC GCT AGG GCT CAA GCC CCT
```

FIG. 5B

```
                             580                                           590
    P    P    S    W    D    Q    M    W    K    C    L    I    R    L    K    P    T    L    H    G
   CCC  CCA  TCG  TGG  GAC  CAG  ATG  TGG  AAG  TGT  TTG  ATT  CGC  CTC  AAG  CCC  ACC  CTC  CAT  GGG 600                                           610
    P    T    P    L    L    Y    R    L    G    A    V    Q    N    E    I    T    L    T    H    P
   CCA  ACA  CCC  CTG  CTA  TAC  AGA  CTG  GGC  GCT  GTT  CAG  AAT  GAA  ATC  ACC  CTG  ACG  CAC  CCA 620                                           630
    V    T    K    Y    I    M    T    C    M    S    A    D    L    E    V    V    T    S    T    W
   GTC  ACC  AAA  TAC  ATC  ATG  ACA  TGC  ATG  TCG  GCC  GAC  CTG  GAG  GTC  GTC  ACG  AGC  ACC  TGG 640                                           650
    V    L    V    G    G    V    L    A    A    L    A    A    Y    C    L    S    T    G    C    V
   GTG  CTC  GTT  GGC  GGC  GTC  CTG  GCT  GCT  TTG  GCC  GCG  TAT  TGC  CTG  TCA  ACA  GGC  TGC  GTG 660                                           670
    V    I    V    G    R    V    V    L    S    G    K    P    A    I    I    P    D    R    E    V
   GTC  ATA  GTG  GGC  AGG  GTC  GTC  TTG  TCC  GGG  AAG  CCG  GCA  ATC  ATA  CCT  GAC  AGG  GAA  GTC 680                       686
    L    Y    R    E    F    D    E    M    E    E    C    OP
   CTC  TAC  CGA  GAG  TTC  GAT  GAG  ATG  GAA  GAG  TGC  TGA
```

FIG. 5C

```
                            1                                              10
                            M   A   P   I   T   A   Y   A   Q   Q   T   R   G   L   L
                            ATG GCG CCA ATC ACT GCT TAC GCT CAA CAA ACC AGA GGC CTC CTA 20                                              30
        G   C   I   I   T   S   L   T   G   R   D   K   N   Q   V   E   G   E   V   Q
        GGG TGC ATA ATC ACC AGC CTA ACT GGC CGG GAC AAA AAC CAA GTG GAG GGT GAG GTC CAG 40                                              50
        I   V   S   T   A   A   Q   T   F   L   A   T   C   I   N   G   V   C   W   T
        ATT GTG TCA ACT GCT GCC CAA ACC TTC CTG GCA ACG TGC ATC AAT GGG GTG TGC TGG ACT 60                                              70
        V   Y   H   G   A   G   T   R   T   I   A   S   P   K   G   P   V   I   Q   M
        GTC TAC CAC GGG GCC GGA ACG AGG ACC ATC GCG TCA CCC AAG GGT CCT GTC ATC CAG ATG 80                                              90
        Y   T   N   V   D   Q   D   L   V   G   W   P   A   P   Q   G   S   R   S   L
        TAT ACC AAT GTA GAC CAA GAC CTT GTG GGC TGG CCC GCT CCG CAA GGT AGC CGA TCA TTG 100                                             110
        T   P   C   T   C   G   S   S   D   L   Y   L   V   T   R   H   A   D   V   I
        ACA CCC TGC ACT TGC GGC TCC TCG GAC CTT TAC CTG GTC ACG AGG CAC GCC GAT GTC ATT 120                                             130
        P   V   R   R   R   G   D   S   R   G   S   L   L   S   P   R   P   I   S   Y
        CCC GTG CGC CGG CGG GGT GAT AGC AGG GGC AGC CTG CTG TCG CCC CGG CCC ATT TCC TAC 140                                             150
        L   K   G   S   A   G   G   P   L   L   C   P   A   G   H   A   V   G   I   F
        TTG AAA GGC TCC GCA GGG GGT CCG CTG TTG TGC CCC GCG GGG CAC GCC GTG GGC ATA TTT 160                                             170
        R   A   A   V   C   T   R   G   V   A   K   A   V   D   F   I   P   V   E   N
        AGG GCC GCG GTG TGC ACC CGT GGA GTG GCT AAG GCG GTG GAC TTT ATC CCT GTG GAG AAC 180                                             190
        L   E   T   T   M   R   S   P   V   F   T   D   N   S   S   P   P   V   V   P
        CTA GAG ACA ACC ATG AGG TCC CCG GTG TTC ACG GAT AAC TCC TCT CCA CCA GTA GTG CCC 200                                             210
        Q   S   F   Q   V   A   H   L   H   A   P   T   G   S   G   K   S   T   K   V
        CAG AGC TTC CAG GTG GCT CAC CTC CAT GCT CCC ACA GGC AGC GGC AAA AGC ACC AAG GTC 220                                             230
        P   A   A   Y   A   A   Q   G   Y   K   V   L   V   L   N   P   S   V   A   A
        CCG GCT GCA TAT GCA GCT CAG GGC TAT AAG GTG CTA GTA CTC AAC CCC TCT GTT GCT GCA 240                                             250
        T   L   G   F   G   A   Y   M   S   K   A   H   G   I   D   P   N   I   R   T
        ACA CTG GGC TTT GGT GCT TAC ATG TCC AAG GCT CAT GGG ATC GAT CCT AAC ATC AGG ACC 260                                             270
        G   V   R   T   I   T   T   G   S   P   I   T   Y   S   T   Y   G   K   F   L
        GGG GTG AGA ACA ATT ACC ACT GGC AGC CCC ATC ACG TAC TCC ACC TAC GGC AAG TTC CTT
```

FIG. 6A

```
              280                                          290
  A   D   G   G   C   S   G   G   A   Y   D   I   I   I   C   D   E   C   H   S
 GCC GAC GGC GGG TGC TCG GGG GGC GCT TAT GAC ATA ATA ATT TGT GAC GAG TGC CAC TCC 300                                          310
  T   D   A   T   S   I   L   G   I   G   T   V   L   D   Q   A   E   T   A   G
 ACG GAT GCC ACA TCC ATC TTG GGC ATT GGC ACT GTC CTT GAC CAA GCA GAG ACT GCG GGG 320                                          330
  A   R   L   V   V   L   A   T   A   T   P   P   G   S   V   T   V   P   H   P
 GCG AGA CTG GTT GTG CTC GCC ACC GCC ACC CCT CCG GGC TCC GTC ACT GTG CCC CAT CCC 340                                          350
  N   I   E   E   V   A   L   S   T   T   G   E   I   P   F   Y   G   K   A   I
 AAC ATC GAG GAG GTT GCT CTG TCC ACC ACC GGA GAG ATC CCT TTT TAC GGC AAG GCT ATC 360                                          370
  P   L   E   V   I   K   G   G   R   H   L   I   F   C   H   S   K   K   K   C
 CCC CTC GAA GTA ATC AAG GGG GGG AGA CAT CTC ATC TTC TGT CAT TCA AAG AAG AAG TGC 380                                          390
  D   E   L   A   A   K   L   V   A   L   G   I   N   A   V   A   Y   Y   R   G
 GAC GAA CTC GCC GCA AAG CTG GTC GCA TTG GGC ATC AAT GCC GTG GCC TAC TAC CGC GGT 400                                          410
  L   D   V   S   V   I   P   P   I   G   D   V   V   V   V   A   T   D   A   L
 CTT GAC GTG TCC GTC ATC CCG CCC ATC GGC GAT GTT GTC GTC GTG GCA ACC GAT GCC CTC 420                                          430
  M   T   G   Y   T   G   D   F   D   S   V   I   D   C   N   T   C   V   T   Q
 ATG ACC GGC TAT ACC GGC GAC TTC GAC TCG GTG ATA GAC TGC AAT ACG TGT GTC ACC CAG 440                                          450
  T   V   D   F   S   L   D   P   T   F   T   I   E   T   I   T   L   P   Q   D
 ACA GTC GAT TTC AGC CTT GAC CCT ACC TTC ACC ATT GAG ACA ATC ACG CTC CCC CAA GAT 460                                          470
  A   V   S   R   T   Q   R   R   G   R   T   G   R   G   K   P   G   I   Y   R
 GCT GTC TCC CGC ACT CAA CGT CGG GGC AGG ACT GGC AGG GGG AAG CCA GGC ATC TAC AGA 480                                          490
  F   V   A   P   G   E   R   P   S   G   M   F   D   S   S   V   L   C   E   C
 TTT GTG GCA CCG GGG GAG CGC CCC TCC GGC ATG TTC GAC TCG TCC GTC CTC TGT GAG TGC 500                                          510
  Y   D   A   G   C   A   W   Y   E   L   T   P   A   E   T   T   V   R   L   R
 TAT GAC GCA GGC TGT GCT TGG TAT GAG CTC ACG CCC GCC GAG ACT ACA GTT AGG CTA CGA 520                                          530
  A   Y   M   N   T   P   G   L   P   V   C   Q   D   H   L   E   F   W   E   G
 GCG TAC ATG AAC ACC CCG GGG CTT CCC GTG TGC CAG GAC CAT CTT GAA TTT TGG GAG GGC 540                                          550
  V   F   T   G   L   T   H   I   D   A   H   F   L   S   Q   T   K   Q   S   G
 GTC TTT ACA GGC CTC ACT CAT ATA GAT GCC CAC TTT CTA TCC CAG ACA AAG CAG AGT GGG 560                                          570
  E   N   L   P   Y   L   V   A   Y   Q   A   T   V   C   A   R   A   Q   A   P
 GAG AAC CTT CCT TAC CTG GTA GCG TAC CAA GCC ACC GTG TGC GCT AGG GCT CAA GCC CCT
```

FIG. 6B

```
              580                                              590
    P   P   S   W   D   Q   M   W   K   C   L   I   R   L   K   P   T   L   H   G
   CCC CCA TCG TGG GAC CAG ATG TGG AAG TGT TTG ATT CGC CTC AAG CCC ACC CTC CAT GGG 600                                              610
    P   T   P   L   L   Y   R   L   G   A   V   Q   N   E   I   T   L   T   H   P
   CCA ACA CCC CTG CTA TAC AGA CTG GGC GCT GTT CAG AAT GAA ATC ACC CTG ACG CAC CCA 620                                              630     632
    V   T   K   Y   I   M   T   C   M   S   A   D   L   E   V   V   T   OP
   GTC ACC AAA TAC ATC ATG ACA TGC ATG TCG GCC GAC CTG GAG GTC GTC ACG TGA
```

FIG. 6C

```
          1                                           10
          M   G   C   V   V   I   V   G   R   V   V   L   S   G   S
          ATG GGC TGC GTG GTC ATA GTG GGC AGG GTC GTC TTG TCC GGT TCC 20                                          30
  G   S   I   T   A   Y   A   Q   Q   T   R   G   L   L   G   C   I   I   T   S
  GGT TCC ATC ACT GCT TAC GCT CAA CAA ACC AGA GGC CTC CTA GGG TGC ATA ATC ACC AGC 40                                          50
  L   T   G   R   D   K   N   Q   V   E   G   E   V   Q   I   V   S   T   A   A
  CTA ACT GGC CGG GAC AAA AAC CAA GTG GAG GGT GAG GTC CAG ATT GTG TCA ACT GCT GCC 60                                          70
  Q   T   F   L   A   T   C   I   N   G   V   C   W   T   V   Y   H   G   A   G
  CAA ACC TTC CTG GCA ACG TGC ATC AAT GGG GTG TGC TGG ACT GTC TAC CAC GGG GCC GGA 80                                          90
  T   R   T   I   A   S   P   K   G   P   V   I   Q   M   Y   T   N   V   D   Q
  ACG AGG ACC ATC GCG TCA CCC AAG GGT CCT GTC ATC CAG ATG TAT ACC AAT GTA GAC CAA 100                                         110
  D   L   V   G   W   P   A   P   Q   G   S   R   S   L   T   P   C   T   C   G
  GAC CTT GTG GGC TGG CCC GCT CCG CAA GGT AGC CGA TCA TTG ACA CCC TGC ACT TGC GGC 120                                         130
  S   S   D   L   Y   L   V   T   R   H   A   D   V   I   P   V   R   R   R   G
  TCC TCG GAC CTT TAC CTG GTC ACG AGG CAC GCC GAT GTC ATT CCC GTG CGC CGG CGG GGT 140                                         150
  D   S   R   G   S   L   L   S   P   R   P   I   S   Y   L   K   G   S   A   G
  GAT AGC AGG GGC AGC CTG CTG TCG CCC CGG CCC ATT TCC TAC TTG AAA GGC TCC GCA GGG 160                                         170
  G   P   L   L   C   P   A   G   H   A   V   G   I   F   R   A   A   V   C   T
  GGT CCG CTG TTG TGC CCC GCG GGG CAC GCC GTG GGC ATA TTT AGG GCC GCG GTG TGC ACC 180                                         190
  R   G   V   A   K   A   V   D   F   I   P   V   E   N   L   E   T   T   M   R
  CGT GGA GTG GCT AAG GCG GTG GAC TTT ATC CCT GTG GAG AAC CTA GAG ACA ACC ATG AGG 200                                         210
  S   P   V   F   T   D   N   S   S   P   P   V   V   P   Q   S   F   Q   V   A
  TCC CCG GTG TTC ACG GAT AAC TCC TCT CCA CCA GTA GTG CCC CAG AGC TTC CAG GTG GCT 220                                         230
  H   L   H   A   P   T   G   S   G   K   S   T   K   V   P   A   A   Y   A   A
  CAC CTC CAT GCT CCC ACA GGC AGC GGC AAA AGC ACC AAG GTC CCG GCT GCA TAT GCA GCT 240                                         250
  Q   G   Y   K   V   L   V   L   N   P   S   V   A   A   T   L   G   F   G   A
  CAG GGC TAT AAG GTG CTA GTA CTC AAC CCC TCT GTT GCT GCA ACA CTG GGC TTT GGT GCT 260                                         270
  Y   M   S   K   A   H   G   I   D   P   N   I   R   T   G   V   R   T   I   T
  TAC ATG TCC AAG GCT CAT GGG ATC GAT CCT AAC ATC AGG ACC GGG GTG AGA ACA ATT ACC
```

FIG. 7A

```
                        280                                                  290
 T   G   S   P   I   T   Y   S   T   Y   G   K   F   L   A   D   G   G   C   S
ACT GGC AGC CCC ATC ACG TAC TCC ACC TAC GGC AAG TTC CTT GCC GAC GGC GGG TGC TCG 300                                                  310
 G   G   A   Y   D   I   I   I   C   D   E   C   H   S   T   D   A   T   S   I
GGG GGC GCT TAT GAC ATA ATA ATT TGT GAC GAG TGC CAC TCC ACG GAT GCC ACA TCC ATC 320                                                  330
 L   G   I   G   T   V   L   D   Q   A   E   T   A   G   A   R   L   V   V   L
TTG GGC ATT GGC ACT GTC CTT GAC CAA GCA GAG ACT GCG GGG GCG AGA CTG GTT GTG CTC 340                                                  350
 A   T   A   T   P   P   G   S   V   T   V   P   H   P   N   I   E   E   V   A
GCC ACC GCC ACC CCT CCG GGC TCC GTC ACT GTG CCC CAT CCC AAC ATC GAG GAG GTT GCT 360                                                  370
 L   S   T   T   G   E   I   P   F   Y   G   K   A   I   P   L   E   V   I   K
CTG TCC ACC ACC GGA GAG ATC CCT TTT TAC GGC AAG GCT ATC CCC CTC GAA GTA ATC AAG 380                                                  390
 G   G   R   H   L   I   F   C   H   S   K   K   K   C   D   E   L   A   A   K
GGG GGG AGA CAT CTC ATC TTC TGT CAT TCA AAG AAG AAG TGC GAC GAA CTC GCC GCA AAG 400                                                  410
 L   V   A   L   G   I   N   A   V   A   Y   Y   R   G   L   D   V   S   V   I
CTG GTC GCA TTG GGC ATC AAT GCC GTG GCC TAC TAC CGC GGT CTT GAC GTG TCC GTC ATC 420                                                  430
 P   P   I   G   D   V   V   V   V   A   T   D   A   L   M   T   G   Y   T   G
CCG CCC ATC GGC GAT GTT GTC GTC GTG GCA ACC GAT GCC CTC ATG ACC GGC TAT ACC GGC 440                                                  450
 D   F   D   S   V   I   D   C   N   T   C   V   T   Q   T   V   D   F   S   L
GAC TTC GAC TCG GTG ATA GAC TGC AAT ACG TGT GTC ACC CAG ACA GTC GAT TTC AGC CTT 460                                                  470
 D   P   T   F   T   I   E   T   I   T   L   P   Q   D   A   V   S   R   T   Q
GAC CCT ACC TTC ACC ATT GAG ACA ATC ACG CTC CCC CAA GAT GCT GTC TCC CGC ACT CAA 480                                                  490
 R   R   G   R   T   G   R   G   K   P   G   I   Y   R   F   V   A   P   G   E
CGT CGG GGC AGG ACT GGC AGG GGG AAG CCA GGC ATC TAC AGA TTT GTG GCA CCG GGG GAG 500                                                  510
 R   P   S   G   M   F   D   S   S   V   L   C   E   C   Y   D   A   G   C   A
CGC CCC TCC GGC ATG TTC GAC TCG TCC GTC CTC TGT GAG TGC TAT GAC GCA GGC TGT GCT 520                                                  530
 W   Y   E   L   T   P   A   E   T   T   V   R   L   R   A   Y   M   N   T   P
TGG TAT GAG CTC ACG CCC GCC GAG ACT ACA GTT AGG CTA CGA GCG TAC ATG AAC ACC CCG 540                                                  550
 G   L   P   V   C   Q   D   H   L   E   F   W   E   G   V   F   T   G   L   T
GGG CTT CCC GTG TGC CAG GAC CAT CTT GAA TTT TGG GAG GGC GTC TTT ACA GGC CTC ACT 560                                                  570
 H   I   D   A   H   F   L   S   Q   T   K   Q   S   G   E   N   L   P   Y   L
CAT ATA GAT GCC CAC TTT CTA TCC CAG ACA AAG CAG AGT GGG GAG AAC CTT CCT TAC CTG
```

FIG. 7B

```
              580                                              590
 V   A   Y   Q   A   T   V   C   A   R   A   Q   A   P   P   P   S   W   D   Q
GTA GCG TAC CAA GCC ACC GTG TGC GCT AGG GCT CAA GCC CCT CCC CCA TCG TGG GAC CAG 600                                              610
 M   W   K   C   L   I   R   L   K   P   T   L   H   G   P   T   P   L   L   Y
ATG TGG AAG TGT TTG ATT CGC CTC AAG CCC ACC CTC CAT GGG CCA ACA CCC CTG CTA TAC 620                                              630
 R   L   G   A   V   Q   N   E   I   T   L   T   H   P   V   T   K   Y   I   M
AGA CTG GGC GCT GTT CAG AAT GAA ATC ACC CTG ACG CAC CCA GTC ACC AAA TAC ATC ATG 640                    646
 T   C   M   S   A   D   L   E   V   V   T   OP
ACA TGC ATG TCG GCC GAC CTG GAG GTC GTC ACG TGA
```

FIG. 7C

```
  1                                           10
  M   A   T   K   A   V   C   V   L   K   G   D   G   P   V
ATG GCT ACA AAG GCT GTT TGT GTT TTG AAG GGT GAC GGC CCA GTT 20                                  30
  Q   G   I   I   N   F   E   Q   K   E   S   N   G   P   V
CAA GGT ATT ATT AAC TTC GAG CAG AAG GAA AGT AAT GGA CCA GTG

40
  K   V   W   G   S   I   K   G   L   T   E   G   L   H   G
AAG GTG TGG GGA AGC ATT AAA GGA CTG ACT GAA GGC CTG CAT GGA 50                                  60
  F   H   V   H   E   F   G   D   N   T   A   G   C   T   S
TTC CAT GTT CAT GAG TTT GGA GAT AAT ACA GCA GGC TGT ACC AGT

70
  A   G   P   H   F   N   P   L   S   R   K   H   G   G   P
GCA GGT CCT CAC TTT AAT CCT CTA TCC AGA AAA CAC GGT GGG CCA 80                                  90
  K   D   E   E   R   H   V   G   D   L   G   N   V   T   A
AAG GAT GAA GAG AGG CAT GTT GGA GAC TTG GGC AAT GTG ACT GCT

100
  D   K   D   G   V   A   D   V   S   I   E   D   S   V   I
GAC AAA GAT GGT GTG GCC GAT GTG TCT ATT GAA GAT TCT GTG ATC 110                                 120
  S   L   S   G   D   H   C   I   I   G   R   T   L   V   V
TCA CTC TCA GGA GAC CAT TGC ATC ATT GGC CGC ACA CTG GTG GTC

130
  H   E   K   A   D   D   L   G   K   G   G   N   E   E   S
CAT GAA AAA GCA GAT GAC TTG GGC AAA GGT GGA AAT GAA GAA AGT 140                                 150
  T   K   T   G   N   A   G   S   R   L   A   C   G   V   I
ACA AAG ACA GGA AAC GCT GGA AGT CGT TTG GCT TGT GGT GTA ATT

160
  G   I   A   Q   N   L   N   S   G   C   N   C   S   I   Y
GGG ATC GCC CAG AAT TTG AAT TCT GGT TGC AAT TGC TCT ATC TAT 170                                 180
  P   G   H   I   T   G   H   R   M   A   W   K   L   G   S
CCC GGC CAT ATA ACG GGT CAC CGC ATG GCA TGG AAG CTT GGT TCC

190
  A   A   R   T   T   S   G   F   V   S   L   F   A   P   G
GCC GCC AGA ACT ACC TCG GGC TTT GTC TCC TTG TTC GCC CCA GGT
```

FIG. 9A

```
              200                                              210
 A   K   Q   N   E   T   H   V   T   G   G   A   A   A   R
GCC AAA CAA AAC GAA ACT CAC GTC ACG GGA GGC GCA GCC GCC CGA

220
 T   T   S   G   L   T   S   L   F   S   P   G   A   S   Q
ACT ACG TCT GGG TTG ACC TCT TTG TTC TCC CCA GGT GCC AGC CAA 230                                              240
 N   I   Q   L   I   V   D   F   I   P   V   E   N   L   E
AAC ATT CAA TTG ATT GTC GAC TTT ATC CCT GTG GAG AAC CTA GAG

250
 T   T   M   R   S   P   V   F   T   D   N   S   S   P   P
ACA ACC ATG CGA TCT CCG GTG TTC ACG GAT AAC TCC TCT CCA CCA 260                                              270
 V   V   P   Q   S   F   Q   V   A   H   L   H   A   P   T
GTA GTG CCC CAG AGC TTC CAG GTG GCT CAC CTC CAT GCT CCC ACA

280
 G   S   G   K   S   T   K   V   P   A   A   Y   A   A   Q
GGC AGC GGC AAA AGC ACC AAG GTC CCG GCT GCA TAT GCA GCT CAG 290                                              300
 G   Y   K   V   L   V   L   N   P   S   V   A   A   T   L
GGC TAT AAG GTG CTA GTA CTC AAC CCC TCT GTT GCT GCA ACA CTG

310
 G   F   G   A   Y   M   S   K   A   H   G   I   D   P   N
GGC TTT GGT GCT TAC ATG TCC AAG GCT CAT GGG ATC GAT CCT AAC 320                                              330
 I   R   T   G   V   R   T   I   T   T   G   S   P   I   T
ATC AGG ACC GGG GTG AGA ACA ATT ACC ACT GGC AGC CCC ATC ACG

340
 Y   S   T   Y   G   K   F   L   A   D   G   G   C   S   G
TAC TCC ACC TAC GGC AAG TTC CTT GCC GAC GGC GGG TGC TCG GGG 350                                              360
 G   A   Y   D   I   I   I   C   D   E   C   H   S   T   D
GGC GCT TAT GAC ATA ATA ATT TGT GAC GAG TGC CAC TCC ACG GAT

370
 A   T   S   I   L   G   I   G   T   V   L   D   Q   A   E
GCC ACA TCC ATC TTG GGC ATT GGC ACT GTC CTT GAC CAA GCA GAG 380                                              390
 T   A   G   A   R   L   V   V   L   A   T   A   T   P   P
ACT GCG GGG GCG AGA CTG GTT GTG CTC GCC ACC GCC ACC CCT CCG
```

FIG. 9B

```
                                           400
       G   S   V   T   V   P   H   P   N   I   E   E   V   A   L
      GGC TCC GTC ACT GTG CCC CAT CCC AAC ATC GAG GAG GTT GCT CTG 410                                          420
       S   T   T   G   E   I   P   F   Y   G   K   A   I   P   L
      TCC ACC ACC GGA GAG ATC CCT TTT TAC GGC AAG GCT ATC CCC CTC

430
       E   V   I   K   G   G   R   H   L   I   F   C   H   S   K
      GAA GTA ATC AAG GGG GGG AGA CAT CTC ATC TTC TGT CAT TCA AAG 440                                          450
       K   K   C   D   E   L   A   A   K   L   V   A   L   G   I
      AAG AAG TGC GAC GAA CTC GCC GCA AAG CTG GTC GCA TTG GGC ATC

460
       N   A   V   A   Y   Y   R   G   L   D   V   S   V   I   P
      AAT GCC GTG GCC TAC TAC CGC GGT CTT GAC GTG TCC GTC ATC CCG 470                                          480
       T   S   G   D   V   V   V   V   A   T   D   A   L   M   T
      ACC AGC GGC GAT GTT GTC GTC GTG GCA ACC GAT GCC CTC ATG ACC

490
       G   Y   T   G   D   F   D   S   V   I   D   C   N   T   C
      GGC TAT ACC GGC GAC TTC GAC TCG GTG ATA GAC TGC AAT ACG TGT 500                                          510
       V   T   Q   T   V   D   F   S   L   D   P   T   F   T   I
      GTC ACC CAG ACA GTC GAT TTC AGC CTT GAC CCT ACC TTC ACC ATT

520
       E   T   I   T   L   P   Q   D   A   V   S   R   T   Q   R
      GAG ACA ATC ACG CTC CCC CAA GAT GCT GTC TCC CGC ACT CAA CGT 530                                          540
       R   G   R   T   G   R   G   K   P   G   I   Y   R   F   V
      CGG GGC AGG ACT GGC AGG GGG AAG CCA GGC ATC TAC AGA TTT GTG

550
       A   P   G   E   R   P   S   G   M   F   D   S   S   V   L
      GCA CCG GGG GAG CGC CCC TCC GGC ATG TTC GAC TCG TCC GTC CTC 560                                          570
       C   E   C   Y   D   A   G   C   A   W   Y   E   L   T   P
      TGT GAG TGC TAT GAC GCA GGC TGT GCT TGG TAT GAG CTC ACG CCC

580
       A   E   T   T   V   R   L   R   A   Y   M   N   T   P   G
      GCC GAG ACT ACA GTT AGG CTA CGA GCG TAC ATG AAC ACC CCG GGG
```

FIG. 9C

```
                    590                                                600
     L    P    V    C    Q    D    H    L    E    F    W    E    G    V    F
    CTT  CCC  GTG  TGC  CAG  GAC  CAT  CTT  GAA  TTT  TGG  GAG  GGC  GTC  TTT

610
     T    G    L    T    H    I    D    A    H    F    L    S    Q    T    K
    ACA  GGC  CTC  ACT  CAT  ATA  GAT  GCC  CAC  TTT  CTA  TCC  CAG  ACA  AAG 620                                                630
     Q    S    G    E    N    L    P    Y    L    V    A    Y    Q    A    T
    CAG  AGT  GGG  GAG  AAC  CTT  CCT  TAC  CTG  GTA  GCG  TAC  CAA  GCC  ACC

640
     V    C    A    R    A    Q    A    P    P    P    S    W    D    Q    M
    GTG  TGC  GCT  AGG  GCT  CAA  GCC  CCT  CCC  CCA  TCG  TGG  GAC  CAG  ATG 650                                                660
     W    K    C    L    I    R    L    K    P    T    L    H    G    P    T
    TGG  AAG  TGT  TTG  ATT  CGC  CTC  AAG  CCC  ACC  CTC  CAT  GGG  CCA  ACA

670
     P    L    L    Y    R    L    G    A    V    Q    N    E    I    T    L
    CCC  CTG  CTA  TAC  AGA  CTG  GGC  GCT  GTT  CAG  AAT  GAA  ATC  ACC  CTG 680                                                690
     T    H    P    V    T    K    Y    I    M    T    C    M    S    A    D
    ACG  CAC  CCA  GTC  ACC  AAA  TAC  ATC  ATG  ACA  TGC  ATG  TCG  GCC  GAC

700
     L    E    V    V    T    S    A    C    S    G    K    P    A    I    I
    CTG  GAG  GTC  GTC  ACG  AGC  GCA  TGC  TCC  GGG  AAG  CCG  GCA  ATC  ATA 710                                                720
     P    D    R    E    V    L    Y    R    E    F    D    E    M    E    E
    CCT  GAC  AGG  GAA  GTC  CTC  TAC  CGA  GAG  TTC  GAT  GAG  ATG  GAA  GAG

730
     C    S    Q    H    L    P    Y    I    E    Q    G    M    M    L    A
    TGC  TCT  CAG  CAC  TTA  CCG  TAC  ATC  GAG  CAA  GGG  ATG  ATG  CTC  GCC 740                                                750
     E    Q    F    K    Q    K    A    L    G    L    S    R    G    G    K
    GAG  CAG  TTC  AAG  CAG  AAG  GCC  CTC  GGC  CTC  TCG  CGA  GGG  GGC  AAG

760
     P    A    I    V    P    D    K    E    V    L    Y    Q    Q    Y    D
    CCG  GCA  ATC  GTT  CCA  GAC  AAA  GAG  GTG  TTG  TAT  CAA  CAA  TAC  GAT 770                                                780
     E    M    E    E    C    S    Q    A    A    P    Y    I    E    Q    A
    GAG  ATG  GAA  GAG  TGC  TCA  CAA  GCT  GCC  CCA  TAT  ATC  GAA  CAA  GCT
```

FIG. 9D

```
                                        790
      Q   V   I   A   H   Q   F   K   E   K   V   L   G   L   I
      CAG GTA ATA GCT CAC CAG TTC AAG GAA AAA GTC CTT GGA TTG ATC 800                                   810
      D   N   D   Q   V   V   V   T   P   D   K   E   I   L   Y
      GAT AAT GAT CAA GTG GTT GTG ACT CCT GAC AAA GAA ATC TTA TAT

820
      E   A   F   D   E   M   E   E   C   A   S   K   A   A   L
      GAG GCC TTT GAT GAG ATG GAA GAA TGC GCC TCC AAA GCC GCC CTC 830                                   840
      I   E   E   G   Q   R   M   A   E   M   L   K   S   K   I
      ATT GAG GAA GGG CAG CGG ATG GCG GAG ATG CTC AAG TCT AAG ATA

850
      Q   G   L   L   G   I   L   R   R   H   V   G   P   G   E
      CAA GGC CTC CTC GGG ATA CTG CGC CGG CAC GTT GGT CCT GGC GAG 860                           870
      G   A   V   Q   W   M   N   R   L   I   A   F   A   S   R
      GGG GCA GTG CAG TGG ATG AAC CGG CTG ATA GCC TTC GCC TCC AGA

880
      G   N   H   V   S   P   T   H   Y   V   P   S   R   S   R
      GGG AAC CAT GTT TCC CCC ACG CAC TAC GTT CCG TCT AGA TCC CGG 890                           900
      R   F   A   Q   A   L   P   V   W   A   R   P   D   Y   N
      AGA TTC GCC CAG GCC CTG CCC GTT TGG GCG CGG CCG GAC TAT AAC

910
      P   P   L   V   E   T   W   K   K   P   D   Y   E   P   P
      CCC CCG CTA GTG GAG ACG TGG AAA AAG CCC GAC TAC GAA CCA CCT 920                                   930
      V   V   H   G   R   S   S   R   R   F   A   Q   A   L   P
      GTG GTC CAC GGC AGA TCT TCT CGG AGA TTC GCC CAG GCC CTG CCC

940
      V   W   A   R   P   D   Y   N   P   P   L   V   E   T   W
      GTT TGG GCG CGG CCG GAC TAT AAC CCC CCG CTA GTG GAG ACG TGG 950                                   960
      K   K   P   D   Y   E   P   P   V   V   H   G   R   K   T
      AAA AAG CCC GAC TAC GAA CCA CCT GTG GTC CAT GGC AGA AAG ACC

970
      K   R   N   T   N   R   R   P   Q   D   V   K   F   P   G
      AAA CGT AAC ACC AAC CGG CGG CCG CAG GAC GTC AAG TTC CCG GGT
```

FIG. 9E

```
                                     980                                              990
         G    G    Q    I    V    G    R    R    G    P    P    I    P    K    A
        GGC  GGT  CAG  ATC  GTT  GGT  CGC  AGG  GGC  CCT  CCT  ATC  CCC  AAG  GCT

1000
         R    R    P    E    G    R    T    W    A    Q    P    G    Y    P    W
        CGT  CGG  CCC  GAG  GGC  AGG  ACC  TGG  GCT  CAG  CCC  GGT  TAC  CCT  TGG 1010                                                      1020
         P    L    Y    G    N    K    D    R    R    S    T    G    K    S    W
        CCC  CTC  TAT  GGC  AAT  AAG  GAC  AGA  CGG  TCT  ACA  GGT  AAG  TCC  TGG

1030
         G    K    P    G    Y    P    W    P    R    K    T    K    R    N    T
        GGT  AAG  CCA  GGG  TAC  CCT  TGG  CCA  AGA  AAG  ACC  AAA  CGT  AAC  ACC 1040                                                 1050
         N    R    R    P    Q    D    V    K    F    P    G    G    G    Q    I
        AAC  CGA  CGG  CCG  CAG  GAC  GTC  AAG  TTC  CCG  GGT  GGC  GGT  CAG  ATC

1060
         V    G    R    R    G    P    P    I    P    K    A    R    R    P    E
        GTT  GGT  CGC  AGG  GGC  CCT  CCT  ATC  CCC  AAG  GCT  CGT  CGG  CCC  GAG 1070                                            1080
         G    R    T    W    A    Q    P    G    Y    P    W    P    L    Y    G
        GGC  AGG  ACC  TGG  GCT  CAG  CCC  GGT  TAC  CCT  TGG  CCC  CTC  TAT  GGC

1090
         N    K    D    R    R    S    T    G    K    S    W    G    K    P    G
        AAT  AAG  GAC  AGA  CGG  TCT  ACC  GGT  AAG  TCC  TGG  GGT  AAG  CCA  GGG

1099
         Y    P    W    P
        TAT  CCT  TGG  CCC
```

FIG. 9F

MEFA-3 ANTIGEN

| hSOD-(1-154) | CORE | CORE | c33c | 5-1-1 type 1 | 5-1-1 type 3 | 5-1-1 type 2 | C-100 | C-100 | NS5 | NS5 |
|---|---|---|---|---|---|---|---|---|---|---|
| AMINO ACIDS | 10 - 53 | 10 - 53 | 1192 - 1457 | 1694 - 1735 | 1694 - 1735 | 1694 - 1735 | 1901 - 1940 | 1901 - 1940 | 2278 - 2310 | 2278 - 2310 |

FIG. 11A

MEFA-5 ANTIGEN

| hSOD-(1-154) | CORE | E1 | E2 | c33c | 5-1-1 type 1 | 5-1-1 type 3 | 5-1-1 type 2 | C-100 | NS5 | NS5 |
|---|---|---|---|---|---|---|---|---|---|---|
| AMINO ACIDS | 10 - 53 | 303 - 320 | 405 - 444 | 1192 - 1457 | 1689 - 1735 | 1689 - 1735 | 1689 - 1735 | 1901 - 1940 | 2278 - 2313 | 2278 - 2313 |

FIG. 11B

MEFA-6 ANTIGEN

| hSOD-(1-154) | E1 | E2 | c33c | 5-1-1 type 1 | 5-1-1 type 3 | 5-1-1 type 2 | C-100 | NS5 | NS5 | CORE | CORE |
|---|---|---|---|---|---|---|---|---|---|---|---|
| AMINO ACIDS | 303 - 320 | 405 - 444 | 1192 - 1457 | 1689 - 1735 | 1689 - 1735 | 1689 - 1735 | 1901 - 1940 | 2278 - 2313 | 2278 - 2313 | 10 - 53 | 10 - 53 |

FIG 11C

SEQUENCE LISTING

```
<160> NUMBER OF SEQ ID NOS: 33

<210> SEQ ID NO 1
<211> LENGTH: 2061
<212> TYPE: DNA
<213> ORGANISM: Artificial
<220> FEATURE:
<223> OTHER INFORMATION: NS34aPI.1165

<400> SEQUENCE: 1
atggcgccca tcacggcgta cgcccagcag acaaggggcc tcctagggtg cataatcacc      60
agcctaactg gccgggacaa aaaccaagtg gagggtgagg tccagattgt gtcaactgct     120
gcccaaacct tcctggcaac gtgcatcaat ggggtgtgct ggactgtcta ccacggggcc     180
ggaacgagga ccatcgcgtc acccaagggt cctgtcatcc agatgtatac caatgtagac     240
caagaccttg tgggctggcc cgctccgcaa ggtagccgat cattgacacc ctgcacttgc     300
ggctcctcgg acctttacct ggtcacgagg cacgccgatg tcattcccgt gcgccggcgg     360
ggtgatagca ggggcagcct gctgtcgccc cggcccattt cctacttgaa aggctccgca     420
gggggtccgc tgttgtgccc cgcggggcac gccgtgggca tatttagggc cgcggtgtgc     480
acccgtggag tggctaaggc ggtggacttt atccctgtgg agaacctaga gacaaccatg     540
aggtccccgg tgttcacgga taactcctct ccaccagtag tgccccagag cttccaggtg     600
gctcacctcc atgctcccac aggcagcggc aaaagcacca aggtcccggc tgcatatgca     660
gctcagggct ataaggtgct agtactcaac ccctctgttg ctgcaacact gggctttggt     720
gcttacatgt ccaaggctca tgggatcgat cctaacatca ggaccggggt gagaacaatt     780
accactggca gccccatcac gtactccacc tacggcaagt tccttgccga cggcgggtgc     840
tcggggggcg cttatgacat aataatttgt gacgagtgcc actccacgga tgccacatcc     900
atcttgggca ttggcactgt ccttgaccaa gcagagactg cgggggcgag actggttgtg     960
ctcgccaccg ccacccctcc gggctccgtc actgtgcccc atcccaacat cgaggaggtt    1020
gctctgtcca ccaccggaga gatccctttt tacggcaagg ctatccccct cgaagtaatc    1080
aaggggggga gacatctcat cttctgtcat tcaaagaaga agtgcgacga actcgccgca    1140
aagctggtcg cattgggcat caatgccgtg gcctactacc gcggtcttga cgtgtccgtc    1200
atcccgccca tcggcgatgt tgtcgtcgtg gcaaccgatg ccctcatgac cggctatacc    1260
```

-continued

```
ggcgacttcg actcggtgat agactgcaat acgtgtgtca cccagacagt cgatttcagc    1320
cttgacccta ccttcaccat tgagacaatc acgctccccc aagatgctgt ctcccgcact    1380
caacgtcggg gcaggactgg caggggaag ccaggcatct acagatttgt ggcaccgggg    1440
gagcgcccct ccggcatgtt cgactcgtcc gtcctctgtg agtgctatga cgcaggctgt    1500
gcttggtatg agctcacgcc cgccgagact acagttaggc tacgagcgta catgaacacc    1560
ccggggcttc ccgtgtgcca ggaccatctt gaattttggg agggcgtctt tacaggcctc    1620
actcatatag atgcccactt tctatcccag acaaagcaga gtggggagaa ccttccttac    1680
ctggtagcgt accaagccac cgtgtgcgct agggctcaag cccctccccc atcgtgggac    1740
cagatgtgga agtgtttgat tcgcctcaag cccaccctcc atgggccaac ccccctgcta    1800
tacagactgg gcgctgttca gaatgaaatc accctgacgc acccagtcac caaatacatc    1860
atgacatgca tgtcggccga cctggaggtc gtcacgagca cctgggtgct cgttggcggc    1920
gtcctggctg ctttggccgc gtattgcctg tcaacaggct gcgtggtcat agtgggcagg    1980
gtcgtcttgt ccgggaagcc ggcaatcata cctgacaggg aagtcctcta ccgagagttc    2040
gatgagatgg aagagtgctg a                                              2061
```

<210> SEQ ID NO 2
<211> LENGTH: 686
<212> TYPE: PRT
<213> ORGANISM: Artificial
<220> FEATURE:
<223> OTHER INFORMATION: NS34aPI.1165

<400> SEQUENCE: 2

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ser Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ala Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
```

-continued

```
            210                 215                 220
Lys Val Leu Val Leu Asn Pro Ser Val Ala Thr Leu Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ser Pro Ile Thr Tyr Ser Thr Tyr Gly
                260                 265                 270
Lys Phe Leu Ala Asp Gly Gly Cys Ser Gly Gly Ala Tyr Asp Ile Ile
                275                 280                 285
Ile Cys Asp Glu Cys His Ser Thr Asp Ala Thr Ser Ile Leu Gly Ile
290                 295                 300
Gly Thr Val Leu Asp Gln Ala Glu Thr Ala Gly Ala Arg Leu Val Val
305                 310                 315                 320
Leu Ala Thr Ala Thr Pro Pro Gly Ser Val Thr Val Pro His Pro Asn
                325                 330                 335
Ile Glu Glu Val Ala Leu Ser Thr Thr Gly Glu Ile Pro Phe Tyr Gly
                340                 345                 350
Lys Ala Ile Pro Leu Glu Val Ile Lys Gly Gly Arg His Leu Ile Phe
                355                 360                 365
Cys His Ser Lys Lys Lys Cys Asp Glu Leu Ala Ala Lys Leu Val Ala
                370                 375                 380
Leu Gly Ile Asn Ala Val Ala Tyr Tyr Arg Gly Leu Asp Val Ser Val
385                 390                 395                 400
Ile Pro Pro Ile Gly Asp Val Val Val Ala Thr Asp Ala Leu Met
                405                 410                 415
Thr Gly Tyr Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
                435                 440                 445
Thr Ile Thr Leu Pro Gln Asp Ala Val Ser Arg Thr Gln Arg Arg Gly
                450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
                500                 505                 510
Arg Leu Arg Ala Tyr Met Asn Thr Pro Gly Leu Pro Val Cys Gln Asp
                515                 520                 525
His Leu Glu Phe Trp Glu Gly Val Phe Thr Gly Leu Thr His Ile Asp
                530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
                580                 585                 590
Leu His Gly Pro Thr Pro Leu Leu Tyr Arg Leu Gly Ala Val Gln Asn
                595                 600                 605
Glu Ile Thr Leu Thr His Pro Val Thr Lys Tyr Ile Met Thr Cys Met
                610                 615                 620
Ser Ala Asp Leu Glu Val Val Thr Ser Thr Trp Val Leu Val Gly Gly
625                 630                 635                 640
```

```
Val Leu Ala Ala Leu Ala Ala Tyr Cys Leu Ser Thr Gly Cys Val Val
                645                 650                 655

Ile Val Gly Arg Val Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 3
<211> LENGTH: 1899
<212> TYPE: DNA
<213> ORGANISM: Artificial
<220> FEATURE:
<223> OTHER INFORMATION: NS3PI.1165

<400> SEQUENCE: 3
atggcgccaa tcactgctta cgctcaacaa accagaggcc tcctagggtg cataatcacc      60
agcctaactg gccgggacaa aaaccaagtg gagggtgagg tccagattgt gtcaactgct     120
gcccaaacct tcctggcaac gtgcatcaat ggggtgtgct ggactgtcta ccacggggcc     180
ggaacgagga ccatcgcgtc acccaagggt cctgtcatcc agatgtatac caatgtagac     240
caagaccttg tgggctggcc cgctccgcaa ggtagccgat cattgacacc ctgcacttgc     300
ggctcctcgg acctttacct ggtcacgagg cacgccgatg tcattcccgt gcgccggcgg     360
ggtgatagca ggggcagcct gctgtcgccc cggcccattt cctacttgaa aggctccgca     420
gggggtccgc tgttgtgccc cgcggggcac gccgtgggca tatttaggtgc gcggtgtgc     480
acccgtggag tggctaaggc ggtggacttt atccctgtgg agaacctaga caaccatg      540
aggtccccgg tgttcacgga taactcctct ccaccagtag tgccccagag cttccaggtg     600
gctcacctcc atgctcccac aggcagcggc aaaagcacca aggtcccggc tgcatatgca     660
gctcagggct ataaggtgct agtactcaac ccctctgttg ctgcaacact gggctttggt     720
gcttacatgt ccaaggctca tgggatcgat cctaacatca ggaccggggt gagaacaatt     780
accactggca gccccatcac gtactccacc tacggcaagt tccttgccga cggcgggtgc     840
tcggggggcg cttatgacat aataaatttgt gacgagtgcc actccacgga tgccacatcc     900
atcttgggca ttggcactgt cctttgaccaa gcagagactg cggggcgag actggttgtg     960
ctcgccaccg ccaccccctc gggctccgtc actgtgcccc atcccaacat cgaggaggtt    1020
gctctgtcca ccaccggaga gatccctttt tacggcaagg ctatccccct cgaagtaatc    1080
aagggggga gacatctcat cttctgtcat tcaaagaaga gtgcgacga actcgccgca    1140
aagctggtcg cattgggcat caatgccgtg cctactaccc gcggtcttga cgtgtccgtc    1200
atcccgcca tcggcgatgt tgtcgtcgtg gcaaccgatg ccctcatgac cggctatacc    1260
ggcgacttcg actcggtgat agactgcaat acgtgtgtca cccagacagt cgatttcagc    1320
cttgacccta ccttcaccat tgagacaatc acgctccccc aagatgctgt ctcccgcact    1380
caacgtcggg gcaggactgg caggggaag ccaggcatct acagatttgt ggcaccgggg    1440
gagcgcccct ccggcatgtt cgactcgtcc gtcctctgtg agtgctatga cgcaggctgt    1500
gcttggtatg agctcacgcc cgccgagact acagttaggc tacgagcgta catgaacacc    1560
ccggggcttc ccgtgtgcca ggaccatctt gaattttggg agggcgtctt acaggcctc    1620
actcatatag atgcccactt tctatcccag acaaagcaga gtggggagaa ccttccttac    1680
ctggtagcgt accagccac cgtgtgcgct agggctcaag ccctcccccc atcgtgggac    1740
cagatgtgga agtgtttgat tcgcctcaag cccaccctcc atgggccaac accctgcta    1800
```

```
tacagactgg gcgctgttca gaatgaaatc accctgacgc acccagtcac caaatacatc   1860
atgacatgca tgtcggccga cctggaggtc gtcacgtga                          1899
```

<210> SEQ ID NO 4
<211> LENGTH: 632
<212> TYPE: PRT
<213> ORGANISM: Artificial
<220> FEATURE:
<223> OTHER INFORMATION: NS3PI.1165

<400> SEQUENCE: 4

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ser Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ala Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
```

-continued

```
                     340                 345                 350
Lys Ala Ile Pro Leu Glu Val Ile Lys Gly Gly Arg His Leu Ile Phe
            355                 360                 365
Cys His Ser Lys Lys Cys Asp Glu Leu Ala Ala Lys Leu Val Ala
        370                 375                 380
Leu Gly Ile Asn Ala Val Ala Tyr Tyr Arg Gly Leu Asp Val Ser Val
385                 390                 395                 400
Ile Pro Pro Ile Gly Asp Val Val Val Ala Thr Asp Ala Leu Met
                405                 410                 415
Thr Gly Tyr Thr Gly Asp Phe Asp Ser Val Ile Asp Cys Asn Thr Cys
            420                 425                 430
Val Thr Gln Thr Val Asp Phe Ser Leu Asp Pro Thr Phe Thr Ile Glu
        435                 440                 445
Thr Ile Thr Leu Pro Gln Asp Ala Val Ser Arg Thr Gln Arg Gly
            450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
            500                 505                 510
Arg Leu Arg Ala Tyr Met Asn Thr Pro Gly Leu Pro Val Cys Gln Asp
        515                 520                 525
His Leu Glu Phe Trp Glu Gly Val Phe Thr Gly Leu Thr His Ile Asp
            530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
        595                 600                 605
Glu Ile Thr Leu Thr His Pro Val Thr Lys Tyr Ile Met Thr Cys Met
    610                 615                 620
Ser Ala Asp Leu Glu Val Val Thr
625                 630
```

<210> SEQ ID NO 5
<211> LENGTH: 1941
<212> TYPE: DNA
<213> ORGANISM: Artificial
<220> FEATURE:
<223> OTHER INFORMATION: d.4a.t.NS3PI.1165

<400> SEQUENCE: 5

| | | | | | |
|---|---|---|---|---|---|
| atgggctgcg | tggtcatagt | gggcagggtc | gtcttgtccg | gttccggttc | catcactgct | 60 |
| tacgctcaac | aaaccagagg | cctcctaggg | tgcataatca | ccagcctaac | tggccgggac | 120 |
| aaaaaccaag | tggagggtga | ggtccagatt | gtgtcaactg | ctgcccaaac | cttcctggca | 180 |
| acgtgcatca | atgggtgtgt | ctggactgtc | taccacgggg | ccggaacgag | gaccatcgcg | 240 |
| tcacccaagg | gtcctgtcat | ccagatgtat | accaatgtag | accaagacct | tgtgggctgg | 300 |
| cccgctccgc | aaggtagccg | atcattgaca | ccctgcactt | gcggctcctc | ggaccttac | 360 |
| ctggtcacga | ggcacgccga | tgtcattccc | gtgcgccggc | ggggtgatag | cagggcagc | 420 |

-continued

```
ctgctgtcgc cccggcccat ttcctacttg aaaggctccg cagggggtcc gctgttgtgc    480
cccgcgggc acgccgtggg catatttagg gccgcggtgt gcacccgtgg agtggctaag     540
gcggtggact ttatccctgt ggagaaccta gagacaacca tgaggtcccc ggtgttcacg    600
gataactcct ctccaccagt agtgccccag agcttccagg tggctcacct ccatgctccc    660
acaggcagcg gcaaaagcac caaggtcccg gctgcatatg cagctcaggg ctataaggtg    720
ctagtactca accctctgt tgctgcaaca ctgggctttg gtgcttacat gtccaaggct     780
catgggatcg atcctaacat caggaccggg gtgagaacaa ttaccactgg cagccccatc    840
acgtactcca cctacggcaa gttccttgcc gacggcgggt gctcgggggg cgcttatgac    900
ataataattt gtgacgagtg ccactccacg gatgccacat ccatcttggg cattggcact    960
gtccttgacc aagcagagac tgcggggggcg agactggttg tgctcgccac cgccacccct   1020
ccgggctccg tcactgtgcc ccatcccaac atcgaggagg ttgctctgtc caccaccgga   1080
gagatccctt tttacggcaa ggctatcccc ctcgaagtaa tcaaggggg gagacatctc    1140
atcttctgtc attcaaagaa gaagtgcgac gaactcgccg caaagctggt cgcattgggc   1200
atcaatgccg tggcctacta ccgcggtctt gacgtgtccg tcatcccgcc catcggcgat   1260
gttgtcgtcg tggcaaccga tgccctcatg accggctata ccggcgactt cgactcggtg   1320
atagactgca atacgtgtgt cacccagaca gtcgatttca gccttgaccc taccttcacc   1380
attgagacaa tcacgctccc ccaagatgct gtctcccgca ctcaacgtcg gggcaggact   1440
ggcaggggga agccaggcat ctacagattt gtggcaccgg gggagcgccc ctccggcatg   1500
ttcgactcgt ccgtcctctg tgagtgctat gacgcaggct gtgcttggta tgagctcacg   1560
cccgccgaga ctacagttag gctacgagcg tacatgaaca ccccgggggct cccgtgtgc   1620
caggaccatc ttgaattttg ggagggcgtc tttacaggcc tcactcatat agatgcccac   1680
tttctatccc agacaaagca gagtgggggag aaccttcctt acctggtagc gtaccaagcc   1740
accgtgtgcg ctagggctca gccccctccc catcgtgggg accagatgtg gaagtgtttg   1800
attcgcctca agcccaccct ccatgggcca acacccctgc tatacagact gggcgctgtt   1860
cagaatgaaa tcacctgac gcacccagtc accaaataca tcatgacatg catgtcggcc   1920
gacctggagg tcgtcacgtg a                                              1941
```

<210> SEQ ID NO 6
<211> LENGTH: 646
<212> TYPE: PRT
<213> ORGANISM: Artificial
<220> FEATURE:
<223> OTHER INFORMATION: d.4a.t.NS3PI.1165

<400> SEQUENCE: 6

Met Gly Cys Val Val Ile Val Gly Arg Val Val Leu Ser Gly Ser Gly
1               5                   10                  15

Ser Ile Thr Ala Tyr Ala Gln Gln Thr Arg Gly Leu Leu Gly Cys Ile
            20                  25                  30

Ile Thr Ser Leu Thr Gly Arg Asp Lys Asn Gln Val Glu Gly Glu Val
        35                  40                  45

Gln Ile Val Ser Thr Ala Ala Gln Thr Phe Leu Ala Thr Cys Ile Asn
    50                  55                  60

Gly Val Cys Trp Thr Val Tyr His Gly Ala Gly Thr Arg Thr Ile Ala
65                  70                  75                  80

-continued

```
Ser Pro Lys Gly Pro Val Ile Gln Met Tyr Thr Asn Val Asp Gln Asp
                85                  90                  95

Leu Val Gly Trp Pro Ala Pro Gln Gly Ser Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Gly Asp Ser Arg Gly Ser Leu Leu Ser Pro
130                 135                 140

Arg Pro Ile Ser Tyr Leu Lys Gly Ser Ala Gly Pro Leu Leu Cys
145                 150                 155                 160

Pro Ala Gly His Ala Val Gly Ile Phe Arg Ala Val Cys Thr Arg
            165                 170                 175

Gly Val Ala Lys Ala Val Asp Phe Ile Pro Val Glu Asn Leu Glu Thr
            180                 185                 190

Thr Met Arg Ser Pro Val Phe Thr Asp Asn Ser Ser Pro Pro Val Val
            195                 200                 205

Pro Gln Ser Phe Gln Val Ala His Leu His Ala Pro Thr Gly Ser Gly
            210                 215                 220

Lys Ser Thr Lys Val Pro Ala Ala Tyr Ala Ala Gln Gly Tyr Lys Val
225                 230                 235                 240

Leu Val Leu Asn Pro Ser Val Ala Ala Thr Leu Gly Phe Gly Ala Tyr
            245                 250                 255

Met Ser Lys Ala His Gly Ile Asp Pro Asn Ile Arg Thr Gly Val Arg
            260                 265                 270

Thr Ile Thr Thr Gly Ser Pro Ile Thr Tyr Ser Thr Tyr Gly Lys Phe
            275                 280                 285

Leu Ala Asp Gly Gly Cys Ser Gly Gly Ala Tyr Asp Ile Ile Ile Cys
            290                 295                 300

Asp Glu Cys His Ser Thr Asp Ala Thr Ser Ile Leu Gly Ile Gly Thr
305                 310                 315                 320

Val Leu Asp Gln Ala Glu Thr Ala Gly Ala Arg Leu Val Val Leu Ala
            325                 330                 335

Thr Ala Thr Pro Pro Gly Ser Val Thr Val Pro His Pro Asn Ile Glu
            340                 345                 350

Glu Val Ala Leu Ser Thr Thr Gly Glu Ile Pro Phe Tyr Gly Lys Ala
            355                 360                 365

Ile Pro Leu Glu Val Ile Lys Gly Gly Arg His Leu Ile Phe Cys His
            370                 375                 380

Ser Lys Lys Lys Cys Asp Glu Leu Ala Ala Lys Leu Val Ala Leu Gly
385                 390                 395                 400

Ile Asn Ala Val Ala Tyr Tyr Arg Gly Leu Asp Val Ser Val Ile Pro
            405                 410                 415

Pro Ile Gly Asp Val Val Val Ala Thr Asp Ala Leu Met Thr Gly
            420                 425                 430

Tyr Thr Gly Asp Phe Asp Ser Val Ile Asp Cys Asn Thr Cys Val Thr
            435                 440                 445

Gln Thr Val Asp Phe Ser Leu Asp Pro Thr Phe Thr Ile Glu Thr Ile
            450                 455                 460

Thr Leu Pro Gln Asp Ala Val Ser Arg Thr Gln Arg Arg Gly Arg Thr
465                 470                 475                 480

Gly Arg Gly Lys Pro Gly Ile Tyr Arg Phe Val Ala Pro Gly Glu Arg
            485                 490                 495
```

```
Pro Ser Gly Met Phe Asp Ser Ser Val Leu Cys Glu Cys Tyr Asp Ala
            500                 505                 510

Gly Cys Ala Trp Tyr Glu Leu Thr Pro Ala Glu Thr Thr Val Arg Leu
        515                 520                 525

Arg Ala Tyr Met Asn Thr Pro Gly Leu Pro Val Cys Gln Asp His Leu
    530                 535                 540

Glu Phe Trp Glu Gly Val Phe Thr Gly Leu Thr His Ile Asp Ala His
545                 550                 555                 560

Phe Leu Ser Gln Thr Lys Gln Ser Gly Glu Asn Leu Pro Tyr Leu Val
                565                 570                 575

Ala Tyr Gln Ala Thr Val Cys Ala Arg Ala Gln Ala Pro Pro Pro Ser
            580                 585                 590

Trp Asp Gln Met Trp Lys Cys Leu Ile Arg Leu Lys Pro Thr Leu His
        595                 600                 605

Gly Pro Thr Pro Leu Leu Tyr Arg Leu Gly Ala Val Gln Asn Glu Ile
    610                 615                 620

Thr Leu Thr His Pro Val Thr Lys Tyr Ile Met Thr Cys Met Ser Ala
625                 630                 635                 640

Asp Leu Glu Val Val Thr
                645

<210> SEQ ID NO 7
<211> LENGTH: 546
<212> TYPE: DNA
<213> ORGANISM: Artificial
<220> FEATURE:
<223> OTHER INFORMATION: native, unmodified NS3 protease domain

<400> SEQUENCE: 7
atggcgccca tcacggcgta cgcccagcag acaaggggcc tcctagggtg cataatcacc      60
agcctaactg gccgggacaa aaaccaagtg gagggtgagg tccagattgt gtcaactgct     120
gcccaaacct tcctggcaac gtgcatcaat ggggtgtgct ggactgtcta ccacggggcc     180
ggaacgagga ccatcgcgtc acccaagggt cctgtcatcc agatgtatac caatgtagac     240
caagaccttg tgggctggcc cgctccgcaa ggtagccgat cattgacacc ctgcacttgc     300
ggctcctcgg acctttacct ggtcacgagg cacgccgatg tcattcccgt cgcccggcgg     360
ggtgatagca ggggcagcct gctgtcgccc ggcccatttc ctacttgaa aggctcctcg      420 gggggtccgc tgttgtgccc cgcggggcac gccgtgggca tatttagggc gcggtgtgc     480 acccgtggag tggctaaggc ggtggacttt atccctgtgg agaacctaga cacaaccatg     540
aggtcc                                                                546

<210> SEQ ID NO 8
<211> LENGTH: 182
<212> TYPE: PRT
<213> ORGANISM: Artificial
<220> FEATURE:
<223> OTHER INFORMATION: native, unmodified NS3 protease domain

<400> SEQUENCE: 8

Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu Ala Thr Cys
            35                  40                  45
```

```
Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ser Arg Ser Leu Thr
                 85                  90                  95

Pro Cys Thr Cys Gly Ser Ser Asp Leu Tyr Leu Val Thr Arg His Ala
                100                 105                 110

Asp Val Ile Pro Val Arg Arg Arg Gly Asp Ser Arg Gly Ser Leu Leu
            115                 120                 125

Ser Pro Arg Pro Ile Ser Tyr Leu Lys Gly Ser Ser Gly Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser
                180
```

<210> SEQ ID NO 9
<211> LENGTH: 3297
<212> TYPE: DNA
<213> ORGANISM: Artificial
<220> FEATURE:
<223> OTHER INFORMATION: MEFA 7.1

<400> SEQUENCE: 9

```
atggctacaa aggctgtttg tgttttgaag ggtgacggcc cagttcaagg tattattaac      60
ttcgagcaga aggaaagtaa tggaccagtg aaggtgtggg gaagcattaa aggactgact     120
gaaggcctgc atggattcca tgttcatgag tttggagata atacagcagg ctgtaccagt     180
gcaggtcctc actttaatcc tctatccaga aaacacggtg gccaaaggga tgaagagagg     240
catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc agaatttgaa ttctggttgc     480
aattgctcta tctatcccgg ccatataacg ggtcaccgca tggcatggaa gcttggttcc     540
gccgccagaa ctacctcggg ctttgtctcc ttgttcgccc aggtgccaa acaaaacgaa     600
actcacgtca cgggaggcgc agccgcccga actacgtctg ggttgacctc tttgttctcc     660
ccaggtgcca gccaaaacat tcaattgatt gtcgacttta tccctgtgga gaacctagag     720
acaaccatgc gatctccggt gttcacggat aactcctctc caccagtagt gccccagagc     780
ttccaggtgg ctcacctcca tgctcccaca ggcagcggca aaagcaccaa ggtcccggct     840
gcatatgcag ctcagggcta aaggtgctaa gtactcaacc cctctgttgc tgcaacactg     900
ggctttggtg cttacatgtc caaggctcat gggatcgatc ctaacatcag gaccggggtg     960
agaacaatta ccactggcag ccccatcacg tactccacct acggcaagtt ccttgccgac    1020
ggcgggtgct cggggggcgc ttatgacata ataatttgtg acgagtgcca ctccacggat    1080
gccacatcca tcttgggcat tggcactgtc cttgaccaag cagagactgc gggggcgaga    1140
ctggttgtgc tcgccaccgc cacccctccg ggctccgtca ctgtgcccca tccaacatc    1200
gaggaggttg ctctgtccac caccggagag atcccttttt acggcaaggc tatccccctc    1260
```

-continued

```
gaagtaatca agggggggag acatctcatc ttctgtcatt caaagaagaa gtgcgacgaa    1320
ctcgccgcaa agctggtcgc attgggcatc aatgccgtgg cctactaccg cggtcttgac    1380
gtgtccgtca tcccgaccag cggcgatgtt gtcgtcgtgg caaccgatgc cctcatgacc    1440
ggctataccg gcgacttcga ctcggtgata gactgcaata cgtgtgtcac ccagacagtc    1500
gatttcagcc ttgaccctac cttcaccatt gagacaatca cgctccccca agatgctgtc    1560
tcccgcactc aacgtcgggg caggactggc aggggaagc caggcatcta cagatttgtg    1620
gcaccggggg agcgccctc cggcatgttc gactcgtccg tcctctgtga gtgctatgac    1680
gcaggctgtg cttggtatga gctcacgccc gccgagacta cagttaggct acgagcgtac    1740
atgaacaccc cggggcttcc cgtgtgccag gaccatcttg aattttggga gggcgtcttt    1800
acaggcctca ctcatataga tgcccacttt ctatcccaga caaagcagag tggggagaac    1860
cttccttacc tggtagcgta ccaagccacc gtgtgcgcta gggctcaagc ccctccccca    1920
tcgtgggacc agatgtggaa gtgtttgatt cgcctcaagc ccaccctcca tgggccaaca    1980
cccctgctat acagactggg cgctgttcag aatgaaatca ccctgacgca cccagtcacc    2040
aaatacatca tgacatgcat gtcggccgac ctggaggtcg tcacgagcgc atgctccggg    2100
aagccggcaa tcatacctga cagggaagtc ctctaccgag agttcgatga gatggaagag    2160
tgctctcagc acttaccgta catcgagcaa gggatgatgc tcgccgagca gttcaagcag    2220
aaggccctcg gcctctcgcg aggggggcaag ccggcaatcg ttccagacaa agaggtgttg    2280
tatcaacaat acgatgagat ggaagagtgc tcacaagctg ccccatatat cgaacaagct    2340
caggtaatag ctcaccagtt caaggaaaaa gtccttggat tgatcgataa tgatcaagtg    2400
gttgtgactc ctgacaaaga aatcttatat gaggcctttg atgagatgga agaatgcgcc    2460
tccaaagccg ccctcattga ggaagggcag cggatggcgg agatgctcaa gtctaagata    2520
caaggcctcc tcgggatact cgccggcac gttggtcctg gcgaggggc agtgcagtgg    2580 atgaaccggc tgatagcctt cgcctccaga gggaaccatg tttcccccac gcactacgtt    2640
ccgtctagat cccggagatt cgcccaggcc ctgcccgttt gggcgcggcc ggactataac    2700
cccccgctag tggagacgtg gaaaaagccc gactacgaac cacctgtggt ccacggcaga    2760
tcttctcgga gattcgccca ggccctgccc gtttgggcgc ggccggacta taacccccg    2820 ctagtggaga cgtggaaaaa gcccgactac gaaccacctg tggtccatgg cagaaagacc    2880
aaacgtaaca ccaaccggcg gccgcaggac gtcaagttcc cggtggcgg tcagatcgtt    2940 ggtcgcaggg gccctcctat ccccaaggct cgtcggcccg agggcaggac ctgggctcag    3000
cccggttacc cttggcccct ctatggcaat aaggacagac ggtctacagg taagtcctgg    3060
ggtaagccag ggtaccttg gccaagaaag accaaacgta acaccaaccg acggccgcag    3120
gacgtcaagt tcccgggtgg cggtcagatc gttggtcgca ggggccctcc tatccccaag    3180
gctcgtcggc ccgagggcag gacctgggct cagcccggtt acccttggcc cctctatggc    3240
aataaggaca gacggtctac cggtaagtcc tggggtaagc cagggtatcc ttggccc      3297
```

<210> SEQ ID NO 10
<211> LENGTH: 1099
<212> TYPE: PRT
<213> ORGANISM: Artificial
<220> FEATURE:
<223> OTHER INFORMATION: MEFA 7.1

<400> SEQUENCE: 10

Met Ala Thr Lys Ala Val Cys Val Leu Lys Gly Asp Gly Pro Val Gln

-continued

```
1               5                  10                 15
Gly Ile Ile Asn Phe Glu Gln Lys Glu Ser Asn Gly Pro Val Lys Val
                20                 25                 30
Trp Gly Ser Ile Lys Gly Leu Thr Glu Gly Leu His Gly Phe His Val
                35                 40                 45
His Glu Phe Gly Asp Asn Thr Ala Gly Cys Thr Ser Ala Gly Pro His
            50                 55                 60
Phe Asn Pro Leu Ser Arg Lys His Gly Gly Pro Lys Asp Glu Glu Arg
65                  70                 75                 80
His Val Gly Asp Leu Gly Asn Val Thr Ala Asp Lys Asp Gly Val Ala
                    85                 90                 95
Asp Val Ser Ile Glu Asp Ser Val Ile Ser Leu Ser Gly Asp His Cys
                100                105                110
Ile Ile Gly Arg Thr Leu Val Val His Glu Lys Ala Asp Asp Leu Gly
            115                120                125
Lys Gly Gly Asn Glu Glu Ser Thr Lys Thr Gly Asn Ala Gly Ser Arg
            130                135                140
Leu Ala Cys Gly Val Ile Gly Ile Ala Gln Asn Leu Asn Ser Gly Cys
145                 150                155                160
Asn Cys Ser Ile Tyr Pro Gly His Ile Thr Gly His Arg Met Ala Trp
                165                170                175
Lys Leu Gly Ser Ala Ala Arg Thr Thr Ser Gly Phe Val Ser Leu Phe
                180                185                190
Ala Pro Gly Ala Lys Gln Asn Glu Thr His Val Thr Gly Gly Ala Ala
                195                200                205
Ala Arg Thr Thr Ser Gly Leu Thr Ser Leu Phe Ser Pro Gly Ala Ser
            210                215                220
Gln Asn Ile Gln Leu Ile Val Asp Phe Ile Pro Val Glu Asn Leu Glu
225                 230                235                240
Thr Thr Met Arg Ser Pro Val Phe Thr Asp Asn Ser Ser Pro Pro Val
                245                250                255
Val Pro Gln Ser Phe Gln Val Ala His Leu His Ala Pro Thr Gly Ser
                260                265                270
Gly Lys Ser Thr Lys Val Pro Ala Ala Tyr Ala Ala Gln Gly Tyr Lys
            275                280                285
Val Leu Val Leu Asn Pro Ser Val Ala Ala Thr Leu Gly Phe Gly Ala
            290                295                300
Tyr Met Ser Lys Ala His Gly Ile Asp Pro Asn Ile Arg Thr Gly Val
305                 310                315                320
Arg Thr Ile Thr Thr Gly Ser Pro Ile Thr Tyr Ser Thr Tyr Gly Lys
                325                330                335
Phe Leu Ala Asp Gly Gly Cys Ser Gly Gly Ala Tyr Asp Ile Ile Ile
                340                345                350
Cys Asp Glu Cys His Ser Thr Asp Ala Thr Ser Ile Leu Gly Ile Gly
                355                360                365
Thr Val Leu Asp Gln Ala Glu Thr Ala Gly Ala Arg Leu Val Val Leu
            370                375                380
Ala Thr Ala Thr Pro Pro Gly Ser Val Thr Val Pro His Pro Asn Ile
385                 390                395                400
Glu Glu Val Ala Leu Ser Thr Thr Gly Glu Ile Pro Phe Tyr Gly Lys
                405                410                415
Ala Ile Pro Leu Glu Val Ile Lys Gly Gly Arg His Leu Ile Phe Cys
                420                425                430
```

```
His Ser Lys Lys Lys Cys Asp Glu Leu Ala Ala Lys Leu Val Ala Leu
        435                 440                 445
Gly Ile Asn Ala Val Ala Tyr Tyr Arg Gly Leu Asp Val Ser Val Ile
    450                 455                 460
Pro Thr Ser Gly Asp Val Val Val Ala Thr Asp Ala Leu Met Thr
465                 470                 475                 480
Gly Tyr Thr Gly Asp Phe Asp Ser Val Ile Asp Cys Asn Thr Cys Val
                485                 490                 495
Thr Gln Thr Val Asp Phe Ser Leu Asp Pro Thr Phe Thr Ile Glu Thr
            500                 505                 510
Ile Thr Leu Pro Gln Asp Ala Val Ser Arg Thr Gln Arg Arg Gly Arg
        515                 520                 525
Thr Gly Arg Gly Lys Pro Gly Ile Tyr Arg Phe Val Ala Pro Gly Glu
    530                 535                 540
Arg Pro Ser Gly Met Phe Asp Ser Ser Val Leu Cys Glu Cys Tyr Asp
545                 550                 555                 560
Ala Gly Cys Ala Trp Tyr Glu Leu Thr Pro Ala Glu Thr Thr Val Arg
                565                 570                 575
Leu Arg Ala Tyr Met Asn Thr Pro Gly Leu Pro Val Cys Gln Asp His
            580                 585                 590
Leu Glu Phe Trp Glu Gly Val Phe Thr Gly Leu Thr His Ile Asp Ala
        595                 600                 605
His Phe Leu Ser Gln Thr Lys Gln Ser Gly Glu Asn Leu Pro Tyr Leu
    610                 615                 620
Val Ala Tyr Gln Ala Thr Val Cys Ala Arg Ala Gln Ala Pro Pro Pro
625                 630                 635                 640
Ser Trp Asp Gln Met Trp Lys Cys Leu Ile Arg Leu Lys Pro Thr Leu
                645                 650                 655
His Gly Pro Thr Pro Leu Leu Tyr Arg Leu Gly Ala Val Gln Asn Glu
            660                 665                 670
Ile Thr Leu Thr His Pro Val Thr Lys Tyr Ile Met Thr Cys Met Ser
        675                 680                 685
Ala Asp Leu Glu Val Val Thr Ser Ala Cys Ser Gly Lys Pro Ala Ile
    690                 695                 700
Ile Pro Asp Arg Glu Val Leu Tyr Arg Glu Phe Asp Glu Met Glu Glu
705                 710                 715                 720
Cys Ser Gln His Leu Pro Tyr Ile Glu Gln Gly Met Met Leu Ala Glu
                725                 730                 735
Gln Phe Lys Gln Lys Ala Leu Gly Leu Ser Arg Gly Gly Lys Pro Ala
            740                 745                 750
Ile Val Pro Asp Lys Glu Val Leu Tyr Gln Gln Tyr Asp Glu Met Glu
        755                 760                 765
Glu Cys Ser Gln Ala Ala Pro Tyr Ile Glu Gln Ala Gln Val Ile Ala
    770                 775                 780
His Gln Phe Lys Glu Lys Val Leu Gly Leu Ile Asp Asn Asp Gln Val
785                 790                 795                 800
Val Val Thr Pro Asp Lys Glu Ile Leu Tyr Glu Ala Phe Asp Glu Met
                805                 810                 815
Glu Glu Cys Ala Ser Lys Ala Ala Leu Ile Glu Glu Gly Gln Arg Met
            820                 825                 830
Ala Glu Met Leu Lys Ser Lys Ile Gln Gly Leu Leu Gly Ile Leu Arg
        835                 840                 845
```

```
Arg His Val Gly Pro Gly Glu Gly Ala Val Gln Trp Met Asn Arg Leu
    850                 855                 860

Ile Ala Phe Ala Ser Arg Gly Asn His Val Ser Pro Thr His Tyr Val
865                 870                 875                 880

Pro Ser Arg Ser Arg Phe Ala Gln Ala Leu Pro Val Trp Ala Arg
                885                 890                 895

Pro Asp Tyr Asn Pro Pro Leu Val Glu Thr Trp Lys Lys Pro Asp Tyr
                900                 905                 910

Glu Pro Pro Val Val His Gly Arg Ser Arg Arg Phe Ala Gln Ala
                915                 920                 925

Leu Pro Val Trp Ala Arg Pro Asp Tyr Asn Pro Pro Leu Val Glu Thr
    930                 935                 940

Trp Lys Lys Pro Asp Tyr Glu Pro Pro Val Val His Gly Arg Lys Thr
945                 950                 955                 960

Lys Arg Asn Thr Asn Arg Arg Pro Gln Asp Val Lys Phe Pro Gly Gly
                965                 970                 975

Gly Gln Ile Val Gly Arg Arg Gly Pro Pro Ile Pro Lys Ala Arg Arg
                980                 985                 990

Pro Glu Gly Arg Thr Trp Ala Gln Pro Gly Tyr Pro Trp Pro Leu Tyr
                995                 1000                1005

Gly Asn Lys Asp Arg Arg Ser Thr Gly Lys Ser Trp Gly Lys Pro
    1010                1015                1020

Gly Tyr Pro Trp Pro Arg Lys Thr Lys Arg Asn Thr Asn Arg Arg
    1025                1030                1035

Pro Gln Asp Val Lys Phe Pro Gly Gly Gln Ile Val Gly Arg
    1040                1045                1050

Arg Gly Pro Pro Ile Pro Lys Ala Arg Arg Pro Glu Gly Arg Thr
    1055                1060                1065

Trp Ala Gln Pro Gly Tyr Pro Trp Pro Leu Tyr Gly Asn Lys Asp
1070                1075                1080

Arg Arg Ser Thr Gly Lys Ser Trp Gly Lys Pro Gly Tyr Pro Trp
    1085                1090                1095
Pro

<210> SEQ ID NO 11
<211> LENGTH: 21
<212> TYPE: PRT
<213> ORGANISM: Artificial
<220> FEATURE:
<223> OTHER INFORMATION: HCV epitopes

<400> SEQUENCE: 11

Gly Ser Ala Ala Arg Thr Thr Ser Gly Phe Val Ser Leu Phe Ala Pro
1               5                   10                  15

Gly Ala Lys Gln Asn
            20

<210> SEQ ID NO 12
<211> LENGTH: 10
<212> TYPE: DNA
<213> ORGANISM: Artificial
<220> FEATURE:
<223> OTHER INFORMATION: synthetic oligonucleotide

<400> SEQUENCE: 12
acaaaacaaa                                                        10
```

```
<210> SEQ ID NO 13
<211> LENGTH: 23
<212> TYPE: PRT
<213> ORGANISM: Artificial
<220> FEATURE:
<223> OTHER INFORMATION: an NS4a peptide

<400> SEQUENCE: 13

Lys Lys Gly Ser Val Val Ile Val Gly Arg Ile Val Leu Ser Gly Lys
1               5                   10                  15

Pro Ala Ile Ile Pro Lys Lys
            20

<210> SEQ ID NO 14
<211> LENGTH: 41
<212> TYPE: DNA
<213> ORGANISM: Artificial
<220> FEATURE:
<223> OTHER INFORMATION: HBgl-1

<400> SEQUENCE: 14
agcttacaaa acaaaatgca tcaccatcac catcacgcgc c                          41

<210> SEQ ID NO 15
<211> LENGTH: 52
<212> TYPE: DNA
<213> ORGANISM: Artificial
<220> FEATURE:
<223> OTHER INFORMATION: Hbgl-2

<400> SEQUENCE: 15
gcgtacgccg tgatgggcgc gtgatggtga tggtgatgca ttttgttttg ta              52

<210> SEQ ID NO 16
<211> LENGTH: 60
<212> TYPE: DNA
<213> ORGANISM: Artificial
<220> FEATURE:
<223> OTHER INFORMATION: Hbgl-5

<400> SEQUENCE: 16
catcacggcg tacgcccagc agacaagggg cctcctaggg tgcataatca ccagcctaac      60

<210> SEQ ID NO 17
<211> LENGTH: 42
<212> TYPE: DNA
<213> ORGANISM: Artificial
<220> FEATURE:
<223> OTHER INFORMATION: Hbgl-6

<400> SEQUENCE: 17
aggctggtga ttatgcaccc taggaggccc cttgtctgct gg                        42

<210> SEQ ID NO 18
<211> LENGTH: 34
<212> TYPE: DNA
<213> ORGANISM: Artificial
<220> FEATURE:
<223> OTHER INFORMATION: PCR primer

<400> SEQUENCE: 18
tttcctactt gaaaggctcc gcaggggggtc cgct                                34

<210> SEQ ID NO 19
<211> LENGTH: 30
<212> TYPE: DNA
```

<213> ORGANISM: Artificial
<220> FEATURE:
<223> OTHER INFORMATION: PCR primer

<400> SEQUENCE: 19
ggagcctttc aagtaggaaa tgggccgggg                                         30

<210> SEQ ID NO 20
<211> LENGTH: 57
<212> TYPE: DNA
<213> ORGANISM: Artificial
<220> FEATURE:
<223> OTHER INFORMATION: HA-1

<400> SEQUENCE: 20
agcttacaaa acaaaatggc gccaatcact gcttacgctc aacaaaccag aggcctc          57

<210> SEQ ID NO 21
<211> LENGTH: 57
<212> TYPE: DNA
<213> ORGANISM: Artificial
<220> FEATURE:
<223> OTHER INFORMATION: HA-2

<400> SEQUENCE: 21
ctaggaggcc tctggtttgt tgagcgtaag cagtgattgg cgccattttg ttttgta          57

<210> SEQ ID NO 22
<211> LENGTH: 84
<212> TYPE: DNA
<213> ORGANISM: Artificial
<220> FEATURE:
<223> OTHER INFORMATION: PI3p-1

<400> SEQUENCE: 22
ggccgacctg gaggtcgtca cgagcacctg ggtgctcgtt ggcggcgtcc tggctgcttt       60
ggccgcgtat tgcctgtcaa cagg                                              84

<210> SEQ ID NO 23
<211> LENGTH: 73
<212> TYPE: DNA
<213> ORGANISM: Artificial
<220> FEATURE:
<223> OTHER INFORMATION: PI3p-2

<400> SEQUENCE: 23
ctgcgtggtc atagtgggca gggtcgtctt gtccgggaag ccggcaatca tacctgacag       60
ggaagtcctc tac                                                          73

<210> SEQ ID NO 24
<211> LENGTH: 78
<212> TYPE: DNA
<213> ORGANISM: Artificial
<220> FEATURE:
<223> OTHER INFORMATION: PI3p-3

<400> SEQUENCE: 24
gtcaggtatg attgccggct tcccggacaa gacgaccctg cccactatga ccacgcagcc       60
tgttgacagg caatacgc                                                     78

<210> SEQ ID NO 25
<211> LENGTH: 60
<212> TYPE: DNA
<213> ORGANISM: Artificial

<220> FEATURE:
<223> OTHER INFORMATION: PI3p-4

<400> SEQUENCE: 25
ggccaaagca gccaggacgc cgccaacgag cacccaggtg ctcgtgacga cctccaggtc    60

<210> SEQ ID NO 26
<211> LENGTH: 34
<212> TYPE: DNA
<213> ORGANISM: Artificial
<220> FEATURE:
<223> OTHER INFORMATION: PI3p-5

<400> SEQUENCE: 26
cgagagttcg atgagatgga agagtgctga taag    34

<210> SEQ ID NO 27
<211> LENGTH: 53
<212> TYPE: DNA
<213> ORGANISM: Artificial
<220> FEATURE:
<223> OTHER INFORMATION: PI3p-6

<400> SEQUENCE: 27
tcgacttatc agcactcttc catctcatcg aactctcggt agaggacttc cct    53

<210> SEQ ID NO 28
<211> LENGTH: 33
<212> TYPE: DNA
<213> ORGANISM: Artificial
<220> FEATURE:
<223> OTHER INFORMATION: avsal-1

<400> SEQUENCE: 28
tgtcggccga cctggaggtc gtcacgtgat aag    33

<210> SEQ ID NO 29
<211> LENGTH: 41
<212> TYPE: DNA
<213> ORGANISM: Artificial
<220> FEATURE:
<223> OTHER INFORMATION: avsal-2

<400> SEQUENCE: 29
tcgacttatc acgtgacgac ctccaggtcg gccgacatgc a    41

<210> SEQ ID NO 30
<211> LENGTH: 27
<212> TYPE: DNA
<213> ORGANISM: Artificial
<220> FEATURE:
<223> OTHER INFORMATION: HA-5

<400> SEQUENCE: 30
agcttacaaa acaaaatggg ctgcgtg    27

<210> SEQ ID NO 31
<211> LENGTH: 41
<212> TYPE: DNA
<213> ORGANISM: Artificial
<220> FEATURE:
<223> OTHER INFORMATION: HA-6

<400> SEQUENCE: 31
gaccctgccc actatgacca cgcagcccat tttgttttgt a    41

```
<210> SEQ ID NO 32
<211> LENGTH: 72
<212> TYPE: DNA
<213> ORGANISM: Artificial
<220> FEATURE:
<223> OTHER INFORMATION: HA-7

<400> SEQUENCE: 32
gtcatagtgg gcagggtcgt cttgtccggt tccggttcca tcactgctta cgctcaacaa      60
accagaggcc tc                                                         72

<210> SEQ ID NO 33
<211> LENGTH: 58
<212> TYPE: DNA
<213> ORGANISM: Artificial
<220> FEATURE:
<223> OTHER INFORMATION: HA-8

<400> SEQUENCE: 33
ctaggaggcc tctggtttgt tgagcgtaag cagtgatgga accggaaccg gacaagac       58
```

HCV NON-STRUCTURAL PROTEIN MUTANTS AND USES THEREOF

CROSS-REFERENCE TO RELATED APPLICATIONS

The present application claims the benefit under 35 U.S.C. §119(e)(1) of U.S. Provisional Applications Ser. Nos. 60/621,790, filed Oct. 25, 2004; 60/621,502, filed Oct. 22, 2004; 60/618,390, filed Oct. 12, 2004; and 60/604,858, filed Aug. 27, 2004. The present application is also a continuation-in-part of U.S. patent application Ser. No. 10/899,715, filed Jul. 26, 2004, which is a continuation application of U.S. patent application Ser. No. 10/637,323, filed Aug. 8, 2003, now U.S. Pat. No. 6,797,809, which is a divisional application of U.S. patent application Ser. No. 09/881,654, filed Jun. 14, 2001, now U.S. Pat. No. 6,632,601, from which applications priority is claimed pursuant to 35 U.S.C. §120. U.S. patent application Ser. No. 09/881,654 claims the benefit under 35 U.S.C. §119(e)(1) of U.S. Provisional Patent Applications Ser. Nos. 60/212,082, filed Jun. 15, 2000; 60/280,811, filed Apr. 2, 2001; and 60/280,867, filed Apr. 2, 2001. The present application is also a continuation-in-part of U.S. patent application Ser. No. 10/643,853, filed Aug. 19, 2003, which is a divisional application of U.S. patent application Ser. No. 09/881,239, filed Jun. 14, 2001, now U.S. Pat. No. 6,630,298, from which applications priority is claimed pursuant to 35 U.S.C. §120. U.S. patent application Ser. No. 09/881,239 claims the benefit under 35 U.S.C. §119(e)(1) of U.S. Provisional Patent Applications Ser. Nos. 60/212,082, filed Jun. 15, 2000; 60/280,867, filed Apr. 2, 2001; and 60/280,811, filed Apr. 2, 2001. All of the foregoing applications are incorporated herein by reference in their entireties.

TECHNICAL FIELD

The present invention pertains generally to hepatitis C virus (HCV) constructs and methods of using the same. More particularly, the invention relates to immunogenic, immunoreactive HCV proteins with modified NS3 protease domains such that proteolytic activity of the NS3 molecule is inhibited. The modified proteins retain conformational epitopes and are therefore useful in immunoassays for diagnosing HCV infection as well as for stimulating immune responses against HCV.

BACKGROUND OF THE INVENTION

Hepatitis C Virus (HCV) is the principal cause of parenteral non-A, non-B hepatitis (NANBH) which is transmitted largely through body blood transfusion and body fluid exchange. The virus is present in 0.4 to 2.0% of the general population in the United States. Chronic hepatitis develops in about 50% of infections and of these, approximately 20% of infected individuals develop liver cirrhosis which sometimes leads to hepatocellular carcinoma. Accordingly, the study and control of the disease is of medical importance.

HCV was first identified and characterized as a cause of NANBH by Houghten et al. The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391-2399). The virus encodes a single polyprotein having more than 3000 amino acid residues (Choo et al., *Science* (1989) 244:359-362; Choo et al., *Proc. Natl. Acad. Sci. USA* (1991) 88:2451-2455; Han et al., *Proc. Natl. Acad. Sci. USA* (1991) 88:1711-1715). The polyprotein is processed co- and post-translationally into both structural and non-structural (NS) proteins.

In particular, as shown in FIG. 1, several proteins are encoded by the HCV genome. The order and nomenclature of the cleavage products of the HCV polyprotein is as follows: $NH_2$-C-E1-E2-P7-NS2-NS3-NS4a-NS4b-NS5a-NS5b-COOH. Initial cleavage of the polyprotein is catalyzed by host proteases which liberate three structural proteins, the N-terminal nucleocapsid protein (termed "core") and two envelope glycoproteins, "E1" (also known as E) and "E2" (also known as E2/NS1), as well as nonstructural (NS) proteins that contain the viral enzymes. The NS regions are termed NS2, NS3, NS4, NS4a, NS4b, NS5a and NS5b. NS2 is an integral membrane protein with proteolytic activity. NS2, either alone or in combination with NS3, cleaves the NS2-NS3 sissle bond which in turn generates the NS3 N-terminus and releases a large polyprotein that includes both serine protease and RNA helicase activities. The NS3 protease serves to process the remaining polyprotein. In particular, the HCV NS3 protein is a 630 amino acid protein containing three functional domains. The serine-like protease domain is located in the amino terminus, whereas helicase and NTPase activity are in the carboxy terminus. The serine protease of NS3 is responsible for the cleavage at the junction of NS3/4a, NS4a/b, NS4b/5a and NS5a/b.

A number of general and specific polypeptides useful as immunological and diagnostic reagents for HCV, derived from the HCV polyprotein, have been described. See, e.g., Houghton et al., European Publication Nos. 318,216 and 388,232; Choo et al., *Science* (1989) 244:359-362; Kuo et al., *Science* (1989) 244:362-364; Houghton et al., *Hepatology* (1991) 14:381-388; Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778. These publications provide an extensive background on HCV generally, as well as on the manufacture and uses of HCV polypeptide immunological reagents. For brevity, therefore, the disclosure of these publications is incorporated herein by reference.

Sensitive, specific methods for screening and identifying carriers of HCV and HCV-contaminated blood or blood products would provide an important advance in medicine. Post-transfusion hepatitis (PTH) occurs in approximately 10% of transfused patients, and HCV has accounted for up to 90% of these cases. Patient care as well as the prevention and transmission of HCV by blood and blood products or by close personal contact require reliable diagnostic and prognostic tools. Accordingly, several assays have been developed for the serodiagnosis of HCV infection. See, e.g., Choo et al., *Science* (1989) 244:359-362; Kuo et al., *Science* (1989) 244:362-364; Choo et al., *Br. Med. Bull.* (1990) 46:423-441; Ebeling et al., *Lancet* (1990) 335:982-983; van der Poel et al., *Lancet* (1990) 335:558-560; van der Poel et al., *Lancet* (1991) 337:317-319; Chien, D.Y., International Publication No. WO 94/01778; Valenzuela et al., International Publication No. WO 97/44469; and Kashiwakuma et al., U.S. Pat. No. 5,871,904.

U.S. Pat. No. 6,632,601, incorporated herein by reference in its entirety, describes immunoassays using NS3/4a conformational epitopes, in combination with multiple epitope fusion antigens (MEFAs). The assays provide sensitive and reliable methods for detecting early HCV seroconversion.

NS3/4a, expressed in yeast and purified under non-denaturing conditions as described in U.S. Pat. No. 6,632,601, contains both protease and helicase function. Because NS3/4a purified in this manner preserves the native conformation, it has been found to be more sensitive than the c200 or c33c antigens in early seroconversion antibody detection. In antibody assays using NS3/4a and MEFA 7.1 as antigens, seroconversion antibodies were detected 2-14 days earlier than currently marketed HCV assays. However, the NS3/4 protein undergoes self-hydrolysis and cleaves MEFA 7.1 due to the NS3 protease activity.

International Publication Nos. WO 04/00547 and WO 01/38360 describe HCV proteins including mutated NS3 protease domains with reduced proteolytic activity. However, there remains a need for sensitive, accurate diagnostic and prognostic tools in order to provide adequate patient care as well as to prevent transmission of HCV by blood and blood products or by close personal contact.

SUMMARY OF THE INVENTION

The present invention is based in part, on the finding that the use of HCV NS3 polypeptides with modified protease domains provides superior reagents for detecting HCV infection. The modified NS3 polypeptides retain conformational epitopes and hence immunoreactivity, while eliminating protease activity. Because the NS3 polypeptides are modified to eliminate protease activity, they are especially useful with other HCV polypeptides that retain NS3 proteolytic cleavage sites and that would otherwise be proteolytically cleaved by a functional NS3 protease. The modified NS3 polypeptides can therefore be used alone or in combination with other HCV reagents, and in particular, with multiple epitope fusion antigens (MEFAs) for accurately and efficiently detecting the presence of HCV infection. The use of MEFAs provides the added advantages of decreased masking problems, improved selectivity and improved sensitivity for detecting antibodies by allowing a greater number of epitopes on a unit area of substrate. The assays described herein may be used to detect HCV infection caused by any of the six known genotypes of HCV.

Accordingly, in one embodiment, the invention is directed to an immunoassay solid support comprising a polypeptide comprising a modified hepatitis C virus (HCV) NS3 protease domain such that protease activity of the modified NS3 polypeptide is inhibited relative to protease activity of a corresponding HCV NS3 polypeptide lacking the modification. The polypeptide comprises an NS3 conformational epitope and reacts specifically with anti-HCV antibodies present in a biological sample from an HCV-infected individual. In certain embodiments, the modification comprises a substitution of an amino acid corresponding to His-1083, Asp-1105 and/or Ser-1165, numbered relative to the full-length HCV-1 polyprotein, such as a substitution of Ala for the amino acid corresponding to Ser-1165, numbered relative to the full-length HCV-1 polyprotein. In additional embodiments, the polypeptide on the immunoassay solid support further comprises a substitution of Pro for the amino acid corresponding to Thr-1428 and a substitution of Ile for the amino acid corresponding to Ser-1429.

In further embodiments the polypeptide on the immunoassay solid support comprises the amino acid sequence of SEQ ID NO:2. In other embodiments, the polypeptide consists of the amino acid sequence of SEQ ID NO:2.

In yet additional embodiments, the polypeptide on the immunoassay solid support comprises the amino acid sequence of SEQ ID NO:4. In other embodiments, the polypeptide consists of the amino acid sequence of SEQ ID NO:4.

In additional embodiments, the polypeptide on the immunoassay solid support comprises the amino acid sequence of SEQ ID NO:6. In other embodiments, the polypeptide consists of the amino acid sequence of SEQ ID NO:6.

In yet additional embodiments, the immunoassay solid support further comprises a multiple epitope fusion antigen bound to the support, wherein the polypeptide and/or the multiple epitope fusion antigen react specifically with anti-HCV antibodies present in a biological sample from an HCV-infected individual.

In certain embodiments, the multiple epitope fusion antigen comprises the amino acid sequence depicted in SEQ ID NO:10, or an amino acid sequence with at least 80% sequence identity thereto, such as at least 90% or at least at least 98% sequence identity sequence identity thereto, and that reacts specifically with anti-HCV antibodies present in a biological sample from an HCV-infected individual. In additional embodiments, the multiple epitope fusion antigen consists of the amino acid sequence depicted in SEQ ID NO:10.

In further embodiments, the invention is directed to a method of detecting HCV infection in a biological sample. The method comprises:

(a) providing an immunoassay solid support as described above;

(b) combining a biological sample with the solid support under conditions which allow HCV antibodies, when present in the biological sample, to bind to the polypeptide and/or the multiple epitope fusion antigen to form a first immune complex;

(c) adding to the solid support from step (b) under complex forming conditions a detectably labeled antibody, wherein the labeled antibody is reactive with the immune complex; and (d) detecting second immune complexes formed between the detectably labeled antibody and the first immune complex, if any, as an indication of HCV infection in the biological sample.

In still further embodiments, the invention is directed to an immunodiagnostic test kit comprising an immunoassay solid support as described above, and instructions for conducting the immunodiagnostic test.

In additional embodiments, the invention is directed to an isolated polypeptide comprising the amino acid sequence of SEQ ID NO:2, wherein the polypeptide comprises an NS3 conformational epitope. In certain embodiments, the polypeptide consists of the amino acid sequence of SEQ ID NO:2.

In further embodiments, the invention is directed to an isolated polypeptide comprising the amino acid sequence of SEQ ID NO:4, wherein the polypeptide comprises an NS3 conformational epitope. In certain embodiments, the polypeptide consists of the amino acid sequence of SEQ ID NO:4.

In additional embodiments, the invention is directed to an isolated polypeptide comprising the amino acid sequence of SEQ ID NO:6, wherein the polypeptide comprises an NS3 conformational epitope. In certain embodiments, the polypeptide consists of the amino acid sequence of SEQ ID NO:6.

In yet further embodiments, the invention is directed to a polynucleotide comprising a coding sequence for any one of the above polypeptides, and a recombinant vector comprising the polynucleotide and control elements operably linked to the polynucleotide whereby the coding sequence can be transcribed and translated in a host cell. In additional embodiments, the invention is directed to a host cell transformed with the recombinant vector. In still further embodiments, the invention is directed to a method of producing a recombinant polypeptide comprising:

(a) providing a population of host cells described above; and (b) culturing the population of cells under conditions whereby the polypeptide encoded by the coding sequence present in the recombinant vector is expressed.

In additional embodiments, the invention is directed to a method of producing an immunoassay solid support, comprising:

(a) providing a solid support; and (b) binding to the solid support at least one polypeptide as described above. In certain embodiments, the method further comprises binding to the solid support at a discrete position a multiple epitope fusion antigen.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIG. 3 (SEQ ID NOS:7 and 8) depicts the DNA and corresponding amino acid sequence of a representative native, unmodified NS3 protease domain.

In FIGS. 4A-4C, the Ser normally present at position 1165 is substituted with Ala. Additionally, all of the mutants depicted in FIGS. 4A-4C include a substitution of Pro for Thr normally present at position 1428, and Ile for Ser normally present at position 1429. In FIG. 4A, the protein includes in N-terminal to C-terminal direction, an N-terminal Met, amino acids 1027-1657 of NS3 and amino acids 1658-1711 of NS4a and thus includes the full-length NS3 and NS4a domains of the HCV polyprotein. In FIG. 4B, the protein includes in N-terminal to C-terminal direction, an N-terminal Met, and amino acids 1027 to 1657 of NS3 and thus includes the full-length NS3 domain of the HCV polyprotein. In FIG. 4C, the protein includes in N-terminal to C-terminal direction, an N-terminal Met, amino acids 1678-1690 of NS4a, followed by the amino acid sequence Ser-Gly-Ser, then amino acids 1029 to 1657 of NS3.

FIGS. 5A-5C (SEQ ID NOS:1 and 2) depict the nucleotide sequence and corresponding amino acid sequence of the protein from FIG. 4A, termed "NS34aPI.1165."

FIGS. 6A-6C (SEQ ID NOS:3 and 4) depict the nucleotide sequence and corresponding amino acid sequence of the protein from FIG. 4B, termed "NS3PI.1165."

FIGS. 7A-7C (SEQ ID NOS:5 and 6) depict the nucleotide sequence and corresponding amino acid sequence of the protein from FIG. 4C, termed "d.4a.t.NS3PI.1165."

FIGS. 9A-9F (SEQ ID NOS:9 and 10) depict the DNA and corresponding amino acid sequence of MEFA 7.1.

FIGS. 11A-11C show representative MEFAs for use with the subject immunoassays. FIG. 11A is a diagrammatic representation of MEFA 3. FIG. 11B is a diagrammatic representation of MEFA 5. FIG. 11C is a diagrammatic representation of MEFA 6.

DETAILED DESCRIPTION OF THE INVENTION

Figure 1:
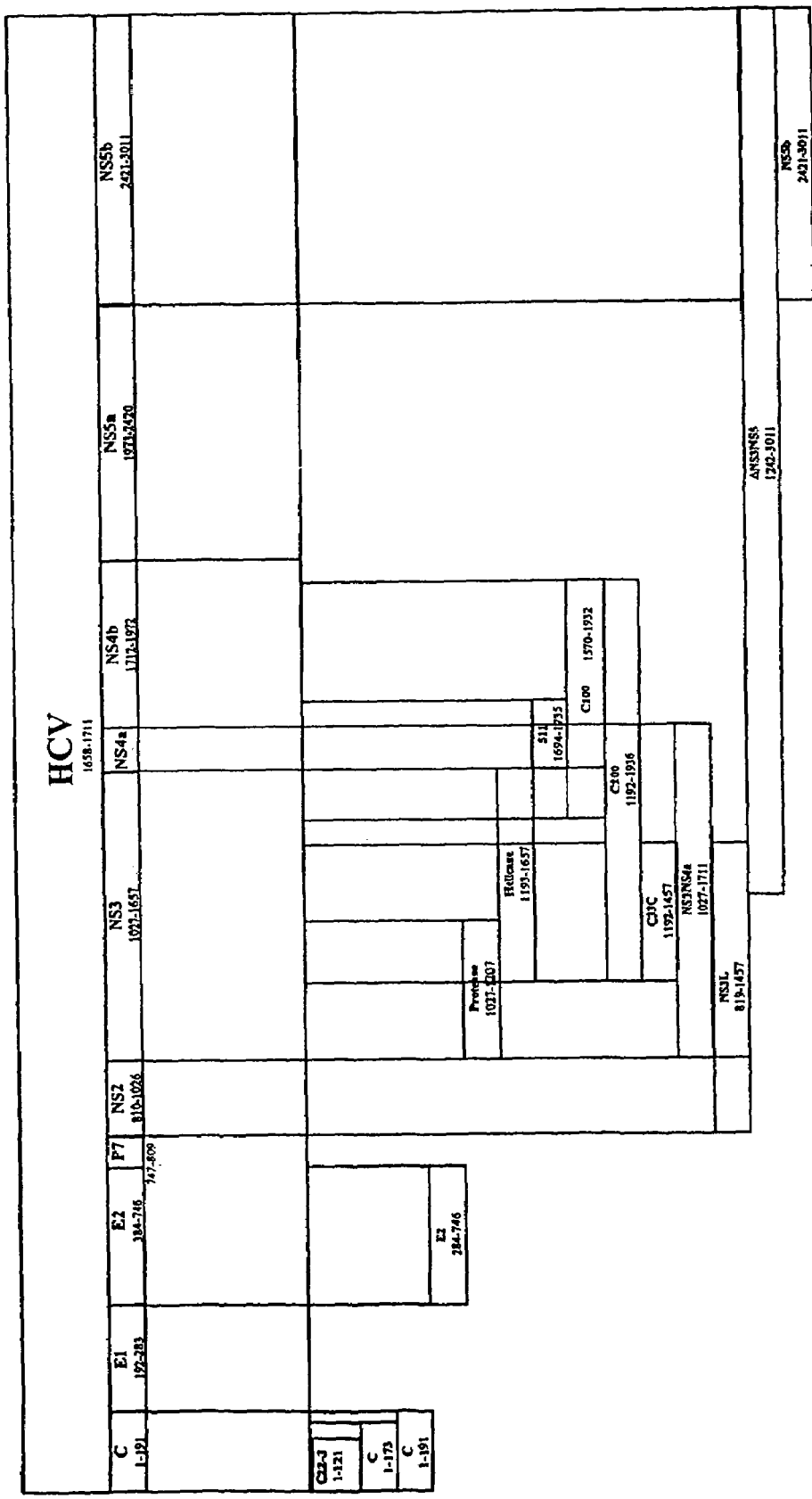
FIG. 1 is a diagrammatic representation of the HCV genome, depicting the various regions of the polyprotein from which the present assay reagents (proteins and antibodies) are derived.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

Alanine: Ala (A)     Arginine: Arg (R)
Asparagine: Asn (N)     Aspartic acid: Asp (D)

-continued

| | |
|---|---|
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains and isolates, such as, but not limited to, any of the isolates from strains 1, 2, 3, 4, 5 or 6 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS3/4a" polypeptide refers to native NS3/4a from any of the various HCV strains, as well as NS3/4a analogs, muteins and immunogenic fragments, as defined further below. The complete genotypes of many of these strains are known. See, e.g., U.S. Pat. No. 6,150,087 and GenBank Accession Nos. AJ238800 and AJ238799.

A polypeptide "derived from" an HCV polyprotein intends a polypeptide which comprises a sequence of one or more regions or portions of regions of the reference HCV polyprotein. Typically, the polypeptide is composed of regions or portions of regions that include epitopes, and will generally have an amino acid sequence substantially homologous to the reference polypeptide, as defined below. Thus, the term "derived from" is used to identify the original source of a molecule but is not meant to limit the method by which the molecule is made which can be, for example, by chemical synthesis or recombinant means.

The terms "analog" and "mutein" refer to biologically active derivatives of the reference molecule, or fragments of such derivatives, that retain desired activity, such as immunoreactivity in the assays described herein. In general, the term "analog" refers to compounds having a native polypeptide sequence and structure with one or more amino acid additions, substitutions (generally conservative in nature, or in the case of modified NS3, non-conservative in nature at the active proteolytic site) and/or deletions, relative to the native molecule, so long as the modifications do not destroy immunogenic activity. The term "mutein" refers to polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., *Chem Biol.* (2000) 7:463-473; and Simon et al., *Proc. Natl. Acad. Sci. USA* (1992) 89:9367-9371 for descriptions of peptoids). Preferably, the analog or mutein has at least the same immunoactivity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "modified NS3" is meant an NS3 polypeptide with a modification such that protease activity of the NS3 polypeptide is disrupted. The modified NS3 polypeptides therefore exhibit less protease activity as compared with the parent, unmodified NS3 polypeptide. The modification can include one or more amino acid additions, substitutions (generally non-conservative in nature) and/or deletions, relative to the native molecule, wherein the protease activity of the NS3 polypeptide is disrupted. Methods of measuring protease activity are discussed further below.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains immunoreactivity in the assays described herein. For example, preferred immunogenic fragments, include but are not limited to fragments of HCV core that comprise, e.g., amino acids 10-45, 10-53, 67-88, and 120-130 of the polyprotein, epitope 5-1-1 (in the NS4a/NS4b region of the viral genome) as well as defined epitopes derived from any of the regions of the polyprotein shown in FIG. 1, such as but not limited to the E1, E2, NS3 (e.g., polypeptide c33c from the NS3 region), NS4 (e.g., polypeptide c100 from the NS3/NS4 regions), NS3/4a and NS5 regions of the HCV polyprotein, as well as any of the other various epitopes identified from the HCV polyprotein. See, e.g., Chien et al., *Proc. Natl. Acad. Sci. USA* (1992) 89:10011-10015; Chien et al., *J. Gastroent. Hepatol*. (1993) 8:S33-39; Chien et al., International Publication No. WO 93/00365; Chien, D. Y., International Publication No. WO 94/01778; U.S. Pat. Nos. 6,150,087 and 6,121,020, all of which are incorporated by reference herein in their entireties.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol*. 23:709-715, all incorporated herein by reference in their entireties. Using such techniques, a number of epitopes of HCV have been identified. See, e.g., Chien et al., *Viral Hepatitis and Liver Disease* (1994) pp. 320-324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol*. (1982) 157:105-132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. The length of the epitope-defining sequence can be subject to wide variations as these epitopes are believed to be formed by the three-dimensional shape of the antigen (e.g., folding). Thus, amino acids defining the epitope can be relatively few in number, but widely dispersed along the length of the molecule, being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes present in the NS3/4a region are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest.

Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety. Alternatively, it is possible to express the antigens and further renature the protein after recovery. It is also understood that chemical synthesis may also provide conformational antigen mimitopes that cross-react with the native antigen's conformational epitope.

The term "multiple epitope fusion antigen" or "MEFA" as used herein intends a polypeptide in which multiple viral antigens are arranged as a single, continuous chain of amino acids, which chain does not occur in nature. As used herein, the MEFAs are limited to HCV antigens. The HCV antigens may be connected directly to each other by peptide bonds or may be separated by intervening amino acid sequences. The fusion antigens may also contain sequences exogenous to the HCV polyprotein. Moreover, the HCV sequences present may be from multiple genotypes and/or isolates of HCV. Examples of particular MEFAs for use in the present immunoassays are detailed in, e.g., International Publication No. WO 97/44469; U.S. Pat. Nos. 6,514,731, 6,428,792 and 6,632,601, all of which are incorporated herein by reference in its entirety, and are described further below.

An "antibody" intends a molecule that specifically binds to an epitope of interest present in an antigen. By "specifically binds" is meant that the antibody recognizes and interacts with the epitope in a "lock and key" type of interaction to form a complex between the antigen and antibody, as opposed to non-specific binding that might occur between the antibody and, for instance, the test substrate. Thus, for example, an HCV core antibody is a molecule that specifically binds to the HCV core protein. The term "antibody" as used herein includes antibodies obtained from both polyclonal and monoclonal preparations, as well as, the following: hybrid (chimeric) antibody molecules (see, for example, Winter et al. (1991) *Nature* 349:293-299; and U.S. Pat. No. 4,816,567); F(ab')2 and F(ab) fragments; Fv molecules (non-covalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, for example, Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, for example, Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. *Monclonal Antibodies and Cancer Therapy*, Alan R. Liss, 1985, p. 77.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of HCV, such as from strains 1, 2, or 3 of HCV. More specifically, epitopes are known, such as "5-1-1", occurring at approximately positions 1694-1735, numbered relative to the HCV-1 polyprotein sequence (see, FIG. 1), and such epitopes vary between the strains 1, 2, and 3. Thus, the epitope 5-1-1 from the three different strains are equivalent antigenic determinants and therefore are "copies" even though their sequences are not identical. In general the amino acid sequences of equivalent antigenic determinants will have a high degree of sequence homology, e.g., amino acid sequence homology of more than 30%, preferably more than 40%, when the two sequences are aligned.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

As used herein, a "biological sample" refers to a sample of tissue or fluid isolated from a subject, that commonly includes antibodies produced by the subject. Typical samples that include such antibodies are known in the art and include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

"Common solid support" intends a single solid matrix to which the HCV polypeptides used in the subject immunoassays are bound covalently or by noncovalent means such as hydrophobic adsorption.

"Immunologically reactive" or "immunoreactive" means that the antigen in question will react specifically with anti-HCV antibodies present in a biological sample from an HCV-infected individual.

"Immunogenic" intends that the antigen is question will elicit an immune reaction when administered to an individual.

"Immune complex" intends the combination formed when an antibody binds to an epitope on an antigen.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and $\alpha$-$\beta$-galactosidase.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery that HCV polypeptide mutants with modified NS3 domains, such that proteolytic activity of the NS3 protease is inhibited, can retain conformational epitopes and are therefore useful in immunoassays for detecting the presence of HCV infection. The NS3 mutants are especially useful in diagnostic methods for accurately detecting early HCV infection. The methods can be used to detect HCV infection during the early stages of HCV seroconversion, thereby increasing detection accuracy and reducing the incidence of false results.

In particular, the immunoassays described herein utilize highly immunoreactive epitopes derived from the NS3/4a region of the HCV polyprotein with mutations that disrupt proteolytic activity but retain conformational epitopes. The modified NS3 polypeptides can be used alone in immunoassays or in combination with other HCV antigens, such as multiple epitope fusion antigens comprising various HCV polypeptides, either from the same or different HCV genotypes and isolates, such as multiple immunodominant epitopes, for example, major linear epitopes of HCV core, E1, E2, NS3, 5-1-1, c100-3 and NS5 sequences. The methods can be conveniently practiced in a single assay, using any of the several assay formats described below, such as but not limited to, assay formats which utilize a solid support to which the HCV antigens are bound.

In order to further an understanding of the invention, a more detailed discussion is provided below regarding modified NS3 polypeptides and HCV fusions (i.e., MEFAs), as well as production of the proteins, and methods of using the proteins.

HCV Proteins

The genomes of HCV strains contain a single open reading frame of approximately 9,000 to 12,000 nucleotides, which is transcribed into a polyprotein. As shown in FIG. 1 and Table 1, an HCV polyprotein, upon cleavage, produces at least ten distinct products, in the following order: $NH_2$-Core-E1-E2-p7-NS2-NS3-NS4a-NS4b-NS5a-NS5b-COOH. The core polypeptide occurs at positions 1-191, numbered relative to HCV-1 (see, Choo et al. (1991) *Proc. Natl. Acad. Sci. USA* 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, in combination with NS3, (found at about positions 1027-1657), cleaves the NS2-NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657. NS3 liberates an NS3 cofactor (NS4a, found about positions 1658-1711), two proteins (NS4b found at about positions 1712-1972, and NS5a found at about positions 1973-2420), and an RNA-dependent RNA polymerase (NS5b found at about positions 2421-3011). Completion of polyprotein maturation is initiated by autocatalytic cleavage at the NS3-Ns4a junction, catalyzed by the NS3 serine protease.

TABLE 1

| Domain | Approximate Boundaries* |
|---|---|
| C (core) | 1-191 |
| E1 | 192-383 |
| E2 | 384-746 |
| P7 | 747-809 |
| NS2 | 810-1026 |
| NS3 | 1027-1657 |
| NS4a | 1658-1711 |
| NS4b | 1712-1972 |

TABLE 1-continued

| Domain | Approximate Boundaries* |
|---|---|
| NS5a | 1973-2420 |
| NS5b | 2421-3011 |

*Numbered relative to HCV-1. See, Choo et al. (1991) Proc. Natl. Acad. Sci. USA 88: 2451-2455.

The modified NS3 polypeptides of the invention are mutated to inhibit protease activity, such that further cleavage of a polypeptide including the modified NS3 domain, such as an NS3/4a polypeptide, as well as catalytic cleavage of additional HCV proteins used in combination with the modified NS3 polypeptide, is inhibited. The NS3 polypeptide can be modified by deletion of all or a portion of the NS3 protease domain. Alternatively, proteolytic activity can be inhibited by substitution of amino acids within active regions of the protease domain. Finally, additions of amino acids to active regions of the domain, such that the catalytic site is modified, will also serve to inhibit proteolytic activity. Preferably, the modifications made to reduce or eliminate protease activity do not disrupt the conformational epitopes in the native NS3 or NS3/4a proteins.

As explained above, the protease activity is found at about amino acid positions 1027-1207, numbered relative to the full-length HCV-1 polyprotein (see, Choo et al., *Proc. Natl. Acad. Sci. USA* (1991) 88:2451-2455), positions 2-182 of FIG. 3. The structure of the NS3 protease and active site are known. See, e.g., De Francesco et al., *Antivir. Ther.* (1998) 3:99-109; Koch et al., *Biochemistry* (2001) 40:631-640. Thus, deletions or modifications to the native sequence will typically occur at or near the active site of the molecule. Particularly, it is desirable to modify or make deletions to one or more amino acids occurring at positions 1- or 2-182, preferably 1- or 2-170, or 1- or 2-155 of FIG. 3. Preferred modifications are to the catalytic triad at the active site of the protease, i.e., H, D and/or S residues, in order to inactivate the protease. These residues occur at positions 1083, 1105 and 1165, respectively, numbered relative to the full-length HCV polyprotein (positions 58, 80 and 140, respectively, of FIG. 3). Such modifications will suppress proteolytic cleavage activity of the NS3 protease while maintaining immunoreactivity. Particularly preferred substitutions are non-conservative in nature, such as a substitution of Ala for one or more of the amino acid residues normally found at positions 1083, 1105 and 1165 of the protease domain. One of skill in the art can readily determine portions of the NS3 protease to delete in order to disrupt activity.

Moreover, other appropriate amino acid modifications at these sites can be readily determined by one of skill in the art based on the known structure and function of the HCV NS3 protease as described in e.g., De Francesco et al., *Antivir. Ther.* (1998) 3 (Suppl 3):99-109; and Schechter and Berger, *Biochim. Biophys. Res. Commun.* (1967) 27:157-162. In particular, it is known that NS3 protease is a serine protease and the proteolytic mechanism is based on nucleophilic attack of the targeted peptidic bond by a serine. In many cases the nucleophilic property of the group is improved by the presence of a histidine, held in a "proton acceptor state" by an aspartate. Aligned side chains of serine, histidine and aspartate build the catalytic triad common to most serine proteases. The active site of serine proteases is shaped as a cleft where the polypeptide substrate binds. Schechter and Berger, *Biochim. Biophys. Res. Commun.* (1967) 27:157-162 labeled amino acid residues from N to C terminus of the polypeptide substrate (Pi, . . . , P3, P2, P1, P1', P2', P3', . . . , Pj) and their respective binding subsites (Si, . . . , S3, S2, S1, S1', S2', S3', . . . , Sj) and found the cleavage is catalyzed between P1 and P1'. The NS3 protease adopts a chymotrypsin-like fold and includes a very long, solvent exposed substrate-binding site, consistent with the requirement for very long peptide substrates (P6-P4'). The NS3 protease has a preference for cysteine residues in the substrate P1 position. Thus, based on the known structure and function as described above and in the art, one of skill in the art can readily determine other amino acid substitutions, additions and deletions that will serve to disrupt the proteolytic activity of NS3 protease.

The presence or absence of NS3 proteolytic activity can be determined using methods known to those of skill in the art. For example, protease activity or lack thereof may be determined using the procedure described below in the examples, as well as using assays well known in the art. See, e.g., Takeshita et al., *Anal. Biochem.* (1997) 247:242-246; Kakiuchi et al., *J. Biochem.* (1997) 122:749-755; Sali et al., *Biochemistry* (1998) 37:3392-3401; Cho et al., *J. Virol. Meth.* (1998) 72:109-115; Cerretani et al., *Anal. Biochem.* (1999) 266:192-197; Zhang et al., *Anal. Biochem.* (1999) 270:268-275; Kakiuchi et al., *J. Virol. Meth.* (1999) 80:77-84; Fowler et al., *J. Biomol. Screen.* (2000) 5:153-158; and Kim et al., *Anal. Biochem.* (2000) 284:42-48.

Figure 4:
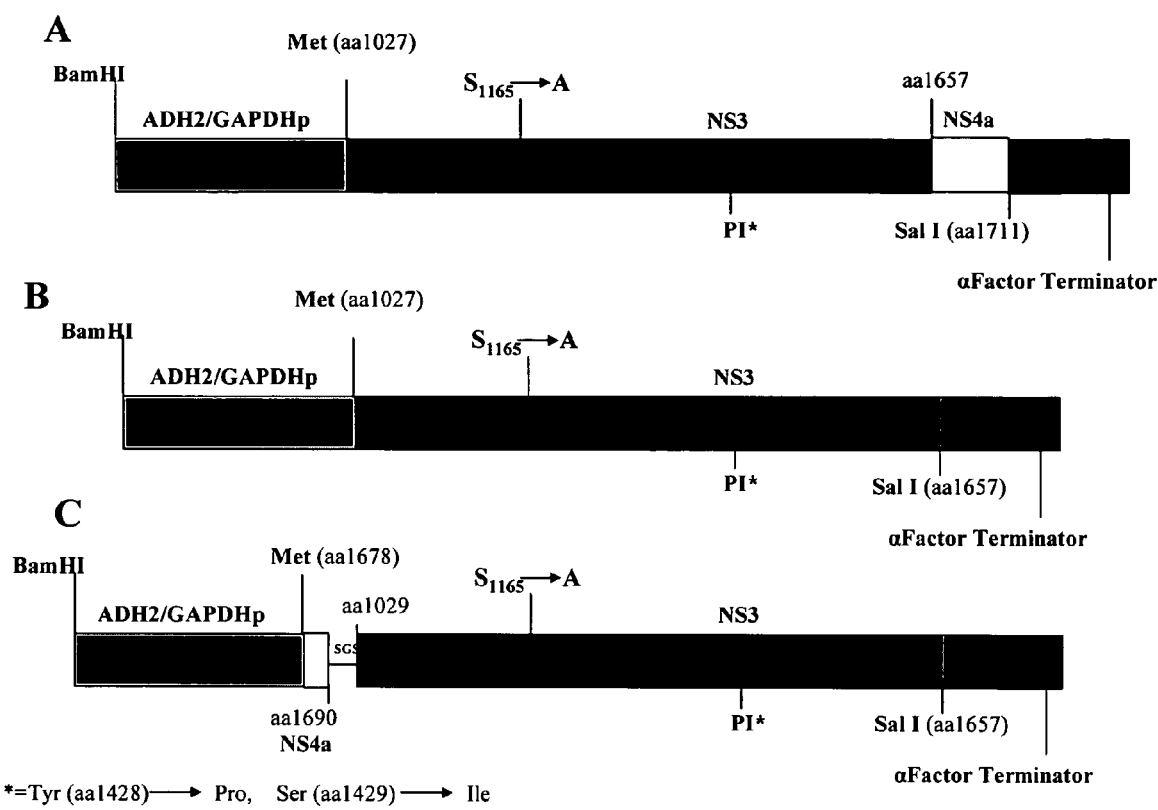
FIGS. 4A-4C are diagrammatic representations of mutant NS3 proteins according to the invention.

Additional mutations may also, but need not be, present in the NS3 molecule, such as mutations in the helicase domain, for example, substitution of one or both of the amino acid residues found at positions 1428 and 1429, such as Pro for Thr normally present at position 1428 and Ile for Ser normally present at position 1429. These mutations are termed "PI" mutants herein. FIG. 4B shows a representative modified NS3 construct. The protein includes an N-terminal Met and amino acids 1027-1657 of NS3 and therefore includes the full-length NS3 domain of the HCV polyprotein. The Ser normally present at position 1165 is substituted with Ala. Moreover, the mutant includes the PI substitution described above. The DNA and amino acid sequences of this construct are depicted in FIGS. 6A-6C.

The modified NS3 polypeptides of the present invention can also include, in addition to a modified NS3 protease domain, the NS3 helicase domain (that is, the entire NS3 polypeptide sequence, and/or one or more polypeptides from one or more other regions of an HCV polyprotein. Preferably, the modified NS3 polypeptides will include the NS4a polypeptide or a fragment thereof. In fact, all the regions of the HCV polyprotein can be present in such fusions. These polypeptides may derived from the same HCV isolate as the NS3 polypeptide, or from different strains and isolates including isolates having any of the various HCV genotypes, to provide increased protection against a broad range of HCV genotypes. Additionally, polypeptides can be selected based on the particular viral clades endemic in specific geographic regions where immunodiagnostics will be used. It is readily apparent that the modified HCV proteins provide an effective means of diagnosing HCV infection in a wide variety of contexts.

Nucleic acid and amino acid sequences of a number of HCV strains and isolates, including nucleic acid and amino acid sequences of the various regions of the HCV polyprotein, including Core, NS2, p7, E1, E2, NS3, NS4a, NS4b, NS5a, NS5b genes and polypeptides have been determined. For example, isolate HCV J1.1 is described in Kubo et al. (1989) Japan. Nucl. Acids Res. 17:10367-10372; Takeuchi et al. (1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113 respectively.

Publications that describe HCV-1 isolates include Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18~, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254.

Each of the components of a fusion protein can be obtained from the same HCV strain or isolate or from different HCV strains or isolates. For example, the modified NS3 polypeptide can be derived from a first strain of HCV, and other HCV polypeptides present can be derived from a second strain of HCV. Alternatively, one or more of the other HCV polypeptides, for example NS2, NS4a, NS4b, Core, p7, E1 and/or E2, if present, can be derived from a first strain of HCV, and the remaining HCV polypeptides can be derived from a second strain of HCV. Additionally, each or the HCV polypeptides present can be derived from different HCV strains.

In certain embodiments, the modified NS3 protein also comprises an NS4a domain or portion thereof, e.g., an NS4a and/or an NS4b domain, or a fragment thereof. The modified NS3 protein (with or without the NS4a domain) can also be fused with other HCV regions, such as with an NS5a domain, a core polypeptide of an HCV, and the like. These regions need not be in the order in which they naturally occur in the native HCV polyprotein. Thus, for example, if present, the NS4a polypeptide may be fused to the N- and/or C-terminus of the NS3 polypeptide.

FIGS. 4A and 4C show representative modified NS3 polypeptides. In the figures, the Ser normally present at position 1165 is substituted with Ala. Additionally, the mutants include the PI substitution described above, i.e., a substitution of Pro for Thr normally present at position 1428, and Ile for Ser normally present at position 429. In FIG. 4A, the protein includes in N-terminal to C-terminal direction, an N-terminal Met and amino acids 1027-1657 of NS3 and 1658-1711 of NS4a. This fusion therefore includes the full-length NS3 and NS4a domains of the HCV polyprotein. The nucleotide sequence and corresponding amino acid sequence of this protein is shown in FIGS. 5A-5C. In FIG. 4C, the protein includes in N-terminal to C-terminal direction, an N-terminal Met and amino acids 1678-1690 of NS4a, followed by the amino acid sequence SGS, then amino acids 1029 to 1657 of NS3. Thus, this fusion includes 13 amino acids of the NS4a domain, followed by a tripeptide flexible linker sequence (termed a "turn" sequence) and then almost the entire NS3 domain (except the first two N-terminal amino acids). The turn sequence allows the NS4a to fold into the pocket within the protease. The nucleotide sequence and corresponding amino acid sequence of this protein is shown in FIGS. 7A-7C. The numbering herein is with reference to the full-length HCV-1 polyprotein and equivalent regions in other HCV serotypes is readily determined.

The modified NS3 polypeptides described above may be used in immunoassays with multiple epitope fusion antigens (termed "MEFAs"), as described in International Publication No. WO 97/44469 and U.S. Pat. Nos. 6,514,731 and 6,428, 792, the disclosures of which are incorporated herein by reference in their entireties. Such MEFAs include multiple epitopes derived from two or more of the various viral regions of the HCV polyprotein shown in FIG. 1 and Table 1 and described in detail above. The use of such modified NS3 polypeptides with the MEFAs assures that NS3 proteolytic cleavage of the MEFA will not occur, thus providing better reagents for use in HCV immunoassays.

The multiple HCV antigens are arranged as a single, continuous chain of amino acids, which chain does not occur in nature. Thus, the linear order of the epitopes is different than their linear order in the genome in which they occur. The linear order of the sequences of the MEFAs for use herein is preferably arranged for optimum antigenicity. Preferably, the epitopes are from more than one HCV strain, thus providing the added ability to detect multiple strains of HCV in a single assay. Thus, the MEFAs for use herein may comprise various immunogenic regions derived from the polyprotein described above. Moreover, a protein resulting from a frameshift in the core region of the polyprotein, such as described in International Publication No. WO 99/63941, may be used in the MEFAs or fusions with the modified NS3 described above. If desired, at least 2, 3, 4, 5, 6, 7, 8, 9, or 10 or more of one or more epitopes derived from the HCV polyprotein may occur in the fusion protein.

Additional HCV epitopes for use in the MEFAs include epitopes derived from the hypervariable region of E2, such as a region spanning amino acids 384-414 or 390-410, or the consensus sequence from this region, Gly-Ser-Ala-Ala-Arg-Thr-Thr-Ser-Gly-Phe-Val-Ser-Leu-Phe-Ala-Pro-Gly-Ala-Lys-Gln-Asn (SEQ ID NO:11), which represents a consensus sequence for amino acids 390-410 of the HCV type 1 genome. A representative E2 epitope present in a MEFA of the invention can comprise a hybrid epitope spanning amino acids 384-414. Such a hybrid E2 epitope can include a consensus sequence representing amino acids 390-410 fused to a consensus sequence from a second strain. Alternatively, the E2 epitope present may comprise a hybrid epitope spanning amino acids 390-444. Such a hybrid E2 epitope can include a consensus sequence representing amino acids 390-410 as detailed above, fused to e.g., the native amino acid sequence for amino acids 411-444 of HCV E2.

Additionally, the antigens may be derived from various HCV strains. Multiple viral strains of HCV are known, and epitopes derived from any of these strains can be used in a fusion protein. It is well known that any given species of organism varies from one individual organism to another and further that a given organism such as a virus can have a number of different strains. For example, as explained above, HCV includes at least 6 genotypes. Each of these genotypes includes equivalent antigenic determinants. More specifically, each strain includes a number of antigenic determinants that are present on all strains of the virus but are slightly different from one viral strain to another. For example, HCV includes the antigenic determinant known as 5-1-1 (See, FIG. 1). The 5-1-1 epitope is found at approximately positions 1694-1735, numbered relative to the HCV-1 polyprotein sequence. This particular antigenic determinant appears in three different forms in HCV-1, HCV-2 and HCV-3. Accordingly, in a preferred embodiment of the invention all three of these forms of 5-1-1 appear on the multiple epitope fusion antigen used in the subject immunoassays. Similarly, equivalent antigenic determinants from the core region of different HCV strains may also be present. In general, equivalent antigenic determinants have a high degree of homology in terms of amino acid sequence which degree of homology is generally 30% or more, preferably 40% or more, when aligned. The multiple copy epitope of the present invention can also include multiple copies which are exact copies of the same epitope.

FIGS. 8 and 11A-11C show representative MEFAs for use in the present invention which are derived from HCV. However, it is to be understood that other epitopes derived from the HCV genome will also find use with the present assays.

Figure 8:
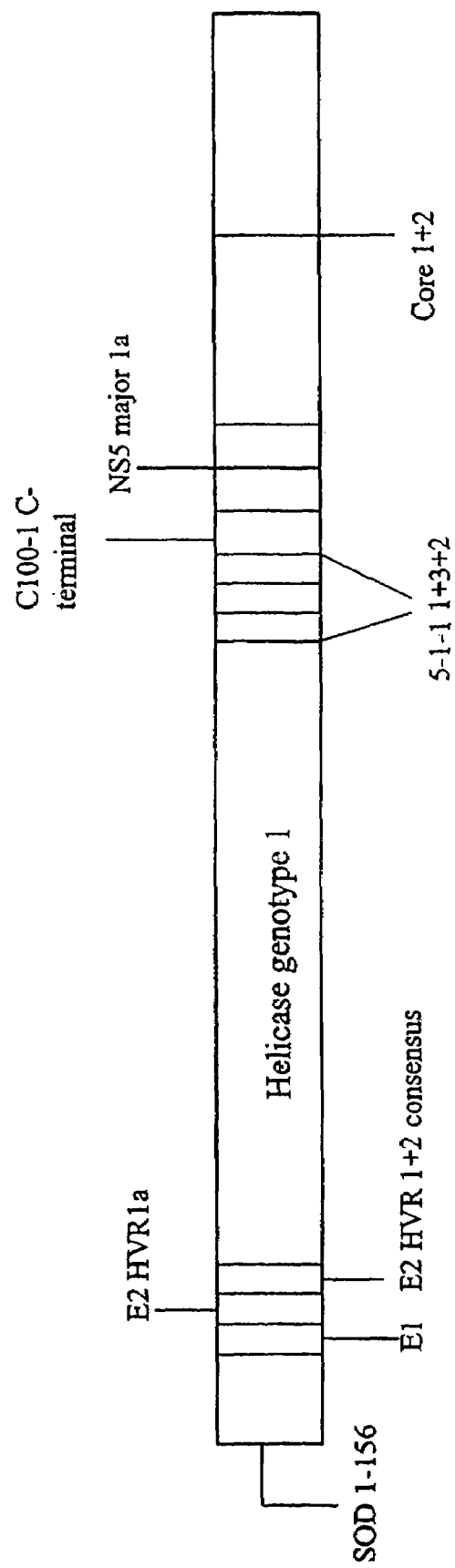
FIG. 8 is a diagrammatic representation of MEFA 7.1.
Figure 10:
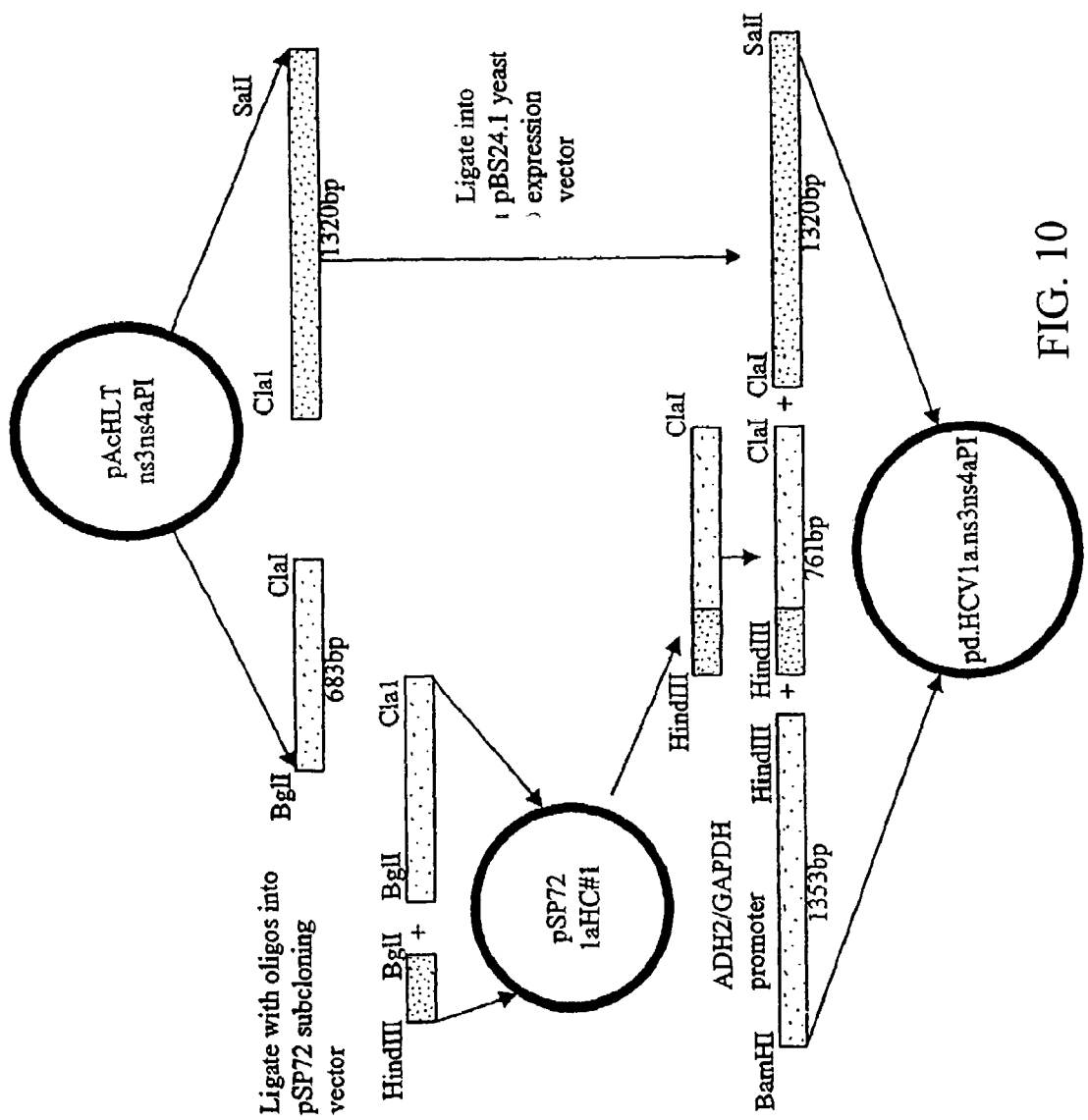
FIG. 10 is a diagram of the construction of pd.HCV1a.ns3 ns4aPI.

The DNA sequence and corresponding amino acid sequence of a representative multiple epitope fusion antigen, MEFA 7.1, is shown in FIGS. 9A-9F. This MEFA is also described in U.S. Pat. No. 6,632,601, incorporated herein by reference in its entirety. The general structural formula for MEFA 7.1 is shown in FIG. 8 and is as follows: hSOD-E1 (type 1)-E2 HVR consensus(type 1a)-E2 HVR consensus (types 1 and 2)-helicase(type 1)-5-1-1(type 1)-5-1-1(type 3)-5-1-1(type 2)-c100(type 1)-NS5(type 1)-NS5(type 1)-core(types 1+2)-core(types 1+2). This multiple copy epitope includes the following amino acid sequence, numbered relative to HCV-1 (the numbering of the amino acids set forth below follows the numbering designation provided in Choo, et al. (1991) Proc. Natl. Acad. Sci. USA 88:2451-2455, in which amino acid #1 is the first methionine encoded by the coding sequence of the core region): amino acids 1-156 of superoxide dismutase (SOD, used to enhance recombinant expression of the protein); amino acids 303 to 320 of the polyprotein from the E1 region; amino acids 390 to 410 of the polyprotein, representing a consensus sequence for the hypervariable region of HCV-1a E2; amino acids 384 to 414 of the polyprotein from region E2, representing a consensus sequence for the E2 hypervariable regions of HCV-1 and HCV-2; amino acids 1193-1658 of the HCV-1 polyprotein which define the helicase; three copies of an epitope from 5-1-1, amino acids 1689-1735, one from HCV-1, one from HCV-3 and one from HCV-2, which copies are equivalent antigenic determinants from the three different viral strains of HCV; HCV polypeptide C100 of HCV-1, amino acids 1901-1936 of the polyprotein; two exact copies of an epitope from the NS5 region of HCV-1, each with amino acids 2278 to 2313 of the HCV polyprotein; and two copies of an epitope from the core region, one from HCV-1 and one from HCV-2, which copies are equivalent antigenic determinants represented by amino acids 9 to 32, 39-42 and 64-88 of HCV-1 and 67-84 of HCV-2.

Table 2 shows the amino acid positions of the various epitopes with reference to FIGS. 9A-9F herein.

TABLE 2

MEFA 7.1

| mefa aa# | 5' end site | epitope | hcv aa# | strain |
|---|---|---|---|---|
| 1-156 | Nco1 | hSOD | | |
| 159-176 | EcoR1 | E1 | 303-320 | 1 |
| 179-199 | Hind111 | E2 HVR1a consensus | 390-410 | 1 |
| 200-230 | | E2 HVR1 + 2 consensus | 384-414 | 1 + 2 |
| 231-696 | Sal1 | Helicase | 1193-1658 | 1 |
| 699-745 | Sph1 | 5-1-1 | 1689-1735 | 1 |
| 748-794 | Nru1 | 5-1-1 | 1689-1735 | 3 |
| 797-843 | Cla1 | 5-1-1 | 1689-1735 | 2 |
| 846-881 | Ava1 | C100 | 1901-1936 | 1 |
| 884-919 | Xba1 | NS5 | 2278-2313 | 1 |
| 922-957 | Bgl11 | NS5 | 2278-2313 | 1 |
| 958-1028 | Nco1 | core epitopes | 9-32, 39-42 64-88 67-84 | 1 1 2 |
| 1029-1099 | Bal1 | core epitopes | 9-32, 39-42, 64-88 67-84 | 1 1 2 |

Figure 2:
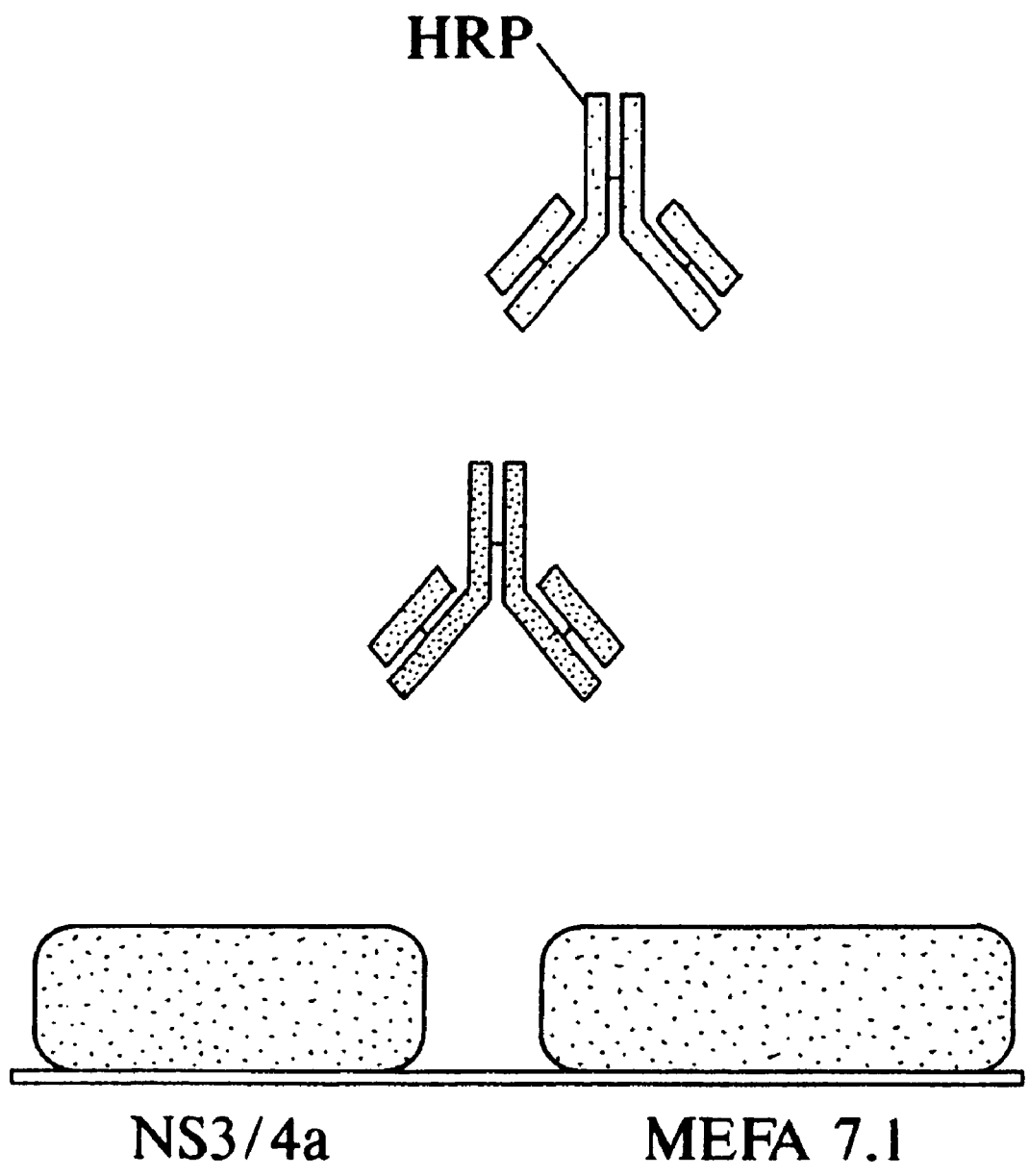
FIG. 2 is a schematic drawing of a representative immunoassay using modified NS3 polypeptides according to the invention where HCV antigens are immobilized on a solid support.

In one embodiment of the invention, depicted in FIG. 2, a rapid capture ligand immunoassay is performed using a modified NS3 polypeptide, or fusion including a modified NS3 polypeptide, and one or more multiple epitope fusion antigens, such as MEFA 7.1. The sample is combined with the antigens, which may be present on a solid support, as described further below. If the sample is infected with HCV, HCV antibodies to those epitopes present on the solid support will bind to the solid support components. Detection is by the attachment of a detectable marker (such as horse radish peroxidase (HRP) as shown in FIG. 2) to a member of the antigen/antibody complex. Attachment may be by covalent means or by subsequent binding of detectably labeled antibodies, such as in a standard sandwich assay, or by enzyme reaction, the product of which reaction is detectable. The detectable marker may include, but is not limited to, a chromophore, an antibody, an antigen, an enzyme, an enzyme reactive compound whose cleavage product is detectable, rhodamine or rhodamine derivative, biotin, avidin, strepavidin, a fluorescent compound, a chemiluminescent compound, such as dimethyl acridinium ester (DMAE), derivatives and/or combinations of these markers. A detectably labeled anti-human antibody, capable of detecting a human IgG molecule present, can be conveniently used.

Production of HCV Antigens

As explained above, the molecules of the present invention are generally produced recombinantly. Thus, polynucleotides encoding HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PVR. See, e.g., Jayaraman et al. (1991) *Proc. Natl. Acad. Sci. USA* 88:4084-4088. Additionally, oligonucleotide directed synthesis (Jones et al. (1986) *Nature* 54:75-82), oligonucleotide directed mutagenesis of pre-existing nucleotide regions (Riechmann et al. (1988) *Nature* 332:323-327 and Verhoeyen et al. (1988) *Science* 239:1534-1536), and enzymatic filling-in of gapped oligonucleotides using $T_4$ DNA polymerase (Queen et al. (1989) *Proc. Natl. Acad. Sci. USA* 86:10029-10033) can be used under the invention to provide molecules having altered or enhanced antigen-binding capabilities, and/or reduced immunogenicity.

Methods for producing mutants or analogs of the desired nucleotide sequence, such as NS3, or other HCV antigens, are well known. See, e.g., Dasmahapatra et al., U.S. Pat. No. 5,843,752 and Zhang et al., U.S. Pat. No. 5,990,276. Mutants or analogs of NS3 and other HCV proteins for use in immunoassays may be prepared by deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The recombinant production of various HCV antigens, including antigens used in the various fusions described above, has been described. See, e.g., International Publication Nos. WO 94/01778, WO 93/00365, WO 04/00547 and WO 01/38360; U.S. Pat. Nos. 5,350,671, 5,683,864, 6,346,375, 6,150,087, 6,514,731, 6,428,792 and 6,632,601; Chien et al., *J. Gastroent. Hepatol.* (1993) 8:S33-39; Chien, D. Y., International Publication No. WO 94/01778; Chien et al., *Proc. Natl. Acad. Sci. USA* (1992) 89:10011-10015; the disclosures of all of which are incorporated herein by reference in their entireties. A preferred method of producing modified NS3 polypeptides is described in Example 1.

Immunodiagnostic Assays

Once produced, the HCV antigens may be used in virtually any assay format that employs a known antigen to detect antibodies. A common feature of all of these assays is that the antigen is contacted with the body component suspected of containing HCV antibodies under conditions that permit the antigen to bind to any such antibodies present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

The immunoassay may be, without limitation, a heterogenous or a homogeneous format, and of a standard or competitive type. In a heterogeneous format, the polypeptide is typically bound to a solid matrix or support to facilitate separation of the sample from the polypeptide after incubation. A solid support, for the purposes of this invention, can be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

If more than one HCV antigen is used in the assays, for example, a modified NS3 polypeptide and a MEFA or another HCV antigen, the antigens can be provided on the same solid substrate or on different solid substrates that are combined in the assay. Thus, for example, the antigens can be present as discrete entities on, e.g., a plate, or can be present on, for example, individual microbeads that are added together for use in the assay of interest.

In one context, as depicted in FIG. 2, a solid support is first reacted with the HCV antigens such as a modified NS3 polypeptide, e.g., NS3aPI.1165, NS3PI.1165 or d.4a.t.NS3PI.1165, and a MEFA, such as MEFA 7.1 (collectively called "the solid-phase components" herein), under suitable binding conditions such that the molecules are sufficiently immobilized to the support. Sometimes, immobilization to the support can be enhanced by first coupling the antigen to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) *Bioconjugate Chem.* 3:2-13; Hashida et al. (1984) *J. Appl. Biochem.* 6:56-63; and Anjaneyulu and Staros (1987) *International J. of Peptide and Protein Res.* 30:117-124.

After reacting the solid support with the solid-phase components, any nonimmobilized solid-phase components are removed from the support by washing, and the support-bound components are then contacted with a biological sample suspected of containing HCV antibodies (collectively called "ligand molecules" herein) under suitable binding conditions. If HCV antibodies are present in the sample, they will form a complex with the HCV antigens. After washing to remove any nonbound ligand molecules, detectably labeled antibodies, such as anti-xenogenic (e.g., anti-human) antibodies, which recognize an epitope on anti-HCV antibodies, are added. These antibodies bind due to complex formation.

Figure 12:
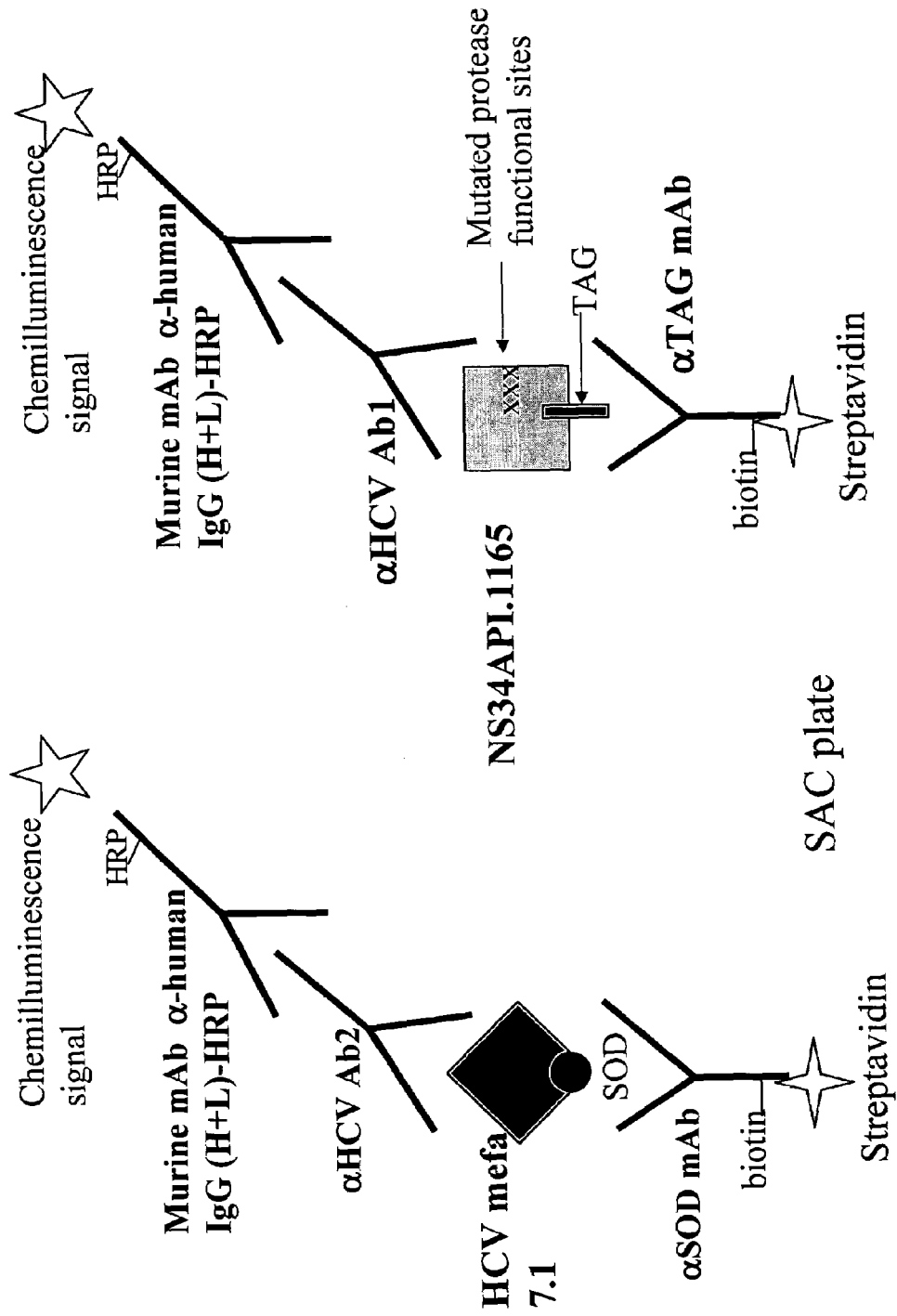
FIG. 12 is a schematic drawing of a representative immunoassay format using modified NS3 polypeptides with a streptavidin-coated solid support.

Another assay format is shown in FIG. 12. This assay format, well known in the art, uses a streptavidin-coated solid support reacted with biotin labeled antibodies that bind the modified NS3 and, optionally, a MEFA, such as MEFA 7.1. The sample is added under suitable binding conditions. If HCV antibodies are present in the sample, they will form a complex with the HCV antigens. After washing to remove any nonbound ligand molecules, detectably labeled antibodies are added, as described above.

In a homogeneous format, the test sample is incubated with the combination of antigens in solution. For example, it may be under conditions that will precipitate any antigen-antibody complexes which are formed. Both standard and competitive formats for homogeneous assays are also known in the art.

In a standard format, the amount of HCV antibodies forming the antibody-antigen complex is directly monitored. This may be accomplished by determining whether labeled anti-xenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

More particularly, complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label). In an immunoprecipitation or agglutination assay format, the reaction between the HCV antigens and the antibody forms a network that precipitates from the solution or suspension and forms a visible layer or film of precipitate. If no anti-HCV antibody is present in the test specimen, no visible precipitate is formed. The above-described assay reagents, including the immunoassay solid support with bound antibodies and antigens, as well as antibodies and antigens to be reacted with the captured sample, can be provided in kits, with suitable instructions and other necessary reagents, in order to conduct immunoassays as described above. The kit will normally contain in separate containers the combination of antigens (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular immunoassay used, other packaged reagents and materials (i.e. wash buffers and the like). Standard immunoassays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Production of Modified NS3 Proteins

I. NS34aPI

NS34aPI, with mutations to the NS3 helicase domain but not the protease domain, was produced for expression by the yeast expression vector pBS24.1 as follows. NS34aPI includes the amino acid sequence for the native NS3/4a polypeptide, with the exception that amino acid Thr-1428 and Ser-1429, numbered relative to the HCV-1 full-length sequence, have been mutated to Pro and Ile, respectively. The yeast expression vector pBS24.1 contains 2µ sequences for autonomous replication in yeast and the yeast genes leu2-d and URA3 as selectable markers. The β-lactamase gene and the ColE1 origin of replication, required for plasmid replication in bacteria, are also present in this expression vector. Plasmid pd.hcv1a.ns3ns4aPI, encoding NS34aPI was produced as follows. A two step procedure was used. First, the following DNA pieces were ligated together: (a) synthetic oligonucleotides which would provide a 5' HindIII cloning site, followed by the sequence ACAAAACAAA (SEQ ID NO:12), the initiator ATG, and codons for HCV1a, beginning with amino acid 1027 and continuing to a BglI site at amino acid 1046; (b) a 683 bp BglI-ClaI restriction fragment (encoding amino acids 1046-1274) from pAcHLTns3ns4aPI; and (c) a pSP72 vector (Promega, Madison, Wis., GenBank/EMBL Accession Number X65332) which had been digested with HindIII and ClaI, dephosphorylated, and gel-purified. Plasmid pAcHLTns3ns4aPI was derived from pAcHLT, a baculovirus expression vector commercially available from BD Pharmingen (San Diego, Calif.). In particular, a pAcHLT EcoRI-PstI vector was prepared, as well as the following fragments: EcoRI-AlwnI, 935 bp, corresponding to amino acids 1027-1336 of the HCV-1 genome; AlwnI-SacII, 247 bp, corresponding to amino acids 1336-1419 of the HCV-1 genome; HinfI-BglI, 175 bp, corresponding to amino acids 1449-1509 of the HCV-1 genome; BglI-PstI, 619 bp, corresponding to amino acids 1510-1711 of the HCV-1 genome, plus the transcription termination codon. A SacII-HinfI synthetically generated fragment of 91 bp, corresponding to amino acids 1420-1448 of the HCV-1 genome and containing the PI mutations (Thr-1428 mutated to Pro, Ser-1429 mutated to Ile), was ligated with the 175 bp HinfI-BglI fragment and the 619 bp BglI-PstI fragment described above and subcloned into a pGEM-5Zf(+) vector digested with SacII and PstI. pGEM-5Zf(+) is a commercially available *E. coli* vector (Promega, Madison, Wis., GenBank/EMBL Accession Number X65308). After transformation of competent HB101 cells, miniscreen analysis of individual clones and sequence verification, an 885 bp SacII-PstI fragment from pGEM5.PI clone2 was gel-purified. This fragment was ligated with the EcoRI-AlwnI 935 bp fragment, the AlwnI-SacII 247 bp fragment and the pAcHLT EcoRI-PstI vector, described above. The resultant construct was named pAcHLTns3 ns4aPI.

The ligation mixture above was transformed into HB101-competent cells and plated on Luria agar plates containing 100 μg/ml ampicillin. Miniprep analyses of individual clones led to the identification of putative positives, two of which were amplified. The plasmid DNA for pSP72 1aHC, clones #1 and #2 were prepared with a Qiagen Maxiprep kit and were sequenced.

Next, the following fragments were ligated together: (a) a 761 bp HindIII-ClaI fragment from pSP721aHC #1 (pSP72.1aHC was generated by ligating together the following: pSP72 which had been digested with HindIII and ClaI, synthetic oligonucleotides which would provide a 5=HindIII cloning site, followed by the sequence ACAAAACAAA (SEQ ID NO:12), the initiation codon ATG, and codons for HCV1a, beginning with amino acid 1027 and continuing to a BglII site at amino acid 1046, and a 683 bp BglII-ClaI restriction fragment (encoding amino acids 1046-1274) from pAcHLTns3ns4aPI); (b) a 1353 bp BamHI-HindIII fragment for the yeast hybrid promoter ADH2/GAPDH; (c) a 1320 bp ClaI-SalI fragment (encoding HCV1a amino acids 1046-1711 with Thr 1428 mutated to Pro and Ser 1429 mutated to Ile) from pAcHLTns3ns4aPI; and (d) the pBS24.1 yeast expression vector which had been digested with BamHI and SalI, dephosphorylated and gel-purified. The ligation mixture was transformed into competent HB101 and plated on Luria agar plates containing 100 μg/ml ampicillin. Miniprep analyses of individual colonies led to the identification of clones with the expected 3446 bp BamHI-SalI insert which was comprised of the ADH2/GAPDH promoter, the initiator codon ATG and HCV1a NS34a from amino acids 1027-1711, with Thr 1428 mutated to Pro and Ser 1429 mutated to Ile. The construct was named pd.HCV1a.ns3ns4aPI.

*S. cerevisiae* strain AD3 was transformed with pd.HCV1a.ns3ns4aPI and single transformants were checked for expression after depletion of glucose in the medium. The recombinant protein was expressed at high levels in yeast, as detected by Coomassie blue staining and confirmed by immunoblot analysis using a polyclonal antibody to the helicase domain of NS3.

The NS3/4a protein was purified as follows. *S. cerevisiae* cells from above, expressing the NS34aPI protein were harvested and the cells were suspended in lysis buffer (50 mM Tris pH 8.0, 150 mM NaCl, 1 mM EDTA, 1 mM PMSF, 0.1 μM pepstatin, 1 μM leupeptin) and lysed in a Dyno-Mill (Wab Willy A. Bachofon, Basel, Switzerland) or equivalent apparatus using glass beads, at a ratio of 1:1:1 cells:buffer:0.5 mm glass beads. The lysate was centrifuged at 30100×g for 30 min at 4° C. and the pellet containing the insoluble protein fraction was added to wash buffer (6 ml/g start cell pellet weight) and rocked at room temperature for 15 min. The wash buffer consisted of 50 mM NaPO$_4$ pH 8.0, 0.3 M NaCl, 5 mM β-mercaptoethanol, 10% glycerol, 0.05% octyl glucoside, 1 mM EDTA, 1 mM PMSF, 0.1 μM pepstatin, 1 μM leupeptin. Cell debris was removed by centrifugation at 30100×g for 30 min at 4° C. The supernatant was discarded and the pellet retained.

Protein was extracted from the pellet as follows. 6 ml/g extraction buffer was added and rocked at room temperature for 15 min. The extraction buffer consisted of 50 mM Tris pH 8.0, 1 M NaCl, 5 mM β-mercaptoethanol, 10% glycerol, 1 mM EDTA, 1 mM PMSF, 0.1 μM pepstatin, 1 μM leupeptin. This was centrifuged at 30100×g for 30 min at 4° C. The supernatant was retained and ammonium sulfate added to 17.5% using the following formula: volume of supernatant (ml) multiplied by x % ammonium sulfate/(1−x % ammonium sulfate)=ml of 4.1 M saturated ammonium sulfate to add to the supernatant. The ammonium sulfate was added dropwise while stirring on ice and the solution stirred on ice for 10 min. The solution was centrifuged at 17700×g for 30 min at 4° C. and the pellet retained and stored at 2° C. to 8° C. for up to 48 hrs.

The pellet was resuspended and run on a Poly U column (Poly U Sepharose 4B, Amersham Pharmacia) at 4° C. as follows. Pellet was resuspended in 6 ml Poly U equilibration buffer per gram of pellet weight. The equilibration buffer consisted of 25 mM HEPES pH 8.0, 200 mM NaCl, 5 mM DTT (added fresh), 10% glycerol, 1.2 octyl glucoside. The solution was rocked at 4° C. for 15 min and centrifuged at 31000×g for 30 min at 4° C.

A Poly U column (1 ml resin per gram start pellet weight) was prepared. Linear flow rate was 60 cm/hr and packing flow rate was 133% of 60 cm/hr. The column was equilibrated with equilibration buffer and the supernatant of the resuspended ammonium sulfate pellet was loaded onto the equilibrated column. The column was washed to baseline with the equilibration buffer and protein eluted with a step elution in the following Poly U elution buffer: 25 mM HEPES pH 8.0, 1 M NaCl, 5 mM DTT (added fresh), 10% glycerol, 1.2 octyl glucoside. Column eluate was run on SDS-PAGE (Coomassie stained) and aliquots frozen and stored at −80° C. The presence of the NS34aPI protein was confirmed by Western blot, using a polyclonal antibody directed against the NS3 protease domain and a monoclonal antibody against the 5-1-1 epitope (HCV 4a).

Additionally, protease enzyme activity was monitored during purification as follows. An NS4a peptide (KKGSVVIV-GRIVLSGKPAIIPKK, SEQ ID NO:13), and the sample containing the NS34aPI protein, were diluted in 90 μl of reaction buffer (25 mM Tris, pH 7.5, 0.15M NaCl, 0.5 mM EDTA, 10% glycerol, 0.05 n-Dodecyl B-D-Maltoside, 5 mM DTT) and allowed to mix for 30 minutes at room temperature. 90 μl of the mixture were added to a microtiter plate (Costar, Inc., Corning, N.Y.) and 10 μl of HCV substrate (AnaSpec, Inc., San Jose Calif.) was added. The plate was mixed and read on a Fluostar plate reader. Results were expressed as relative fluorescence units (RFU) per minute.

Using these methods, the product of the 1 M NaCl extraction contained 3.7 RFU/min activity, the ammonium sulfate precipitate had an activity of 7.5 RFU/min and the product of the Poly U purification had an activity of 18.5 RFU/min.

II. Modified NS3 Antigens with Mutations in the Protease Domain

Modified NS3 antigens, with a mutation to the NS3 protease domain were produced using site-directed mutagenesis of the NS34aPI sequence described above. In particular, the codon for Ser-1165, in the protease catalytic triad, was mutated to an Ala codon. A diagram of the NS34aPI construct including a substitution of Ala for Ser at position 1165 is shown in FIG. 4A. The nucleotide and corresponding amino acid sequence of this construct is shown in FIGS. 5A-5C. This construct was termed "NS34aPI.1165."

Additionally, the modified NS3 protein depicted in FIG. 4C was produced. As with the protein described above, this modified NS3 also included the PI mutation in the helicase domain. The protein included amino acids 1678-1690 of NS4a, followed by the amino acid sequence SGS, then amino acids 1029 to 1657 of NS3. The SGS sequence provides a flexible linker sequence which allows the NS4a polypeptide to fold into the pocket within the protease to create an enzymatically active molecule. The nucleotide sequence and corresponding amino acid sequence of this protein is shown in FIGS. 7A-7C. This construct was termed "d.4a.t.NS3PI.1165."

Finally, a modified NS3 protein, shown in FIG. 4B, which included the Ala substitution at amino acid 1165, as well as the PI substitutions in the helicase domain, was produced as follows. The nucleotide sequence and corresponding amino acid sequence of this protein is shown in FIGS. 6A-6C. This construct was termed "NS3PI.1165."

To construct the NS3PI.1165 yeast expression vector, the following steps were taken. First, plasmid pSP72NS3NS4a.PI.HindIII/Cla$_i$ #9 was generated by ligation of a BglI/ClaI fragment (isolated from pAcHLT NS3NS4aPI, described above) with a HindIII/BglI synthetic oligonucleotide of 97 bp (below) then transformed into HB101.

```
                                        (SEQ ID NO:14)
HBg1-1
AGCTTACAAAACAAAATGCATCACCATCACCATCACGCGCC (SEQ ID NO:15)
Hbg1-2
GCGTACGCCGTGATGGGCGCGTGATGGTGATGGTGATGCAT
TTTGTTTTGTA (SEQ ID NO:16)
Hbg1-5
CATCACGGCGTACGCCCAGCAGACAAGGGGCCTCCTAGGGT
GCATAATCACCAGCCTAAC (SEQ ID NO:17)
Hbg1-6
AGGCTGGTGATTATGCACCCTAGGAGGCCCCTTGTCTGCTGG
```

After miniscreens and sequence confirmation, plasmid pSP72NS3NS4a.PIHindIII/Cla$_i$ #9 was retransformed into SCS110 E. coli competent cells that were Dam− methylation. This plasmid was then used as a template to mutate the Serine$_{1165}$ of the HCV1a NS3 protease catalytic triad to Alanine using site-directed mutagenesis (GeneTailor Site-Directed Mutagenesis, Invitrogen, San Diego Calif.), using the following PCR primers:

```
                                        (SEQ ID NO:18)
5' TTTCCTACTTGAAAGGCTCCgcaGGGGGTCCGCT 3'

(SEQ ID NO:19)
3' GGGGCCGGGTAAAGGATGAACTTTCCGAGG 5'
```

After miniscreen analysis and sequence verification, the clone with the correct sequence was named pSP72NS3NS4aPImut1165 #32. Next, this plasmid was digested with HindIII and AvrII (BlnI) to prepare a vector for ligation with a 58 base pair synthetic oligonucleotide encoding the 14aa of the N-terminus from the original HCV1a NS3 domain, using yeast preferred codons.

```
                                        (SEQ ID NO:20)
HA-1
AGCTTACAAAACAAAATGGCGCCAATCACTGCTTACGCTCAACAAACCAG
AGGCCTC (SEQ ID NO:21)
HA-2
CTAGGAGGCCTCTGGTTTGTTGAGCGTAAGCAGTGATTGGCGCCATTTTG
TTTTGTA
```

After HB101 transformation, miniscreen analysis and sequence verification the new plasmid with the correct sequence was named pSP72H3/ClaINS3mut1165 #15. Since the ClaI site of HCV1a NS3 domain is methylated, SCS110 E. coli competent cells were used to transform the pSP72H3/ClaINS3mut1165 #15 subclone. Next, this plasmid was digested with HindIII and ClaI to prepare a 761 bp fragment.

Second, a ClaI/EagI fragment of 1129 bp was isolated from baculovirus expression plasmid pAcHLTns3 ns4aPI. The ClaI/EagI fragment was ligated with a 195 bp synthetic oligonucleotide encoding the C-terminus of the NS3 domain plus the NS4a peptide into the pSP72 ClaI/SalI vector to create subclone pSP72NS3NS4aPI Cla/Sal #30 which was retransformed into SCS110 competent cells, a strain in which the ClaI site was not methylated as it was in HB101:

```
                                        (SEQ ID NO:22)
PI3p-1
GGCCGACCTGGAGGTCGTCACGAGCACCTGGGTGCTCGTTGGCGGCGTCC
TGGCTGCTTTGGCCGCGTATTGCCTGTCAACAGG (SEQ ID NO:23)
PI3p-2
CTGCGTGGTCATAGTGGGCAGGGTCGTCTTGTCCGGGAAGCCGGCAATCA
TACCTGACAGGGAAGTCCTCTAC (SEQ ID NO:24)
PI3p-3
GTCAGGTATGATTGCCGGCTTCCCGGACAAGACGACCCTGCCCACTATGA
CCACGCAGCCTGTTGACAGGCAATACGC (SEQ ID NO:25)
PI3p-4
GGCCAAAGCAGCCAGGACGCCGCCAACGAGCACCCAGGTGCTCGTGACGA
CCTCCAGGTC (SEQ ID NO:26)
PI3p-5
CGAGAGTTCGATGAGATGGAAGAGTGCTGATAAG (SEQ ID NO:27)
PI3p-6
TCGACTTATCAGCACTCTTCCATCTCATCGAACTCTCGGTAGAGGACTTC
CCT
```

From this plasmid, a vector was prepared by digesting with Ava3 and SalI restriction enzymes, thus eliminating the NS4a domain. Into this vector a 37 bp synthetic oligonucleotide was ligated and transformed into HB101.

```
                                        (SEQ ID NO:28)
avsal-1
TGTCGGCCGACCTGGAGGTCGTCACGTGATAAG (SEQ ID NO:29)
avsal-2
TCGACTTATCACGTGACGACCTCCAGGTCGGCCGACATGCA
```

After miniscreen analysis and sequence confirmation, pSP72 ClaISalI NS3PI subclone #101 was generated. This plasmid was again retransformed into SCS110, as described earlier to isolate a ClaI/SalI fragment of 1320 bp.

Lastly, the BamHI/HindIII ADH2/GAPDH promoter, HindIII/ClaI 761 bp fragment and ClaI/SalI 1320 bp fragment were ligated into the pBS24.1 BamHI/SalI yeast expression vector and transformed using E. coli strain HB101 competent cells. Miniprep analysis of the individual colonies led to the identification of clones with an expected fragment of 3284 bp. The construct was named pd.NS3PI.$_{1165}$ #21. Expression in S. cerevisiae AD3 strain yeast was checked as described above for pd.HCV1a.ns3 ns4aPI.

The d.4a.t.NS3PI.1165 yeast expression plasmid was produced as follows. A synthetic oligonucleotide of 100 bp encoding the NS4a peptide followed by the amino acid sequence Ser-Gly-Ser and amino acids 1029-1039 of the NS3 domain were ligated into the vector pSP72NS3NS4aPImut1165 #32 HindIII/AvrII (described above) and transformed into HB101.

```
                                              (SEQ ID NO:30)
HA-5
AGCTTACAAAACAAAATGGGCTGCGTG (SEQ ID NO:31)
HA-6
GACCCTGCCCACTATGACCACGCAGCCCATTTTGTTTTGTA (SEQ ID NO:32)
HA-7
GTCATAGTGGGCAGGGTCGTCTTGTCCGGTTCCGGTTCCATCACTGCTTA
CGCTCAACAAACCAGAGGCCTC (SEQ ID NO:33)
HA-8
CTAGGAGGCCTCTGGTTTGTTGAGCGTAAGCAGTGATGGAACCGGAACCG
GACAAGAC
```

After miniscreens and sequence verification, pSP724a-t-NS3PI.$_{1165}$ #14 was generated. The subsequent plasmid was then transformed into SCS110 for reasons described above, and a HindIII/ClaI fragment of 803 bp was isolated. To create the d.4a.t.NS3PI.1165 yeast expression plasmid, the ADH2/GAPDH BamHI/HindIII promoter was ligated with the 803 bp HindIII/ClaI fragment and the 1158 bp ClaI/SalI fragment encoding the 3' end of the NS3PI region into the pAB24 BamHI/SalI yeast expression vector. pd.4a-t-ns3.1165 #4 was transformed into S. cerevisiae AD3 yeast strain, and single transformants were checked for expression as described above for pd.HCV1a.ns3ns4aPI.

The proteins were purified as above. All of the mutant proteins had expression levels in yeast similar to that of NS34aPI, and were purified to similar purity as NS34aPI (more than 90% purity). SDS-PAGE and Western blot confirmed the lack of proteolytic activity of modified NS3 polypeptides. In particular, NS34aPI.1165 was shown to be the uncleaved, full-length protein, and NS3PI.1165 and NS34aPI.1165 did not cleave MEFA 7.1. Thus, the modified proteins lacked proteolytic activity.

EXAMPLE 2

Immunoassays Using the Mutated HCV Antigens

The HCV antigens and, in some cases as specified, MEFA 7.1 antigen, were coated onto plates for immunoassays as follows. MEFA 7.1 was produced as described in U.S. Pat. No. 6,632,601, incorporated herein by reference in its entirety. MEFA 7.1 is a natural substrate for the NS3 protease. HCV coating buffer (50 mM NaPO4 pH 7.0, 2 mM EDTA and 0.1% Chloroacetamide) was filtered through a 0.22µ filter unit. The following reagents were then added sequentially to the HCV coating buffer and stirred after each addition: 2 µg/ml BSA-Sulfhydryl Modified, from a 10 mg/ml solution (Bayer Corp. Pentex, Kankakee, Ill.); 5 mM DTT from a 1 M solution (Sigma, St. Louis, Mo.); 0.45 µg/ml NS3/4a (protein concentration of 0.3 mg/ml); 0.375 µg/ml MEFA 7.1 (protein concentration of 1 mg/ml). The final solution was stirred for 15 minutes at room temperature.

200 µl of the above solution was added to each well of a Costar high binding, flat bottom plate (Corning Inc., Corning, N.Y.) and the plates were incubated overnight in a moisture chamber. The plates were then washed with wash buffer (1×PBS, 0.1% TWEEN-20), Tapped dry and 285 µl Ortho Post-Coat Buffer (1×PBS, pH 7.4, 1% BSA, 3% sucrose) added. The plates were incubated for at least 1 hour, tapped and dried overnight at 2-8° C. The plates were pouched with desiccants for future use.

The performance of the modified NS3 antigens in comparison with NS34aPI that lacked the mutation to the proteolytic domain, was studied. Panels of commercially available human blood samples were used which were HCV-infected. The PHV panels shown in the tables below were purchased from Boston Biomedica, Inc., West Bridgewater, Mass. (BBI).

The HCV assay was conducted as follows. 200 µl of specimen diluent buffer (1 g/l casein, 100 mg/l recombinant human SOD, 1 g/l chloracetamide, 10 g/l BSA, 500 mg/l yeast extract, 0.366 g/l EDTA, 1.162 g/l KPO$_4$, 5 ml/l Tween-20, 29.22 g/l NaCl, 1.627 g/l NaPO$_4$, 1% SDS) was added to the coated plates. 20 µl of sample was then added. This was incubated at 37° C. for one hour. The plates were washed with wash buffer (1×PBS, pH 7.4, 0.1% Tween-20). 200 µl conjugate solution (a mouse anti-human IgG-HRP, such as mouse anti-human IgG-HRP diluted 1:22,000 in ORTHO HCV 3.0 ELISA Test System with Enhanced SAVe bulk conjugate diluent (Ortho-Clinical Diagnostics, Raritan, N.J.) was added and incubated for 60 minutes at 37° C. This was washed as above, and 200 µl substrate solution (1 OPD tablet/10 ml) was added. The OPD tablet contains o-phenylenediamine dihydrochloride and hydrogen peroxide for horse radish peroxidase reaction color development. This was incubated for 30 minutes at room temperature in the dark. The reaction was stopped by addition of 50 µl 4N H$_2$SO$_4$ and the plates were read at 492 nm, relative to absorbance at 690 nm as control.

Results are shown in Tables 3-6. In particular, Table 3 shows the results of a comparison of immunoassay performance of NS3PI.1165 and NS34aPI.1165 versus NS34aPI. As shown in Table 3, both of the protease deficient mutants were immunoreactive, having approximately 80-90% of the reactivity of the NS34aPI control molecule that retained proteolytic activity when coated at 2× the amount. Table 6 shows the results of a comparison of immunoassay performance of d.4a.t.NS3PI.1165, NS3PI.1165 and NS34aPI.1165 versus NS34aPI. As can be seen in Table 6, when coated at appropriate levels, d.4a.t.NS3PI.1165, NS3PI.1165 and NS34aPI.1165 displayed similar immunoreactivity to that of NS34aPI with d.4a.t.NS3PI.1165 showing the closest immunoreactivity to NS34aPI.

As can be seen in Tables 4 and 7, NS3PI.1165, NS34aPI.1165 and d.4a.t.NS3PI.1165 also achieved very similar immunoreactivity as NS34aPI when used in combination with MEFA 7.1.

Table 5 shows the results of a comparison of immunoassay performance of NS3PI.1165 and d.4a.t.NS3PI.1165 versus NS34aPI, in assays either in combination with MEFA 7.1 or without MEFA 7.1. As can be seen, both mutants, either used alone or in combination with MEFA 7.1, achieved immunoreactivity very similar to that of native NS34aPI. Thus, all the three modified NS3 proteins tested have immunoreactivity.

Figure 13:
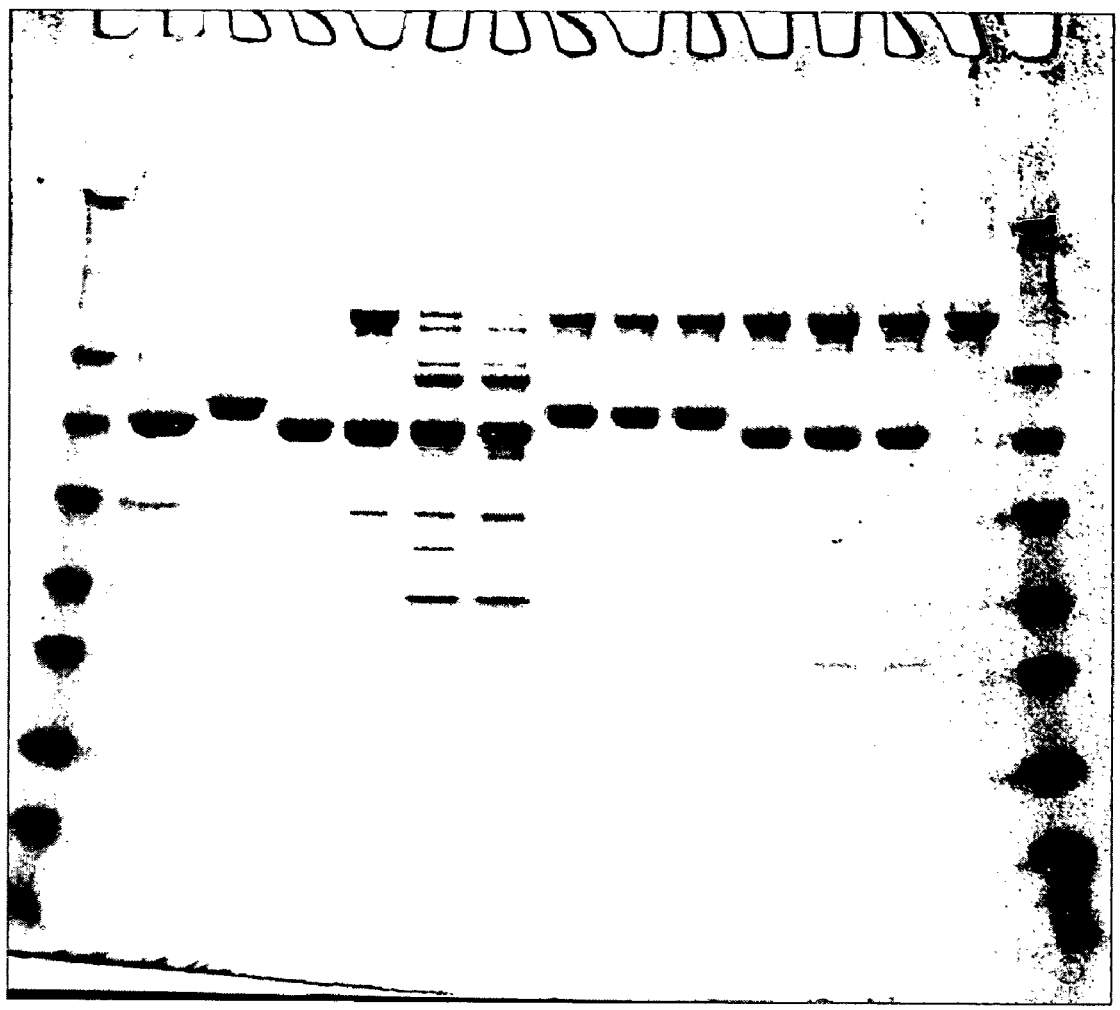
FIG. 13 is a representation of a Coomassie stained SDS-PAGE gel demonstrating that the NS3 mutant proteins do not undergo self-hydrolysis and do not cleave MEFA 7.1. Lane 1: NS34aPI; Lane 2: NS34aPI.1165; Lane 3: NS3PI.1165; Lane 4: NS34aPI+MEFA 7.1, t=0; Lane 5: NS34aPI+MEFA 7.1, t=40 min; Lane 6: NS34aPI+MEFA 7.1, t=2 hr; Lane 7: NS34aPI.1165+MEFA 7.1, t=0; Lane 8: NS34aPI.1165+MEFA 7.1, t=40 min; Lane 9: NS34aPI.1165+MEFA 7.1, t=2 hr; Lane 10: NS3PI.1165+MEFA 7.1, t=0; Lane 11: NS3PI.1165+MEFA 7.1, t=40 min; Lane 12: NS3PI.1165+MEFA 7.1, t=2 hr; Lane 13: MEFA 7.1.
Figure 14:
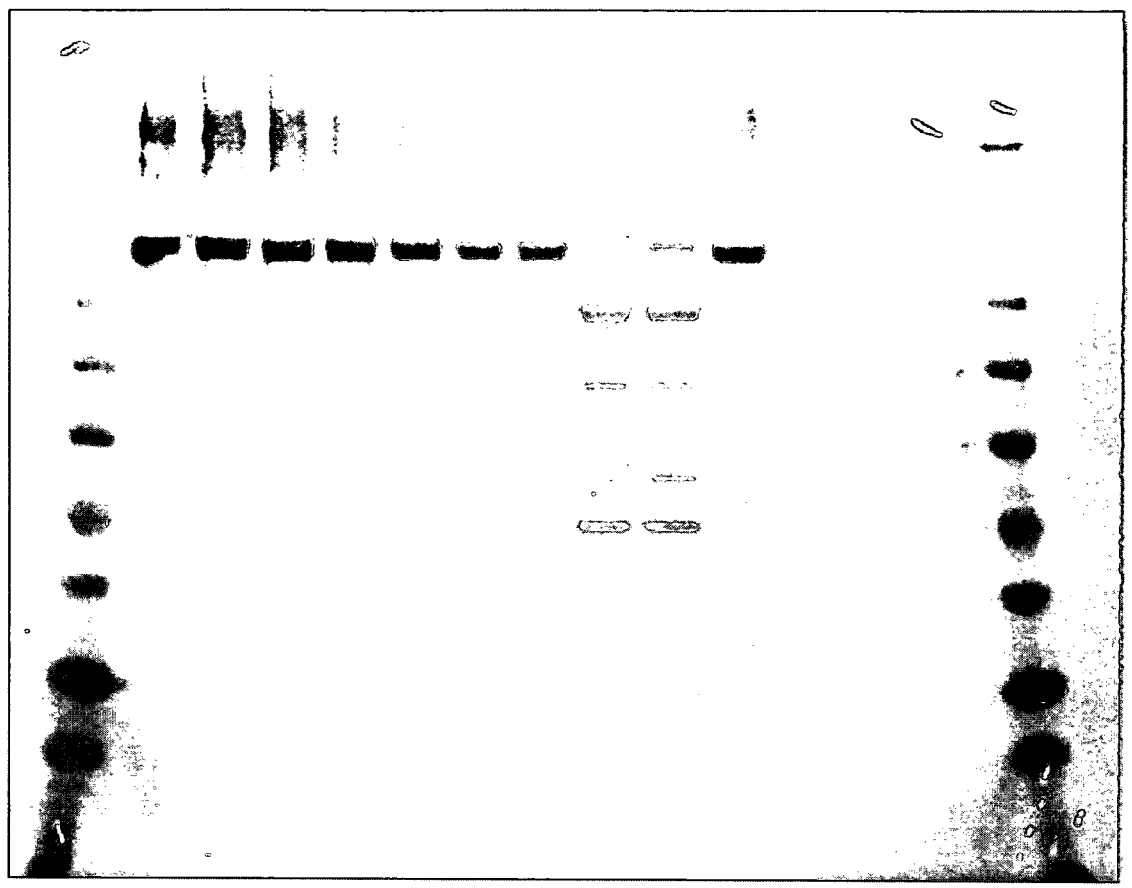
FIG. 14 is a representation of a Western blot, using anti-SOD as the primary antibody against MEFA 7.1 and anti-mouse-HRP as the secondary antibody, demonstrating that the NS3 mutant proteins do not undergo self-hydrolysis and do not cleave MEFA 7.1. Lane 1: NS34aPI; Lane 2: NS34aPI.1165; Lane 3: NS3PI.1165; Lane 4: NS34aPI+MEFA 7.1, t=0; Lane 5: NS34aPI+MEFA 7.1, t=40 min; Lane 6: NS34aPI+MEFA 7.1, t=2 hr; Lane 7: NS34aPI.1165+MEFA 7.1, t=0; Lane 8: NS34aPI.1165+MEFA 7.1, t=40 min; Lane 9: NS34aPI.1165+MEFA 7.1, t=2 hr; Lane 10: NS3PI.1165+MEFA 7.1, t=0; Lane 11: NS3PI.1165+MEFA 7.1, t=40 min; Lane 12: NS3PI.1165+MEFA 7.1, t=2 hr; Lane 13: MEFA 7.1.

These three modified NS3 proteins had helicase activity (data not shown) but were devoid of protease activity. Moreover, as shown in FIGS. 13 and 14, the modified NS3 mutant proteins did not cleave MEFA 7.1, a natural substrate of the NS3 protease.

To the best of the inventors' knowledge, this is the first demonstration that immunoreactivity and protease activity of NS3 can be separated, and that eliminating the serine protease activity does not affect antibody recognition sites of the protein.

EXAMPLE 3

Early Seroconversion Detection and Comparison with Commercially Available Assays The C33c and C200 antigens are very immunoreactive, and antibodies to these antigens are found in early seroconversion panels. Thus, the performance of d.4a.t.NS3PI.1165 plus MEFA 7.1 or NS34aPI plus MEFA 7.1 in immunoassays was studied using well-characterized, commercially available c33c and c200 panels of HCV-infected human blood samples to assess seroconversion sensitivity and these results were compared to those obtained in commercial anti-HCV ELISA kits. In particular, the Abbott PRISM assay (Abbott Laboratories, Abbott Park, Ill.), is commercially available and is an antibody-based detection assay. The assay was performed using the manufacturer's instructions. The ORTHO HCV Version 3.0 ELISA Test System (HCV 3.0) (Ortho Clinical Diagnostics, Raritan, N.J.) is an antibody-based detection assay. The assay was conducted using the manufacturer's instructions.

Results are shown in Table 7. For the panels tested, both NS34aPI plus MEFA 7.1 and d.4a.t.NS3PI.1165 plus MEFA 7.1 detected c33c- and c200-type antibody in the early seroconversion panels. The detections were 2-12 days ahead of Ortho HCV 3.0 and Abbott Prism assays.

TABLE 4

Immunoreactivity of NS3 Mutant Proteins Coated with MEFA 7.1

| | MEFA 7.1 75 ng NS34aPI 90 ng | | MEFA 7.1 75 ng NS3PI.1165-180 | | MEFA 7.1 75 ng NS34aPI.1165 180 ng | |
|---|---|---|---|---|---|---|
| | Signal | S/CO | Signal | S/CO | Signal | S/CO |
| PHV904 | 0.02 | 0.0 | 0.02 | 0.0 | 0.04 | 0.0 |
| PHV904 | 0.02 | 0.0 | 0.02 | 0.0 | 0.04 | 0.0 |
| PHV904 | 0.78 | 1.2 | 1.18 | 1.9 | 1.02 | 1.6 |
| PHV904 | 2.40 | 3.9 | 3.29 | 5.3 | 3.49 | 5.5 |
| PHV904 | 3.27 | 5.3 | 3.55 | 5.7 | 3.61 | 5.7 |
| PHV904 | 3.43 | 5.6 | 3.57 | 5.8 | 3.63 | 5.8 |
| PHV904 | 3.89 | 6.3 | 3.88 | 6.3 | 3.85 | 6.1 |
| PHV913 | 0.04 | 0.0 | 0.02 | 0.0 | 0.04 | 0.0 |
| PHV913 | 0.27 | 0.4 | 0.10 | 0.1 | 0.22 | 0.3 |
| PHV913 | 1.26 | 2.0 | 0.60 | 0.9 | 1.39 | 2.2 |
| PHV913 | 1.40 | 2.3 | 0.85 | 1.3 | 1.76 | 2.8 |
| PHV914 | 0.01 | 0.0 | 0.01 | 0.0 | 0.02 | 0.0 |
| PHV914 | 0.01 | 0.0 | 0.01 | 0.0 | 0.02 | 0.0 |
| PHV914 | 0.02 | 0.0 | 0.07 | 0.1 | 0.02 | 0.0 |
| PHV914 | 0.42 | 0.7 | 0.97 | 1.5 | 0.29 | 0.4 |
| PHV914 | 1.26 | 2.0 | 2.31 | 3.7 | 1.63 | 2.6 |
| PHV914 | 1.50 | 2.4 | 2.42 | 3.9 | 2.10 | 3.3 |
| PHV914 | 2.33 | 3.8 | 3.04 | 4.9 | 3.42 | 5.4 |
| PHV914 | 3.30 | 5.4 | 3.43 | 5.5 | 3.53 | 5.6 |
| PHV914 | 3.38 | 5.5 | 3.47 | 5.6 | 3.55 | 5.6 |

TABLE 3

Immunoreactivity of NS3 Mutant Proteins Coated alone without MEFA 7.1

| | NS3 PI.1165 | | | | NS34a PI.1165 | | | | NS34a PI | |
|---|---|---|---|---|---|---|---|---|---|---|
| | (90 ng) | | (180 ng) | | (90 ng) | | (180 ng) | | (90 ng) | |
| | Signal | S/CO | Signal | S/CO | Signal | S/CO | Signal | S/CO | Signal | S/CO |
| PHV904-1 | 0.024 | 0.04 | 0.027 | 0.04 | 0.029 | 0.05 | 0.037 | 0.06 | 0.034 | 0.054 |
| PHV904-2 | 0.023 | 0.04 | 0.026 | 0.04 | 0.033 | 0.05 | 0.037 | 0.06 | 0.024 | 0.038 |
| PHV904-3 | 0.523 | 0.85 | 0.785 | 1.28 | 0.904 | 1.47 | 1.041 | 1.68 | 1.590 | 2.560 |
| PHV904-4 | 1.002 | 1.64 | 1.785 | 2.90 | 3.020 | 4.91 | 3.211 | 5.19 | 3.435 | 5.532 |
| PHV904-5 | 1.521 | 2.49 | 2.720 | 4.42 | 3.528 | 5.74 | 3.559 | 5.75 | 3.547 | 5.711 |
| PHV904-6 | 2.076 | 3.39 | 3.210 | 5.22 | 3.569 | 5.80 | 3.582 | 5.79 | 3.533 | 5.689 |
| PHV904-7 | 2.466 | 4.03 | 3.903 | 6.35 | 3.874 | 6.30 | 3.874 | 6.26 | 3.874 | 6.238 |
| PHV913-1 | 0.012 | 0.02 | 0.013 | 0.02 | 0.020 | 0.03 | 0.026 | 0.04 | 0.025 | 0.041 |
| PHV913-2 | 0.013 | 0.02 | 0.013 | 0.02 | 0.016 | 0.03 | 0.022 | 0.04 | 0.023 | 0.037 |
| PHV913-3 | 0.044 | 0.07 | 0.057 | 0.09 | 0.033 | 0.05 | 0.053 | 0.09 | 0.057 | 0.092 |
| PHV913-4 | 0.182 | 0.30 | 0.260 | 0.42 | 0.145 | 0.23 | 0.175 | 0.28 | 0.346 | 0.557 |
| PHV914-1 | 0.012 | 0.02 | 0.011 | 0.02 | 0.014 | 0.02 | 0.023 | 0.04 | 0.020 | 0.032 |
| PHV914-2 | 0.012 | 0.02 | 0.014 | 0.02 | 0.016 | 0.03 | 0.018 | 0.03 | 0.018 | 0.029 |
| PHV914-3 | 0.056 | 0.09 | 0.085 | 0.14 | 0.018 | 0.03 | 0.021 | 0.03 | 0.086 | 0.139 |
| PHV914-4 | 0.388 | 0.63 | 0.606 | 0.99 | 0.163 | 0.27 | 0.268 | 0.43 | 1.732 | 2.789 |
| PHV914-5 | 0.606 | 0.99 | 1.040 | 1.69 | 0.728 | 1.18 | 1.164 | 1.88 | 3.098 | 4.989 |
| PHV914-6 | 0.687 | 1.12 | 1.186 | 1.93 | 0.722 | 1.17 | 1.507 | 2.44 | 3.314 | 5.337 |
| PHV914-7 | 0.974 | 1.59 | 1.536 | 2.50 | 2.565 | 4.17 | 3.122 | 5.04 | 3.442 | 5.542 |
| PHV914-8 | 1.550 | 2.53 | 2.510 | 4.08 | 3.416 | 5.55 | 3.474 | 5.61 | 3.453 | 5.560 |
| PHV914-9 | 2.122 | 3.47 | 3.098 | 5.04 | 3.480 | 5.66 | 3.494 | 5.64 | 3.486 | 5.614 |

TABLE 5

Immunoreactivity of NS3 Mutant Proteins Coated with MEFA 7.1 (left panel) or without MEFA 7.1 (right panel)

| | NS34aPI and NS3 mutants in combination with MEFA 7.1 | | | | | | NS34aPI and mutants alone | | | | | |
|---|---|---|---|---|---|---|---|---|---|---|---|---|
| | NS34a PI & MEFA 7.1 | | NS3PI.1165 & MEFA 7.1 | | 4A.t.NS3 & MEFA 7.1 | | NS34aPI | | NS3PI.1165 | | 4a.t.NS3 (S1165 A) | |
| | (90 ng) | (75 ng) | (360 ng) | (75 ng) | (180 ng) | (75 ng) | 90 ng | | 360 ng | | 180 ng | |
| | Signal | S/CO | Signal | S/CO | Signal | S/CO | Signal | S/C | Signal | S/C | Signal | S/C |
| PHV904-1 | −0.008 | −0.01 | 0.002 | 0.00 | 0.029 | 0.05 | 0.120 | 0.19 | 0.021 | 0.03 | 0.059 | 0.09 |
| PHV904-2 | −0.007 | −0.01 | 0.006 | 0.01 | 0.022 | 0.04 | 0.018 | 0.03 | 0.100 | 0.16 | 0.054 | 0.09 |
| PHV904-3 | 2.075 | 3.40 | 0.833 | 1.37 | 1.485 | 2.46 | 1.853 | 2.98 | 1.784 | 2.76 | 1.779 | 2.81 |
| PHV904-4 | 3.090 | 5.06 | 1.753 | 2.87 | 2.930 | 4.85 | 3.015 | 4.85 | 3.127 | 4.83 | 3.150 | 4.97 |
| PHV904-5 | 3.263 | 5.34 | 2.820 | 4.62 | 3.374 | 5.59 | 3.169 | 5.10 | 3.472 | 5.37 | 3.474 | 5.48 |
| PHV904-6 | 3.405 | 5.57 | 3.297 | 5.40 | 3.459 | 5.73 | 3.388 | 5.46 | 3.483 | 5.38 | 3.537 | 5.58 |
| PHV904-7 | 3.854 | 6.31 | 3.860 | 6.33 | 3.857 | 6.38 | 3.907 | 6.29 | 3.881 | 6.00 | 3.881 | 6.12 |
| PHV913-1 | 0.009 | 0.01 | 0.010 | 0.02 | 0.004 | 0.01 | 0.016 | 0.03 | 0.007 | 0.01 | 0.019 | 0.03 |
| PHV913-2 | 0.124 | 0.20 | 0.028 | 0.05 | 0.091 | 0.15 | 0.017 | 0.03 | 0.009 | 0.01 | 0.024 | 0.04 |
| PHV913-3 | 0.739 | 1.21 | 0.240 | 0.39 | 0.522 | 0.86 | 0.115 | 0.19 | 0.099 | 0.15 | 0.072 | 0.11 |
| PHV913-4 | 1.186 | 1.94 | 0.297 | 0.49 | 0.724 | 1.20 | 0.600 | 0.97 | 0.517 | 0.80 | 0.465 | 0.73 |
| PHV914-1 | 0.001 | 0.00 | −0.004 | −0.01 | −0.004 | −0.01 | 0.026 | 0.04 | 0.006 | 0.01 | 0.023 | 0.04 |
| PHV914-2 | 0.005 | 0.01 | −0.014 | −0.02 | 0.001 | 0.00 | 0.023 | 0.04 | 0.010 | 0.02 | 0.018 | 0.03 |
| PHV914-3 | 0.323 | 0.53 | 0.032 | 0.05 | 0.069 | 0.11 | 0.151 | 0.24 | 0.109 | 0.17 | 0.104 | 0.16 |
| PHV914-4 | 1.870 | 3.06 | 0.410 | 0.67 | 1.157 | 1.92 | 1.389 | 2.24 | 1.502 | 2.32 | 1.225 | 1.93 |
| PHV914-5 | 2.889 | 4.73 | 1.013 | 1.66 | 2.615 | 4.33 | 2.444 | 3.93 | 2.832 | 4.38 | 2.820 | 4.45 |
| PHV914-6 | 2.941 | 4.81 | 1.158 | 1.90 | 2.567 | 4.25 | 2.365 | 3.81 | 2.751 | 4.25 | 2.863 | 4.52 |
| PHV914-7 | 3.227 | 5.28 | 2.008 | 3.29 | 3.165 | 5.24 | 2.728 | 4.39 | 3.377 | 5.22 | 3.221 | 5.08 |
| PHV914-8 | 3.327 | 5.44 | 3.014 | 4.94 | 3.327 | 5.51 | 3.285 | 5.29 | 3.368 | 5.21 | 3.429 | 5.41 |
| PHV914-9 | 3.282 | 5.37 | 3.012 | 4.94 | 3.364 | 5.57 | 3.327 | 5.36 | 3.348 | 5.17 | 3.392 | 5.35 |

TABLE 6

Assay Performance of NS3/4aPI Coated Alone

| | NS3/4a PI | | 4a.t.NS3 PI (S1165 A) | | | | | | NS3 PI (S1165 A) | |
|---|---|---|---|---|---|---|---|---|---|---|
| | 90 ng | | 90 ng | | 180 ng | | 360 ng | | 90 ng | |
| BBI ID | Signal | S/C | Signal | S/C | Signal | S/C | Signal | S/C | Signal | S/C |
| PHV904-1 | 0.120 | 0.19 | 0.027 | 0.04 | 0.059 | 0.09 | 0.046 | 0.07 | 0.034 | 0.05 |
| PHV904-2 | 0.018 | 0.03 | 0.060 | 0.10 | 0.054 | 0.09 | 0.071 | 0.11 | 0.027 | 0.04 |
| PHV904-3 | 1.853 | 2.98 | 1.005 | 1.63 | 1.779 | 2.81 | 2.055 | 3.29 | 0.568 | 0.91 |
| PHV904-4 | 3.015 | 4.85 | 1.983 | 3.22 | 3.150 | 4.97 | 3.496 | 5.59 | 0.957 | 1.53 |
| PHV904-5 | 3.169 | 5.10 | 2.854 | 4.63 | 3.474 | 5.48 | 3.552 | 5.68 | 1.430 | 2.29 |
| PHV904-6 | 3.388 | 5.46 | 3.133 | 5.09 | 3.537 | 5.58 | 3.575 | 5.72 | 1.796 | 2.87 |
| PHV904-7 | 3.907 | 6.29 | 3.899 | 6.33 | 3.881 | 6.12 | 3.881 | 6.21 | 2.004 | 3.21 |
| PHV913-1 | 0.016 | 0.03 | 0.007 | 0.01 | 0.019 | 0.03 | 0.023 | 0.04 | 0.030 | 0.05 |
| PHV913-2 | 0.017 | 0.03 | 0.017 | 0.03 | 0.024 | 0.04 | 0.014 | 0.02 | 0.012 | 0.02 |
| PHV913-3 | 0.115 | 0.19 | 0.081 | 0.13 | 0.072 | 0.11 | 0.094 | 0.15 | 0.063 | 0.10 |
| PHV913-4 | 0.600 | 0.97 | 0.339 | 0.55 | 0.465 | 0.73 | 0.677 | 1.08 | 0.237 | 0.38 |
| PHV914-1 | 0.026 | 0.04 | 0.015 | 0.02 | 0.023 | 0.04 | 0.026 | 0.04 | 0.010 | 0.02 |
| PHV914-2 | 0.023 | 0.04 | 0.012 | 0.02 | 0.018 | 0.03 | 0.028 | 0.04 | 0.017 | 0.03 |
| PHV914-3 | 0.151 | 0.24 | 0.077 | 0.13 | 0.104 | 0.16 | 0.175 | 0.28 | 0.067 | 0.11 |
| PHV914-4 | 1.389 | 2.24 | 0.782 | 1.27 | 1.225 | 1.93 | 2.306 | 3.69 | 0.432 | 0.69 |
| PHV914-5 | 2.444 | 3.93 | 1.540 | 2.50 | 2.820 | 4.45 | 3.424 | 5.48 | 0.733 | 1.17 |
| PHV914-6 | 2.365 | 3.81 | 1.593 | 2.59 | 2.863 | 4.52 | 3.455 | 5.53 | 0.744 | 1.19 |
| PHV914-7 | 2.728 | 4.39 | 1.994 | 3.24 | 3.221 | 5.08 | 3.505 | 5.61 | 0.936 | 1.50 |
| PHV914-8 | 3.285 | 5.29 | 2.681 | 4.35 | 3.429 | 5.41 | 3.487 | 5.58 | 1.446 | 2.31 |
| PHV914-9 | 3.327 | 5.36 | 2.782 | 4.52 | 3.392 | 5.35 | 3.461 | 5.54 | 1.525 | 2.44 |

| | NS3 PI (S1165 A) | | | | NS3/4a PI (S1165 A) | | | | | |
|---|---|---|---|---|---|---|---|---|---|---|
| | 180 ng | | 360 ng | | 90 ng | | 180 ng | | 360 ng | |
| BBI ID | Signal | S/C | Signal | S/C | Signal | S/C | Signal | S/C | Signal | S/C |
| PHV904-1 | 0.042 | 0.07 | 0.021 | 0.03 | 0.036 | 0.06 | 0.032 | 0.05 | 0.041 | 0.06 |
| PHV904-2 | 0.033 | 0.05 | 0.100 | 0.16 | 0.030 | 0.05 | 0.033 | 0.05 | 0.038 | 0.06 |
| PHV904-3 | 1.117 | 1.79 | 1.784 | 2.76 | 0.880 | 1.41 | 1.247 | 1.97 | 1.709 | 2.67 |
| PHV904-4 | 2.202 | 3.52 | 3.127 | 4.83 | 2.480 | 3.98 | 3.096 | 4.90 | 3.298 | 5.16 |
| PHV904-5 | 2.928 | 4.69 | 3.472 | 5.37 | 2.998 | 4.81 | 3.411 | 5.40 | 3.496 | 5.47 |

TABLE 6-continued

Assay Performance of NS3/4aPI Coated Alone

| | | | | | | | | | | |
|---|---|---|---|---|---|---|---|---|---|---|
| PHV904-6 | 3.191 | 5.11 | 3.483 | 5.38 | 3.190 | 5.12 | 3.450 | 5.46 | 3.494 | 5.47 |
| PHV904-7 | 3.906 | 6.25 | 3.881 | 6.00 | 3.906 | 6.27 | 3.892 | 6.16 | 3.881 | 6.07 |
| PHV913-1 | 0.011 | 0.02 | 0.007 | 0.01 | 0.026 | 0.04 | 0.025 | 0.04 | 0.042 | 0.07 |
| PHV913-2 | 0.013 | 0.02 | 0.009 | 0.01 | 0.018 | 0.03 | 0.025 | 0.04 | 0.041 | 0.06 |
| PHV913-3 | 0.058 | 0.09 | 0.099 | 0.15 | 0.053 | 0.09 | 0.070 | 0.11 | 0.093 | 0.14 |
| PHV913-4 | 0.376 | 0.60 | 0.517 | 0.80 | 0.211 | 0.34 | 0.323 | 0.51 | 0.394 | 0.62 |
| PHV914-1 | 0.014 | 0.02 | 0.006 | 0.01 | 0.024 | 0.04 | 0.014 | 0.02 | 0.015 | 0.02 |
| PHV914-2 | 0.015 | 0.02 | 0.010 | 0.02 | 0.014 | 0.02 | 0.019 | 0.03 | 0.013 | 0.02 |
| PHV914-3 | 0.095 | 0.15 | 0.109 | 0.17 | 0.024 | 0.04 | 0.025 | 0.04 | 0.043 | 0.07 |
| PHV914-4 | 0.895 | 1.43 | 1.502 | 2.32 | 0.209 | 0.34 | 0.418 | 0.66 | 0.717 | 1.12 |
| PHV914-5 | 1.592 | 2.55 | 2.832 | 4.38 | 0.836 | 1.34 | 1.575 | 2.49 | 2.257 | 3.63 |
| PHV914-6 | 1.779 | 2.85 | 2.751 | 4.25 | 1.113 | 1.79 | 2.068 | 3.27 | 2.602 | 4.07 |
| PHV914-7 | 2.053 | 3.29 | 3.377 | 5.22 | 2.175 | 3.49 | 3.091 | 4.89 | 3.262 | 5.10 |
| PHV914-8 | 2.897 | 4.63 | 3.368 | 5.21 | 3.251 | 5.22 | 3.428 | 5.42 | 3.456 | 5.41 |
| PHV914-9 | 3.038 | 4.86 | 3.348 | 5.17 | 3.258 | 5.23 | 3.463 | 5.48 | 3.476 | 5.44 |

TABLE 7

Assay Performance: Earlier Seroconversion Detection

| | NS3/4a PI & MEFA 7.1 | | 4a.t.NS3 PI (S1165A) & MEFA 7.1 | | Field Data | | |
|---|---|---|---|---|---|---|---|
| BBI ID | (90 ng) Signal | (75 ng) S/CO | (180 ng) Signal | (75 ng) S/CO | HCV 3.0 s/co | Prism s/co | Days Ahead of Prism |
| PHV904-1 | −0.008 | −0.01 | 0.029 | 0.05 | | | |
| PHV904-2 | −0.007 | −0.01 | 0.022 | 0.04 | | | |
| PHV904-3 | 2.075 | 3.40 | 1.485 | 2.46 | | | |
| PHV904-4 | 3.090 | 5.06 | 2.930 | 4.85 | | | |
| PHV904-5 | 3.263 | 5.34 | 3.374 | 5.59 | | | |
| PHV904-6 | 3.405 | 5.57 | 3.459 | 5.73 | | | |
| PHV904-7 | 3.854 | 6.31 | 3.857 | 6.38 | | | |
| PHV913-1 | 0.009 | 0.01 | 0.004 | 0.01 | 0.01 | 0.08 | |
| PHV913-2 | 0.124 | 0.20 | 0.091 | 0.15 | 0.02 | 0.10 | >2 days |
| PHV913-3 | 0.739 | 1.21 | 0.522 | 0.86 | 0.43 | 0.50 | |
| PHV913-4 | 1.186 | 1.94 | 0.724 | 1.20 | 0.54 | 0.59 | |
| PHV914-1 | 0.001 | 0.00 | −0.004 | −0.01 | 0.00 | 0.06 | |
| PHV914-2 | 0.005 | 0.01 | 0.001 | 0.00 | 0.01 | 0.06 | |
| PHV914-3 | 0.323 | 0.53 | 0.069 | 0.11 | 0.01 | 0.06 | |
| PHV914-4 | 1.870 | 3.06 | 1.157 | 1.92 | 0.04 | 0.09 | >12 days |
| PHV914-5 | 2.889 | 4.73 | 2.615 | 4.33 | 0.33 | 0.47 | |
| PHV914-6 | 2.941 | 4.81 | 2.567 | 4.25 | 0.82 | 0.90 | |
| PHV914-7 | 3.227 | 5.28 | 3.165 | 5.24 | 3.10 | 2.41 | |
| PHV914-8 | 3.327 | 5.44 | 3.327 | 5.51 | 4.85 | 4.09 | |
| PHV914-9 | 3.282 | 5.37 | 3.364 | 5.57 | 4.85 | 4.52 | |

TABLE 8

Assay Performance: Genotype Dilutional Sensitivity

| Genotype | Dilution | NS3NS4a PI O.D. | MEFA 7.1 O.D. | MEFA 7.1 + NS3NS4a PI O.D. | Ortho HCV 3.0 O.D. | Monolisa Ver.2 Pasteur O.D. |
|---|---|---|---|---|---|---|
| 1b | 1:5000 | 2.929 | 1.396 | 2.074 | 0.393 | 0.218 |
| | 1:10000 | 2.506 | 0.826 | 1.099 | 0.159 | 0.084 |
| | 1:20000 | 1.78 | 0.355 | 0.403 | 0.045 | 0.028 |
| 2a/c | 1:2500 | | | 1.952 | 0.467 | 1.653 |
| | 1:5000 | 1.868 | 0.717 | 0.917 | 0.136 | 0.782 |
| | 1:10000 | 0.863 | 0.312 | 0.395 | 0.049 | 0.286 |
| 2b | 1:2500 | ND | ND | 1.430 | 0.295 | 0.658 |
| | 1:5000 | ND | ND | 0.551 | 0.108 | 0.207 |
| | 1:10000 | ND | ND | 0.225 | 0.032 | 0.061 |
| 3a | 1:2500 | | | 2.580 | 0.514 | 0.941 |
| | 1:5000 | 2.879 | 0.964 | 1.622 | 0.218 | 0.353 |
| | 1:10000 | 1.676 | 0.432 | 0.873 | 0.067 | 0.164 |
| | 1:20000 | 0.864 | 0.165 | 0.398 | 0.023 | 0.050 |
| 4a | 1:2500 | | | 2.831 | 0.632 | 0.462 |
| | 1:5000 | 2.4 | 0.824 | 1.752 | 0.193 | 0.181 |
| | 1:10000 | 1.169 | 0.265 | 0.717 | 0.069 | 0.076 |

TABLE 8-continued

Assay Performance: Genotype Dilutional Sensitivity

| Genotype | Dilution | NS3NS4a PI O.D. | MEFA 7.1 O.D. | MEFA 7.1 + NS3NS4a PI O.D. | Ortho HCV 3.0 O.D. | Monolisa Ver.2 Pasteur O.D. |
|---|---|---|---|---|---|---|
| 5a | 1:5000 | 2.889 | 1.763 | 2.744 | 0.827 | 0.988 |
|  | 1:10000 | 2.317 | 1.036 | 1.587 | 0.316 | 0.395 |
|  | 1:20000 | 1.315 | 0.416 | 0.726 | 0.097 | 0.120 |
| 6 | 1:100 | 3.406 | 2.872 | 3.602 | 3.594 | ND |
|  | 1:1000 | 2.978 | 2.455 | 3.224 | 2.863 | ND |
|  | 1:10000 | 2.841 | 0.984 | 1.192 | 0.380 | ND |
|  | 1:20000 | 2.262 | 0.509 |  |  |  |

Accordingly, modified HCV NS3 proteins and use thereof in detection assays have been disclosed. From the foregoing, it will be appreciated that, although specific embodiments of the invention have been described herein for purposes of illustration, various modifications may be made without deviating from the spirit and scope thereof.

We claim:

1. An immunoassay solid support comprising a polypeptide comprising a modified hepatitis C virus (HCV) NS3 protease domain such that protease activity of the modified NS3 domain is inhibited relative to protease activity of a corresponding HCV NS3 domain lacking the modification, wherein the polypeptide comprises the amino acid sequence of SEQ ID NO:6.

2. The immunoassay solid support of claim 1, wherein the polypeptide consists of the amino acid sequence of SEQ ID NO:6.

3. The immunoassay solid support of claim 1 wherein the solid support further comprises a multiple epitope fusion antigen bound to the support, wherein said polypeptide and/or said multiple epitope fusion antigen react specifically with anti-HCV antibodies present in a biological sample from an HCV-infected individual.

4. The immunoassay solid support of claim 3, wherein said multiple epitope fusion antigen comprises the amino acid sequence depicted in SEQ ID NO: 10, or an amino acid sequence with at least 80% sequence identity thereto which reacts specifically with anti-HCV antibodies present in a biological sample from an HCV-infected individual.

5. The immunoassay solid support of claim 3, wherein said multiple epitope fusion antigen comprises the amino acid sequence depicted in SEQ ID NO:10, or an amino acid sequence with at least 10% sequence identity thereto which reacts specifically with anti-HCV antibodies present in a biological sample from an HCV-infected individual.

6. The immunoassay solid support of claim 3, wherein said multiple epitope fusion antigen comprises the amino acid sequence depicted in SEQ ID NO:10, or an amino acid sequence with at least 98% sequence identity thereto which reacts specifically with anti-HCV antibodies present in a biological sample from an HCV-infected individual.

7. The immunoassay solid support of claim 3, wherein said multiple epitope fusion antigen consists of the amino acid sequence depicted in SEQ ID NO:10.

8. A method of detecting hepatitis C virus (HCV) infection in a biological sample, said method comprising:

(a) providing an immunoassay solid support according to claim 1;

(b) combining a biological sample with said solid support under conditions which allow HCV antibodies, when present in the biological sample, to bind to said polypeptide to form a first immune complex;

(c) adding to the solid support from step (b) under complex forming conditions a detectably labeled antibody, wherein said labeled antibody is reactive with said immune complex;

(d) detecting second immune complexes formed between the detectably labeled antibody and the first immune complex, if any, as an indication of HCV infection in the biological sample.

9. A method of detecting hepatitis C virus (HCV) infection in a biological sample, said method comprising:

(a) providing an immunoassay solid support according to claim 3;

(b) combining a biological sample with said solid support under conditions which allow HCV antibodies, when present in the biological sample, to bind to said polypeptide and/or said multiple epitope fusion antigen to form a first immune complex;

(c) adding to the solid support from step (b) under complex forming conditions a detectably labeled antibody, wherein said labeled antibody is reactive with said immune complex;

(d) detecting second immune complexes formed between the detectably labeled antibody and the first immune complex, if any, as an indication of HCV infection in the biological sample.

10. An immunodiagnostic test kit comprising the immunoassay solid support of claim 1, and instructions for conducting the immunodiagnostic test.

11. An isolated polypeptide comprising the amino acid sequence of SEQ ID NO:6, wherein the polypeptide comprises an NS3 conformational epitope.

12. The isolated polypeptide of claim 11, wherein the polypeptide consists of the amino acid sequence of SEQ ID NO:6.

13. A method of producing an immunoassay solid support, comprising:
(a) providing a solid support; and
(b) binding to the solid support at least one polypeptide according to claim 11.

14. The method of claim 13, further comprising binding to the solid support at a position on a multiple epitope fusion antigen.

* * * * *